US009988331B2

(12) United States Patent
Heydrich et al.

(10) Patent No.: US 9,988,331 B2
(45) Date of Patent: *Jun. 5, 2018

(54) METHOD FOR PRODUCING OPTICALLY ACTIVE, RACEMIC MENTHOL

(71) Applicant: BASF SE, Ludwigshafen (DE)

(72) Inventors: Gunnar Heydrich, Limburgerhof (DE); Gabriele Gralla, Mannheim (DE); Matthias Rauls, Blieskastel (DE); Joachim Schmidt-Leithoff, Mannheim (DE); Klaus Ebel, Lampertheim (DE); Wolfgang Krause, Brühl-Rohrhof (DE); Steffen Oehlenschläger, Ludwigshafen (DE); Christoph Jäkel, Limburgerhof (DE); Marko Friedrich, Lorsch (DE); Eike Johannes Bergner, Friesenheim-Heiligenzell (DE); Nawid Kashani-Shirazi, Ilvesheim (DE); Rocco Paciello, Bad Dürkheim (DE)

(73) Assignee: BASF SE (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/658,003

(22) Filed: Oct. 23, 2012

(65) Prior Publication Data

US 2013/0046118 A1 Feb. 21, 2013

Related U.S. Application Data

(63) Continuation of application No. 12/744,110, filed as application No. PCT/EP2008/065503 on Nov. 13, 2008, now Pat. No. 8,318,985.

(30) Foreign Application Priority Data

Nov. 30, 2007 (EP) ..................... 07122036

(51) Int. Cl.
C07C 29/56 (2006.01)
C07C 29/17 (2006.01)
C07C 29/78 (2006.01)
C07C 45/62 (2006.01)
C07C 45/82 (2006.01)

(52) U.S. Cl.
CPC ............ *C07C 29/56* (2013.01); *C07C 29/172* (2013.01); *C07C 29/78* (2013.01); *C07C 45/62* (2013.01); *C07C 45/82* (2013.01); *C07B 2200/07* (2013.01); *C07C 2101/14* (2013.01); *C07C 2101/16* (2013.01)

(58) Field of Classification Search
None
See application file for complete search history.

(56) References Cited

U.S. PATENT DOCUMENTS

| | | |
|---|---|---|
| 1,930,411 A | 10/1933 | Blagden |
| 2,471,134 A | 5/1949 | Wright |
| 2,662,052 A | 12/1953 | Bridger et al. |
| 2,827,497 A | 3/1958 | Bottoms |
| 3,023,253 A | 2/1962 | Bain et al. |
| 4,230,533 A | 10/1980 | Giroux |
| 4,237,072 A | 12/1980 | Aviron-Violet et al. |
| 4,874,473 A | 10/1989 | Arlt et al. |
| 5,037,793 A | 8/1991 | Toussaint et al. |
| 5,530,127 A | 6/1996 | Reif et al. |
| 5,785,819 A | 7/1998 | Kaibel et al. |
| 5,914,012 A | 6/1999 | Kaibel et al. |
| 6,175,044 B1 | 1/2001 | Therre et al. |
| 6,387,222 B1 | 5/2002 | Tragut et al. |
| 6,774,269 B2 | 8/2004 | Iwata et al. |
| 6,838,061 B1 | 1/2005 | Berg et al. |
| 7,067,707 B2 | 6/2006 | Piepho et al. |
| 7,534,921 B2 | 5/2009 | Jäkel et al. |
| 7,608,742 B2 | 10/2009 | Friedrich et al. |
| 7,868,211 B2 | 1/2011 | Rauls et al. |
| 2003/0106786 A1 | 6/2003 | Kaibel et al. |
| 2005/0169987 A1 | 8/2005 | Korber |
| 2006/0167322 A1 | 7/2006 | Kuhn et al. |
| 2010/0016642 A1 | 1/2010 | Heydrich et al. |

FOREIGN PATENT DOCUMENTS

| | | |
|---|---|---|
| CA | 1242309 | 9/1988 |
| DE | 568085 | 1/1933 |
| DE | 577036 | 5/1933 |

(Continued)

OTHER PUBLICATIONS

Trasarti, et al., "Highly Selective Synthesis of Menthols from Citral in a One-Step Process", *Journal of Catalysis*, vol. 224, pp. 484-488 (2004).

(Continued)

*Primary Examiner* — Brian J Davis
(74) *Attorney, Agent, or Firm* — Drinker Biddle & Reath LLP

(57) ABSTRACT

The present invention relates to a particularly economic overall method for producing menthol, specifically for producing optically active, essentially enantiomerically and diastereomerically pure L-menthol and racemic menthol, starting from the starting material citral which is available inexpensively on an industrial scale. The method has the following steps a.1) catalytic hydrogenation of neral and/or geranial to give citronellal, b.1) cyclization of citronellal to isopulegol in the presence of an acidic catalyst, c.1) purification of isopulegol by crystallization and d.1) catalytic hydrogenation of isopulegol to give menthol.

15 Claims, 2 Drawing Sheets

(56) References Cited

FOREIGN PATENT DOCUMENTS

| | | |
|---|---|---|
| DE | 1189073 | 3/1965 |
| DE | 3302525 A1 | 7/1984 |
| DE | 3522234 A1 | 1/1987 |
| DE | 10223974 A1 | 12/2003 |
| DE | 10239274 A1 | 3/2004 |
| DE | 10330934 A1 | 2/2005 |
| EP | 0000315 A1 | 1/1979 |
| EP | 0122367 A2 | 10/1984 |
| EP | 0126288 A2 | 11/1984 |
| EP | 133510 A1 | 2/1985 |
| EP | 0242778 A1 | 10/1987 |
| EP | 0394842 A1 | 10/1990 |
| EP | 0640367 A1 | 3/1995 |
| EP | 0694514 A2 | 1/1996 |
| EP | 0696572 A1 | 2/1996 |
| EP | 0780147 A2 | 6/1997 |
| EP | 0804951 A2 | 11/1997 |
| EP | 0992477 A1 | 4/2000 |
| EP | 1140349 | 10/2001 |
| EP | 1225163 A2 | 7/2002 |
| EP | 1514955 A1 | 3/2005 |
| EP | 1532091 | 5/2005 |
| GB | 1503723 | 9/1920 |
| GB | 285394 | 7/1928 |
| GB | 285833 | 5/1929 |
| JP | H08-119924 A | 5/1996 |
| WO | WO-00/30743 A1 | 6/2000 |
| WO | 1053974 A1 | 11/2000 |
| WO | WO-03/101924 A1 | 12/2003 |
| WO | WO-2004/007414 A1 | 1/2004 |
| WO | WO-2004/018394 A2 | 3/2004 |
| WO | WO-2004/089299 A2 | 10/2004 |
| WO | WO-2004/101480 A1 | 11/2004 |
| WO | WO-2006/040096 A1 | 4/2006 |
| WO | WO-2006/092433 A1 | 9/2006 |
| WO | WO-2007/023109 A1 | 3/2007 |
| WO | WO-2007/039342 A1 | 4/2007 |
| WO | WO-2007/039366 A1 | 4/2007 |
| WO | WO-2007/071512 A1 | 6/2007 |
| WO | WO-2008/025851 A1 | 3/2008 |

OTHER PUBLICATIONS

Trasarti, et al., "Design of Catalyst Systems for the One-Pot Synthesis of Menthols from Citral", *Journal of Catalysis*, pp. 155-165 (2007).

METHOD FOR PRODUCING OPTICALLY ACTIVE, RACEMIC MENTHOL

RELATED APPLICATIONS

This application is a continuation application of U.S. patent application Ser. No. 12/744,110, filed May 21, 2010, which issued as U.S. Pat. No. 8,318,985, which is a national stage application (under 35 U.S.C. § 371) of PCT/EP2008/065503, filed Nov. 13, 2008, which claims benefit of European Application No. 07122036.2, filed Nov. 30, 2007.

The present invention relates to a particularly economic overall method for producing menthol, specifically for producing optically active, essentially enantiomerically and diastereomerically pure L-menthol and racemic menthol starting from the starting material citral which is available inexpensively on an industrial scale. Specifically, the present invention relates to a method for producing optically active, essentially enantiomerically pure, menthol and racemic menthol while largely avoiding undesired waste and by-products.

menthol, specifically the levorotary enantiomer L-(−)-menthol, is, on account of its well known cooling properties, one of the most economically significant aroma chemicals. The requirement of optically active menthol, estimated worldwide at about 16 500 t, continues to be met largely from natural sources such as, for example, by crystallization of L-menthol from natural oils, specifically the oil pressed from Mentha arvensis at low temperature. Availability and quality of the menthol thus available are therefore heavily dependent on fluctuations in yearly harvest yields and thus on climatic factors that are difficult to predict, which can have a disadvantageous effect on the price stability of said raw material. In addition, there is a high demand worldwide for racemic menthol in good quality; this is usually used on account of its lower price if it seems suitable for the particular application.

Methods for the synthesis of racemic or optically active menthol have been known for a long time to the person skilled in the art and are described in detail, for example, in "Mint: the genus menthe" by R. Hopp and B. M. Lawrence, CRC Press, Taylor & Francis Group, 2007, pages 371-397. The known methods for producing menthol lead either to racemic or to optically active menthol, with optically active menthol being obtained partially synthetically starting from starting materials available in optically active form from natural sources. In addition, there is a method for producing L-menthol starting from myrcen, which is firstly converted to an enamine and then subjected to an asymmetric isomerization, as described, for example, in "Catalytic Asymmetric Synthesis", by S. Akutagawa, K. Tani, Wiley-VCH, 2000, chapter 3, pp. 145-161 and S. Otsuka, K. Tani, Synthesis 1992, 665-680.

One aim of the enantioselective syntheses of L-menthol consists in providing said compound in high enantiomer purity. Here, in the case of enantioselective totally synthetic methods for producing menthol, the extent to which one enantiomer is obtained in preference over the other is determined by the asymmetric induction of the reaction during which the first asymmetric carbon atom is formed, the so-called chirogenic state.

In the case of syntheses to be carried out on an industrial scale, those chirogenic stages or reactions are to be preferred in which enantioselective catalysts are used. These are usually considerably superior from an economic point of view over the likewise possible reactions using stoichiometric amounts of chiral auxiliaries. The extent of the asymmetric induction in the case of enantioselectively catalyzed reactions to be carried out with preference is determined by the efficiency of the chiral catalyst system and is thus fixed for a particular catalyst and the reaction conditions selected in each case. As a result, the ratio at which, in a method carried out on an industrial scale, optically active menthol is formed besides the racemic menthol formed as a result of incomplete asymmetric induction is also fixed and can only be adjusted by exchanging the catalyst system, which is complex, or by changing the reaction conditions. Both can only be effected at considerable cost, especially in the case of reactions on an industrial scale.

Against this background, the object of the present invention was to provide a method which makes it possible to produce optically active menthol, preferably L-menthol and racemic menthol in varying, demand-led amounts without exchanging the enantioselective catalyst system and/or without needing to change the reaction conditions and without one of the products thereby being obtained in excess. The method should be suitable for reactions on an industrial scale and permit the use of readily available, inexpensive starting materials. Moreover, the method should produce a high overall yield in a small number of total stages. Moreover, in the course of the chirogenic reaction stage, an inexpensive and readily available enantioselective catalyst system should be used.

The object was achieved according to the invention through the provision of a method for producing menthol, comprising the steps
  a.1) catalytic hydrogenation of neral and/or geranial to give citronellal,
  b.1) cyclization of citronellal to give isopulegol in the presence of an acidic
  catalyst,
  c.1) purification of isopulegol by crystallization and
  d.1) catalytic hydrogenation of isopulegol to give menthol.

A BRIEF DESCRIPTION OF THE FIGURES

A DETAILED DESCRIPTION OF THE INVENTION

Figure 1:
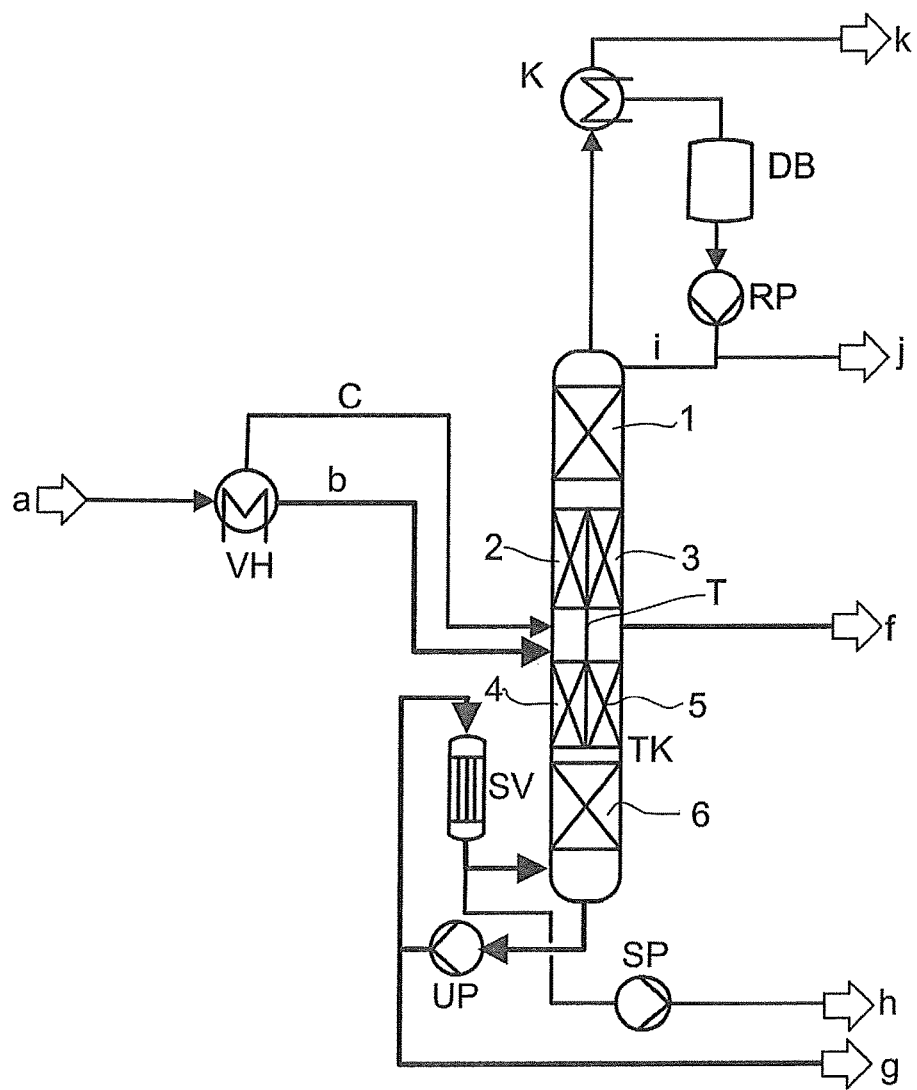
FIG. 1 shows in diagrammatic form, one preferred embodiment of the inventively preferred, optional separation of the neral and geranial comprising substance mixture to be used into a low-neral top fraction (j), a neral-rich side fraction (f) and a low-neral bottom fraction (g).

The starting materials for carrying out the method according to the invention are the α,β-unsaturated aldehydes neral of the formula (II)

and/or geranial of the formula (III)

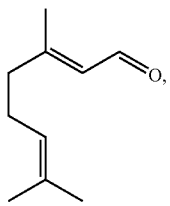
(III)

in each case in pure form or preferably in the form of mixtures with one another. Preferred mixtures of geranial and neral are those which comprise more than 90% by weight, preferably 95 to 99.5% by weight and particularly preferably 96 and most preferably 97 to 99.5% by weight, of geranial and neral, where small amounts of secondary components, for example water or solvent residues, may also be present and where the data in % by weight refer here, as throughout the entire disclosure, to the total amount of the respective mixtures.

The composition of the neral- and geranial-containing substance mixtures which can be used according to the invention can be varied within wide limits. According to the invention, preference is given to those mixtures which comprise about 0.1 to about 20% by weight, preferably about 0.1 to about 10% by weight, particularly preferably about 0.5 to about 5% by weight and very particularly preferably about 0.5 to 3% by weight, of geranial and about 80% by weight to about 99.9% by weight, preferably about 90% by weight to about 99.9% by weight, particularly preferably about 95% by weight to about 99.5% by weight and very particularly preferably about 96 to 99% by weight, of neral, where all of the data in % by weight refer to the total amount of the respective substance mixtures.

As starting material for carrying out the method according to the invention it is also possible to use geranial- and neral-containing mixtures which comprise geranial in a larger fraction than described previously, such as, for example, the mixture of geranial and neral known as citral. Citral consists in equilibrium of about 50% by weight of geranial and of about 50% by weight of neral and is readily available on an industrial scale, for example by thermal cleavage of 3-methyl-2-buten-1-al diprenylacetal with the elimination of prenol to give cis/trans-prenyl (3-methylbutadienyl)ether, Claisen rearrangement thereof to give 2,4,4-trimethyl-3-formyl-1,5-hexadiene and subsequent Cope rearrangement thereof, as described, for example, in EP 0 992 477, to which reference is hereby made in its entirety and which is thus part of the present disclosure, and also the references cited therein.

Step 0): Distillative Separation of Neral- and Geranial-Containing Substance Mixtures When using geranial- and neral-containing mixtures, for example when using the above-described citral, it has proven to be advantageous if the two isomeric compounds, which differ merely in the configuration of the α,β-position double bond, can be separated, purified and/or enriched by distillative methods. This makes it possible, for example starting from the citral as described above, to provide mixtures of neral and geranial in virtually any desired mixing ratio. In this way, enriched or pure geranial or neral, preferably neral, is accessible starting from neral- and geranial-containing mixtures, preferably starting from citral as described above.

Within the context of a preferred embodiment, the method according to the invention for producing menthol accordingly additionally comprises, as optional step 0), the distillative separation of geranial- and neral-containing mixtures to give enriched or pure geranial or neral, preferably neral.

Moreover, it has been found that the distillative separation of geranial- and neral-containing mixtures can be carried out particularly advantageously by means of a dividing wall column or an interconnection of thermally coupled columns. In this way, neral in particular is accessible in pure or enriched form through distillative separation of substance mixtures comprising geranial and neral.

Said distillative separation of geranial- and neral-containing mixtures is advantageously carried out continuously. Within the context of a preferred embodiment, for the distillative separation of geranial- and neral-containing mixtures, a continuous method for producing neral of the formula (II) in pure or enriched form by distillative removal of neral from substance mixtures comprising neral and geranial of the formula (III) is inserted, the distillative removal being carried out in a dividing wall column or in an interconnection of two distillation columns in the form of a thermal coupling having 80 to 200 theoretical plates and one or more side take-off points at an absolute operating pressure of from 5 to 200 mbar.

Suitable feed materials for carrying out this preferred embodiment of the distillative separation method of neral- and geranial-containing mixtures are substance mixtures which comprise neral and geranial, preferably those which consist predominantly of the double-bond isomers neral and geranial. Among these, preference is given to those substance mixtures which comprise at least 90% by weight to 100% by weight, particularly preferably at least 95 to 98% by weight (in each case based on the total amount of the respective substance mixture) of geranial and neral or consist thereof in the specified fractions and in addition can comprise to a low extent, i.e. in a fraction of up to 10% by weight, preferably up to 5% by weight (in each case based on the total amount of the respective substance mixture) also further components such as, for example, isomers, by-products or impurities. One preferred feed material is synthetically produced citral, especially that which has been obtained by thermal cleavage of 3-methyl-2-buten-1-al diprenylacetal with elimination of prenol to give cis/trans-prenyl (3-methylbutadienyl)ether, Claisen rearrangement thereof to give 2,4,4-trimethyl-3-formyl-1,5-hexadiene and subsequent Cope rearrangement thereof, as described, for example, in EP 0 992 477. This comprises typically about 45 to about 55% by weight of neral as well as about 55 to about 45% by weight and about 1 to 5% by weight of further compounds and/or impurities.

Within the context of a particular embodiment, the method according to the invention comprises, as additional inserted step, the aforementioned production method of citral starting from 3-methyl-2-buten-1-al diprenylacetal.

Within the context of a preferred embodiment of the separation method of geranial- and neral-containing mixtures that can be used according to the invention, a substance mixture is used which consists of 30 to 70% by weight, preferably of 40 to 60% by weight, of neral, of 70 to 30% by weight, preferably of 60 to 40% by weight, of geranial and of 0 to 5% by weight of further components, where the percentages add up to 100% by weight.

The distillative removal to be carried out preferably according to the invention is usually carried out by separating the neral and geranial comprising substance mixture used into, in each case, one or more low-boiling, medium-boiling and high-boiling fraction or fractions, and removing neral in pure or enriched form as medium-boiling fraction at the side take-off point of the dividing wall column used or the interconnection of two distillation columns in the form of a thermal coupling in liquid or gaseous form.

Accordingly, the distillative separating method that can preferably be used within the context of the optional step 0) for separating neral- and geranial-containing substance mixtures is also a continuous method for isolating neral, preferably a continuous method for isolating neral in pure or enriched form by distillative removal of neral from substance mixtures comprising neral and geranial, the distillative removal being carried out in a dividing wall column or in an interconnection of two distillation columns in the form of a thermal coupling having 80 to 200 theoretical plates and one or more side take-off points at an absolute operating pressure, i.e. at an absolute pressure in the dividing wall column or the interconnection of two distillation columns in the form of a thermal coupling of from 5 to 200 mbar.

The dividing wall column to be used preferably for the distillative separation within the context of optional step 0) for the separation of neral- and geranial-containing substance mixtures and/or the interconnection of two distillation columns in the form of a thermal coupling has or have 80 to 200, preferably 100 to 180, theoretical plates and one or more, preferably 1 to 3, particularly preferably 1 or 2, side take-off points. Preference is given to using a dividing wall column as described above.

The method for producing pure or enriched neral to be carried out preferably within the context of the method according to the invention is carried out at an absolute operating pressure in the dividing wall column or in the interconnection of two distillation columns in the form of a thermal coupling of from 5 to 200 mbar, preferably from 5 to 100 mbar, particularly preferably from 5 to 70 mbar and very particularly preferably from 10 to 50 mbar and especially preferably from 10 to 40 mbar. Preferably, the dividing wall column or the interconnection of two distillation columns in the form of a thermal coupling is operated here such that the absolute top pressure is 10 to 50 mbar, preferably 10 to 40 mbar. Likewise preferably, the dividing wall column or the interconnection of two distillation columns in the form of a thermal coupling is operated here such that the absolute bottom pressure is 5 to 200 mbar, preferably 10 to 100 and particularly preferably 20 to 50 mbar.

The reflux ratio when carrying out the method for the distillative separation of geranial and neral can be varied within wide limits and is usually about 5:1 to about 2000:1, preferably about 20:1 to 1000:1. Also advantageous is a dephlegmator procedure, i.e. only the return stream is condensed in the top condenser of the column and fed back to the column. In such an energetically favorable case of partial condensation, the top product to be discharged is produced exclusively in the aftercooler, which can be operated at a lower temperature.

The term "neral in enriched form" is to be understood as meaning neral-containing substance mixtures which have a higher content of neral than the neral or geranial comprising substance mixture used in each case according to the invention. Preferably, the term neral in enriched form is to be understood as meaning neral which has a purity, i.e. a neral content, of from 80 to 95% by weight, preferably from 85 to 95% by weight and very particularly preferably from 90 to 95% by weight. The method according to the invention also permits the production of neral (cis-citral) in pure form. The term "neral in pure form" is to be understood as meaning neral with a content greater than or equal to 95, 96 or 97% by weight, preferably greater than or equal to 98% by weight and particularly preferably 98 to 99.5% by weight. Particularly preferably, the term "neral in pure form" is to be understood as meaning neral which has a geranial content of up to 1% by weight, preferably of from 0.05 to 0.5% by weight and particularly preferably from 0.1 to 0.3% by weight. Likewise preferably, the neral in pure form accessible according to the invention has a content of isocitrals of the formulae (IV), (V) and (VI)

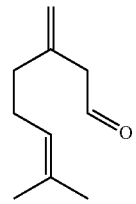

(IV)

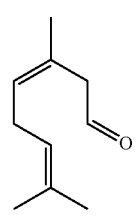

(V)

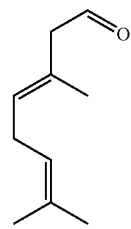

(VI)

of up to 2% by weight, preferably of from 0.1 to 1% by weight, where all of the data within the context of the present invention refer to the total amount of the respective substance mixtures.

The feed, i.e. the substance mixture to be used, can be fed in liquid or gaseous form into the dividing wall column or the interconnection of two distillation columns in the form of a thermal coupling, preferably into the dividing wall column, and be separated there into a top and bottom fraction and also one or more, preferably into two or more, side take-offs as described above. In one side take-off, the neral product of value is produced in the desired purity. In one particular embodiment, a postcondenser is connected downstream of the top condenser of the column and is cooled with cooling liquid (for example sols), and a low-neral low-boiling fraction is also produced therein.

For the continuous distillative fractionation of multisubstance mixtures, according to the prior art, various process variants can be used. In the simplest case, the feed mixture is fractionated into two fractions, a low-boiling top fraction and a high-boiling bottom fraction. When separating feed mixtures into more than two fractions, it is necessary to use a plurality of distillation columns according to this process variant. In order to limit the apparatus complexity, columns with liquid or vaporous side take-offs are used if possible in the separation of multisubstance mixtures. However, the possible use of distillation columns with side take-offs is severely restricted by the fact that the products removed at the side take-off points are never completely pure. In the case of side removals in the rectifying section, which are usually in liquid form, the side product still comprises fractions of low boiler components which should be removed via the top. The same applies for side removals in the stripping section, which mostly take place in vaporous form, in which the side product still has high-boiling fractions. The use of conventional side take-off columns is therefore restricted to cases where contaminated side products are permissible.

One possible remedy is offered by dividing wall columns. This column type is described, for example, in U.S. Pat. No. 2,471,134; U.S. Pat. No. 4,230,533; EP 0 122 367; EP 0 126 288; EP 0 133 510; Chem. Eng. Technol. 10 (1987) 92-98; Chem.-Ing.-Tech. 61 (1989) No. 1, 16-25; Gas Separation and Purification 4 (1990) 109-114; Process Engineering 2 (1993) 33-34; Trans IChemE 72 (1994) Part A 639-644 and Chemical Engineering 7 (1997) 72-76.

In the case of this design, it is possible to remove side products likewise in pure form. In the middle region, above and below the feed point and the side removal, is mounted a dividing wall which seals the feed section from the removal section and prevents cross-mixing of liquid and vapor streams in this column section. As a result, the number of distillation columns required in total is reduced when separating multisubstance mixtures. Since this column type constitutes an apparatus simplification of thermally coupled distillation columns, it moreover also has a particularly low energy consumption. A description of thermally coupled distillation columns, which can be designed in various apparatus configurations, can likewise be found in the aforementioned references in the specialist literature. Dividing wall columns and thermally coupled columns offer advantages over the arrangement of conventional distillation columns both with regard to the energy requirement and also the investment costs, and are therefore increasingly being used industrially.

FIG. 1 shows, in diagrammatic form, one preferred embodiment of the inventively preferred, optional separation of the neral and geranial comprising substance mixture to be used into a low-neral top fraction (j), a neral-rich side fraction (f) and a low-neral bottom fraction (g). The neral- and geranial-containing feed to the dividing wall column can take place in liquid form (b), in gaseous form (c), or in gaseous and liquid form.

Figure 2:
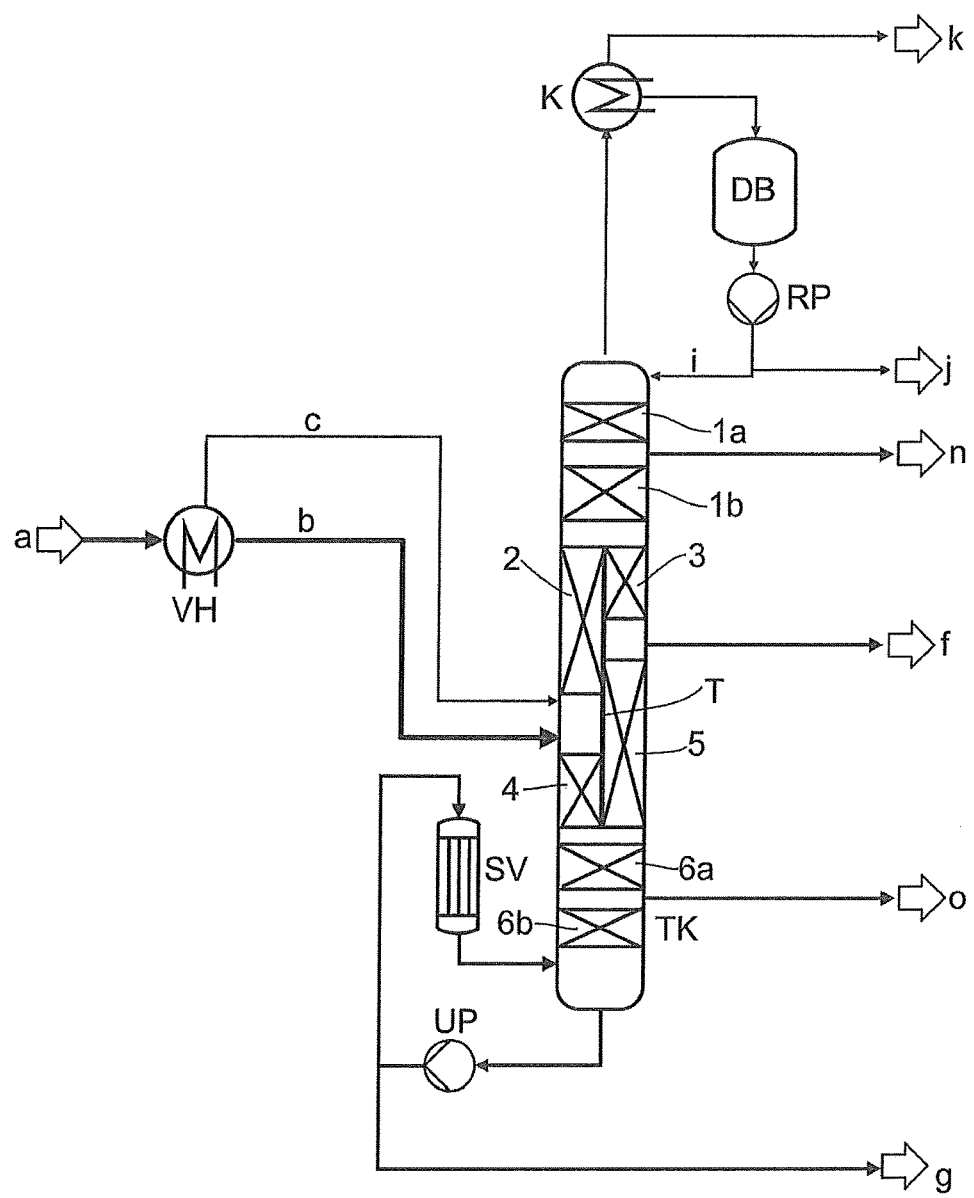
FIG. 2 shows in diagrammatic form, a particularly preferred embodiment of the method according to the invention for producing neral in pure or enriched form, in which, in addition to the features specified under FIG. 1, including the side take-off (f), the side take-off points (n) and (o) are provided.

FIG. 2 shows, in diagrammatic form, a particularly preferred embodiment of the method according to the invention for producing neral in pure or enriched form, in which, in addition to the features specified under FIG. 1, including the side take-off (f), the side take-off points (n) and (o) are provided.

The method for the distillative separation of geranial- and neral-containing substance mixtures that is to be carried out preferably according to the invention is carried out continuously. Consequently, the neral and geranial comprising substance mixtures to be used as starting material are continuously fed to the dividing wall column or to the interconnection of two distillation columns in the form of a thermal coupling, and the products (fractions) and/or by-products obtained according to the invention are discharged continuously.

Usually connected downstream of the column is a further condenser, the working temperature of which is 10 to 40 K, preferably 20 to 30 K, below the working temperature of the top condenser of the dividing wall column. With the aid of this, a majority of the low boilers still present in the top stream (k) can be precipitated.

Dividing wall columns can also be replaced by in each case two thermally coupled columns. This is favorable particularly when the columns are already present or the columns are to be operated at different pressures. In the case of thermally coupled columns, it may be advantageous to partially or completely evaporate the bottom stream of the first column in an additional evaporator and then to feed it to the second column. This preevaporation is particularly appropriate when the bottom stream from the first column comprises relatively large amounts of medium boilers. In this case, the preevaporation can take place at a relatively low temperature level and the evaporator in the second column can be deburdened. Furthermore, as a result of this measure, the stripping section of the second column can be significantly deburdened. The preevaporated stream can be fed here to the second column in biphasic form or in the form of two separate streams.

Moreover, both in the case of dividing wall columns and also in the case of thermally coupled columns, it may be advantageous to subject the feed stream to a preevaporation and then to feed it to the column in biphasic form or in the form of two streams. This preevaporation is appropriate particularly when the feed stream comprises relatively large amounts of low boilers. As a result of the preevaporation, the stripping section of the column can be significantly deburdened.

Dividing wall columns and thermally coupled columns can be designed either as packed columns with random packings or structured packings, or as tray columns. In the method according to the invention for producing neral in pure or enriched form, preference is given to using packed columns. In this respect, structured sheet metal or fabric packings with a specific surface area of about 100 to 750 $m^2/m^3$, preferably about 350 to 500 $m^2/m^3$, are particularly suitable.

If, as in the case of the present invention, particularly high requirements are placed on the purities of the products, it is favorable to equip the dividing wall with thermal insulation. A description of the various options for thermal insulation of the dividing wall can be found in EP-A 0 640 367. A double-wall design with a narrow gas space in between is particularly favorable.

For the control of dividing wall columns and thermally coupled columns, various control strategies have been described. Descriptions can be found in U.S. Pat. No. 4,230,533; DE 35 22 234; EP 0 780 147; Process Engineering 2 (1993) 33-34 and Ind. Eng. Chem. Res. 34 (1995), 2094-2103.

In the case of separation of multisubstance mixtures into low-boiling, medium-boiling and high-boiling fractions, there usually exist specifications regarding the maximum permissible fraction of low boilers and high boilers in the medium-boiling fraction. Here, either individual components which are critical for the separating problem, so-called key components, or the sum of several key components, are specified. These key components within the context of this optional step of the present invention are geranial as high-boiling secondary component, and isocitral or a mixture of isomeric isocitrals as low-boiling secondary component.

Compliance with the specification for the high boilers components in the medium-boiling fraction can be regulated, for example, via the division ratio of the liquid at the upper end of the dividing wall. Here, the division ratio of the liquid at the upper end of the dividing wall is preferably adjusted such that the concentration of the key components for the high-boiling fraction in the liquid at the upper end of the dividing wall constitutes 10 to 80%, preferably 30 to 50%, of the value which is to be achieved in the side take-off product. The liquid division is preferably adjusted to the effect that more liquid is fed to the feed section in the case of higher contents of key components in the high-boiling fraction, and less in the case of lower contents of key components in the high-boiling fraction.

Accordingly, the specification for the low boilers in the medium-boiling fraction can be regulated by the heating output. Here, for example, the heating output in the evaporator is adjusted such that the concentration of key components in the low-boiling fraction in the liquid at the lower end of the dividing wall constitutes 10 to 80, preferably 30 to 50%, of the value which is to be achieved in the side take-off product. The heating output is preferably adjusted to the effect that the heating output is increased in the case of a higher content of key components in the low-boiling fraction, and the heating output is reduced in the case of a lower content of key components in the low-boiling fraction.

To compensate for disturbances in the feed amount or the feed concentration, it has moreover proven advantageous, through a corresponding control mechanism (e.g. by means of control specifications in the process control system), to ensure that the quantitative streams of the liquids which to the column sections (2), i.e. the rectifying section of the feed section, and (5), i.e. the stripping section of the removal section, cannot drop below 30% of their normal value.

For the removal and division of the liquids at the upper end of the dividing wall and at the side removal point(s), both internal collecting spaces and also those arranged outside the column are suitable for the liquid, these assuming the function of a pump reservoir or providing for a sufficiently high static liquid level, which enable controlled further feeding of liquid by means of adjustment elements, for example valves. When using packed columns, the liquid is first captured in collectors and passed from there into an internal or external collecting space.

Instead of a dividing wall column—which is preferred for a new-build as regards investment costs—it is also possible to interconnect two distillation columns in a type of thermal coupling such that they correspond to a dividing wall column in terms of the energy requirement. They can be a useful alternative to dividing wall columns where existing columns are available. The appropriate forms of the interconnection can be selected depending on the number of plates in the existing columns.

If, within the context of this embodiment of step 0), to be carried out if desired, for separating geranial- and neral-containing substance mixtures, two distillation columns are used in an interconnection in the form of a thermal coupling, it has proven to be advantageous to equip both distillation columns coupled thermally in this way each with its own evaporator and condenser. In addition, the two thermally coupled columns can be operated at different pressures and only liquids can be conveyed in the connecting streams between the two columns. Within the context of a preferred embodiment, the bottom stream from the first column is partially or completely evaporated in an additional evaporator and then passed to the second column in biphasic form or in the form of one gaseous stream and one liquid stream.

Within the context of a particularly preferred embodiment, the separating method preferred according to the invention in accordance with optional step 0) is carried out in a plant as shown diagrammatically in FIG. 1. The preferred embodiment is notable for the fact that a dividing wall column (TK) is used which has a dividing wall (T) in the longitudinal direction of the column to form an upper common column region (1), a lower common column region (6), a feed section (2, 4) with rectifying section (2) and stripping section (4), and a removal section (3, 5) with stripping section (3) and rectifying section (5).

According to the invention, the neral and geranial comprising substance mixture (a) serving as feed material is preferably fed into the middle section of the feed section (2, 4), the neral, in pure or enriched form, is obtained as side take-off (f) from the middle region of the removal section (3, 5), and one or more low-boiling fractions are removed from the upper common column region (1) and one or more high-boiling fractions from the lower common column region (6).

The feed stream (a) can be introduced into the column (TK) via a preheater (VH) as a liquid (b), gaseous (c) or partially liquid and gaseous stream. The top stream of the column is completely or partially condensed in the condenser (K). In the case of partial condensation (dephlegmator operation), the offgas stream (k) from the top condenser (K) usually still comprises notable amounts of condensable low boilers, which can then be precipitated in a postcondenser operated at low temperature.

The top product precipitated in the condenser (K) can be buffered in the distillate container (DB) and fed back to the column as column return stream (i) via the return pump (RP). If required, a distillate fraction (j) can also be obtained therefrom. In the case of integration of the condenser into the top of the column, it is possible to dispense with the distillate container (DB) and the return pump (RP).

The bottom stream is advantageously fed to the bottom evaporator (SV) via the circulation pump (UP), which is preferably designed as a falling film evaporator. The bottoms discharge (g) of the column (TK) can also be removed from this pumped circulation stream.

The neral product of value in pure or enriched form is preferably removed as liquid side take-off, stream (f), from the removal section of the dividing wall column (TK). It is also possible, if required, to remove the product of value stream (f) as a gaseous take-off, although usually a further condenser is then required.

The upper common subregion (1) of the column usually has 5 to 50%, the rectifying section (2) of the feed section of the column 5 to 50%, the stripping section (4) of the feed section of the column 2 to 50%, the stripping section (2) of the removal section of the column 5 to 50%, the rectifying section (5) of the removal section 2 to 50%, and the common lower section (6) of the column 5 to 50%, of the total number of theoretical plates of the column, where the percentages selected add up to 100%.

Preferably, the upper common subregion (1) of the column has 10 to 25%, the rectifying section (2) of the feed section of the column 15 to 30%, the stripping section (4) of the feed section of the column 5 to 20%, the stripping section (3) of the removal section of the column 15 to 30%, the rectifying section (5) of the removal section 5 to 20%, and the common lower section (6) of the column 10 to 25%, of the total number of theoretical plates of the column, where the percentages selected add up to 100%.

The sum of the number of theoretical plates of subregions (2) and (4) in the feed section is preferably 80 to 110%, particularly preferably 95 to 105%, of the sum of the number of plates of subregions (3) and (5) in the removal section.

Advantageously, the feed point and the side take-off point, with regard to the position of the theoretical plates, are arranged at different heights in the column, by virtue of the feed point being arranged 1 to 50, preferably 30 to 45, theoretical plates higher or lower than the side take-off point.

It has moreover proven to be advantageous when the subregion of the column which is divided by the dividing wall and consists of the subregions (2), (3), (4) and (5) or sections thereof is equipped with structured packings or random packings (for example fabric packings such as Montz A3-500, Sulzer BX or CY). Furthermore, it has proven to be advantageous when the dividing wall in these subregions is thermally insulating in design.

The vapor stream at the lower end of the dividing wall can be adjusted through the selection and/or dimensioning of the separating internals and/or the incorporation of devices which generate a pressure drop, for example of restrictors, such that the ratio of the vapor stream in the feed section to that of the removal section is 0.8 to 1.2, preferably 0.9 to 1.1.

The liquid effluxing from the upper common subregion (1) of the column is advantageously collected in a collecting space arranged in the column or outside the column and is divided in a targeted manner by a fixed setting or control system at the upper end of the dividing wall such that the ratio of the liquid stream to the feed section to that to the removal section is 0.1 to 2.0 in the case of a predominantly liquid feed, and 1.0 to 2 in the case of a gaseous feed. Here, the liquid feed is preferred according to the invention.

The liquid effluxing from the upper common subregion (1) to the feed section can be conveyed via a pump or introduced under quantitative control via a static feed height of at least 1 m, preferably via a cascade control system in conjunction with the liquid level control system of the collecting space. The control system is preferably set such that the amount of liquid introduced to the feed section cannot fall below 30% of the desired normal value. Moreover, the division of the liquid effluxing from the subregion (3) in the removal section of the column to the side take-off and to the subregion (5) in the removal section of the column is advantageously adjusted by means of a control system such that the amount of liquid introduced to the subregion (5) cannot fall below a level of 30% of the desired normal value. The normal values here are advantageously assumed to be twice to four times the feed amount of geranial/neral mixture.

The dividing wall column to be used preferably within the context of optional step 0) preferably has, at the upper and lower ends of the dividing wall, sampling options from which samples can be taken in liquid or gaseous form from the column, continuously or at time intervals, and can be investigated with regard to their composition, preferably by gas chromatography.

The division ratio of the liquid at the upper end of the dividing wall is preferably adjusted such that the concentration of those components of the high-boiling fraction for which a particular concentration limit is to be achieved in the side take-off (specifically geranial) in the liquid at the upper end of the dividing wall constitutes 10 to 80%, preferably 30 to 50%, of the value which is to be achieved in the side take-off product. The liquid division should preferably be adjusted to the effect that more liquid is passed to the feed section in the case of higher contents of components of the high-boiling fraction, and less in the case of lower contents of components of the high-boiling fraction.

The heating output in the evaporator (SV) is preferably adjusted such that the concentration of those components of the low-boiling fraction for which a particular concentration limit is to be achieved in the side take-off (specifically isocitrals) at the lower end of the dividing wall constitutes 10 to 80%, preferably 30 to 50%, of the value which is to be achieved in the side take-off product. The heating output is advantageously adjusted to the effect that the heating output is increased in the case of a higher content of components of the low-boiling fraction, and the heating output is reduced in the case of a lower content of components of the low-boiling fraction.

The distillate removal, i.e. the removal of the low-boiling by-products, preferably takes place in a temperature-controlled manner. The control temperature used is advantageously a measurement site in the subregion (1) of the column which is arranged 3 to 8, preferably 4 to 6, theoretical plates below the upper end of the column.

Removal of the bottom product preferably takes place in a quantitatively controlled manner, preferably as a function of the feed amount.

The removal of the neral obtained as side product in pure or enriched form preferably takes place in a level-controlled manner, the control parameter used preferably being the liquid level in the column bottom.

The feed stream (a) is preferably partially or completely preevaporated and fed to the column in biphasic form or in the form of one gaseous and one liquid stream.

Within the context of a preferred embodiment, a dividing wall column is used, the dividing wall of which is not welded into the column but is configured in the form of loosely placed and adequately sealed subsegments.

The liquid division in the individual subregions of the column can preferably be adjusted nonuniformly in a targeted manner, in which case the liquid is added to an increased extent in the wall region, especially in subregions (2) and (5), and is added to a reduced extent in the wall region in subregions (3) and (4).

The division ratio of the returning liquid between removal side and feed side of the dividing wall is preferably about 1:1 to about 3:1, preferably about 1:1 to about 1.5:1.

The position of the dividing wall in the individual subregions of the column can advantageously be adjusted such that the cross sections of feed and removal sections have different areas.

A particularly preferred embodiment of the method, to be carried out preferably within the context of the method according to the invention according to optional step 0), for producing pure or enriched neral is notable for the fact that at least one low-boiling fraction is obtained as a liquid or gaseous, preferably as a liquid, side take-off (n) in the upper section (1) of the column, preferably 4 to 10 theoretical plates below the column top (see FIG. 2). In this case, it is expedient to divide the upper column section (1) into two sections ((1a) and (1b)). Between these sections, the liquid effluxing from section (1a) can be captured by a suitable collector and be distributed again on the underlying section (1b) (see FIG. 2). It is possible to remove a fraction with a low content of low boilers and neral which comprises in particular isomeric citrals from the collector.

This isocitral-rich by-product fraction accessible via the additional side take-off (n) can be suitably reused, for example it can be subjected to a far-reaching hydrogenation or to a partial hydrogenation to give tetrahydrogeraniol, as a result of which it is possible to avoid waste products and/or by-products that require disposal.

Within the context of one embodiment that is particularly preferred according to the invention, the optional step 0) therefore relates to a continuous method for producing neral of the formula (I) in pure or enriched form through distillative removal of neral from substance mixtures comprising neral and geranial of the formula (II)

where the distillative removal is carried out in a dividing wall column (TK) which has a dividing wall (T) in the longitudinal direction of the column to form an upper common column region (1), a lower common column region (6), a feed section (2, 4) with rectifying section (2) and stripping section (4), and a removal section (3, 5) with stripping section (3) and rectifying section (5), having 80 to 200 theoretical plates and a plurality, preferably 2 to 4, particularly preferably 2 or 3, side take-off points at an absolute operating pressure of from 5 to 200 mbar and where neral in pure or enriched form is obtained as side take-off (f) from the middle region of the removal section (3, 5) and a low-boiling fraction (n) is obtained as a liquid or gaseous, preferably as a liquid, side take-off from the upper common column region (1).

A further preferred embodiment of the separation method that can be used according to the invention is notable for the fact that at least one high-boiling fraction is obtained as gaseous side take-off (O) in the lower common subregion of the column (6), preferably 1 to 5 theoretical plates above the column bottom (see FIG. 2). As a result, a geranial-rich product with a particularly low content of high boilers can be obtained. In this case, it may be expedient to divide the lower column section (6) into two sections (6a and 6b). Between these sections, the liquid effluxing from the section (6a) can be captured by a suitable collector and be distributed again on the underlying section (6b) (see FIG. 2), and also the gas stream for the side take-off can be removed.

The bottom evaporator (SV) used for the dividing wall column can advantageously be a thin film apparatus, for example a falling film evaporator.

The top condenser (K) can be configured for example as a plate apparatus and be integrated into the column jacket.

The neral in pure or enriched form accessible by the described distillative separation method according to optional step 0) is obtained continuously via the side take-off, or in the case where further side take-offs are provided, via the middle side take-off (f) and, within the context of a preferred embodiment, has a neral content of more than 98% by weight, preferably of from 98.5 to 99.5% by weight, a geranial content of less than 0.3% by weight and a content of other isomers (citral isomers of the formulae (IV), (V) and (VI)) of less than 1% by weight (in each case based on the total amount of the resulting mixture), if appropriate alongside small amounts of further impurities.

If an upper side take-off (n) as described above is provided, a by-product mixture can be obtained there which usually has a neral content of less than 80% by weight, a geranial content of less than 0.1% by weight and a content of other isomers, in particular of the citral isomers of the formulae (IV), (V) and/or (VI) of more than 20% by weight, preferably of more than 30% by weight. In addition, in a lower side take-off (O), provided if desired, exactly as in the bottom fraction (g), a product mixture with a neral content of less than 20% by weight and a geranial content of more than 70% by weight can be obtained. The top fraction (j) usually has a neral content of less than 30% by weight. The low-boiling fraction (k) separated off therefrom usually has a neral content of less than 5% by weight besides isocitrals as main components.

A further aspect of the optional substep 0) of the present invention relates to the use of a dividing wall column as described above or of an interconnection of two distillation columns in the form of a thermal coupling, preferably of a dividing wall column having 80 to 200 theoretical plates and one or more side take-off points for continuously producing neral of the formula (I) in pure or enriched form by distillative removal of neral from substance mixtures comprising neral and geranial of the formula (II) or the use thereof for isolating neral. A further aspect of the optional substep 0) of the present invention relates to a dividing wall column as described above or an interconnection of two distillation columns in the form of a thermal coupling, preferably a dividing wall column having 80 to 200 theoretical plates and one or more side take-off points, which is suitable for continuously producing neral of the formula (I) in pure or enriched form by distillative removal of neral from substance mixtures comprising neral and geranial of the formula (II).

Step a): Catalytic Hydrogenation of Neral and/or Geranial to Give Citronellal

According to stage a) of the method according to the invention for producing menthol, a catalytic hydrogenation of neral and/or geranial is carried out to give citronellal of the formula (XIII)

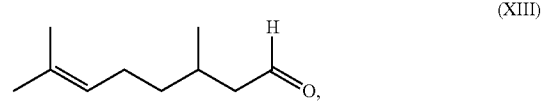

(XIII)

preferably a catalytic hydrogenation of neral as described above or of neral produced as described above by distillative separation of geranial- and neral-containing substance mixtures, in pure or enriched form.

Catalytic hydrogenation methods of the specified starting materials to give racemic citronellal are known to the person skilled in the art and described, for example, in W. J. Houlihan, J. Org. Chem. 1958, 23, 689-690; R. Giannandrea, P. Mastrorilli, G. Zaccaria, C. F. Nobile, J. Mol. Cat. A. 1996, 109, 113-117; U. K. Singh, M. A. Vannice, J. Catal. 2000, 191, 165-180; WO 2004/007414 A1. In addition, an enantioselective method for producing optically active citronellal by hydrogenation of geranial or neral in the presence of a rhodium-phosphine catalyst is known from EP 0 000 315.

An improved method, and one which can be used preferably within the context of the present invention, for producing optically active carbonyl compounds by asymmetric hydrogenation of α,β-unsaturated carbonyl compounds in the presence of optically active transition metal catalysts that are soluble in the reaction mixture and which have at least one carbon monoxide ligand is known from WO 2006/040096, to which reference is hereby made in its entirety and which, including all of the preferred embodiments, should be considered part of the present disclosure. The catalysts to be used advantageously in the process, or suitable ligands for the production thereof, can also be found in the cited disclosure. Said hydrogenation method is notable for the fact that the catalyst is pretreated with a carbon monoxide and hydrogen comprising gas mixture and/or the asymmetric hydrogenation is carried out in the presence of carbon monoxide additionally fed to the reaction mixture.

Within the context of one particularly preferred embodiment of the hydrogenation method which can be carried out preferably within the context of step a), neral or geranial, preferably neral, in turn preferably that which comprises up to about 5 mol %, particularly preferably up to about 2 mol % of the respective other double-bond isomer, is reacted to give optically active citronellal.

To form the catalyst to be used in the course of the asymmetric catalytic hydrogenation of step a) that is preferably to be carried out, preference is given to using a compound of rhodium that is soluble in the reaction mixture, in particular Rh(OAc)$_3$, [Rh(cod)Cl]$_2$, Rh(CO)$_2$acac, [Rh(cod)OH]$_2$, [Rh(cod)OMe]$_2$, Rh$_4$(CO)$_{12}$ or Rh$_6$(CO)$_{16}$ and as chiral ligands (R,R)-chiraphos of the formula (R-VII) or (S,S)-chiraphos of the formula (S-VII)

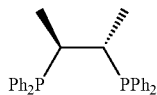

(S-VII)

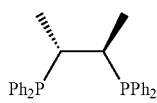

(R-VII)

((2R,3R)-(+)-2,3-bis(diphenylphosphino)butane or (2S,3S)-(−)-2,3-bis(diphenyl-phosphino)butane) in the molar ratio from about 1:1 to about 1:4. In one particularly preferred embodiment of the method according to the invention, neral which comprises up to about 5 mol %, preferably up to about 2 mol % of geranial, is reacted in the presence of Rh(OAc)$_3$, [Rh(cod)Cl]$_2$, Rh(CO)$_2$acac, [Rh(cod)OH]$_2$, [Rh(cod)OMe]$_2$, Rh$_4$(CO)$_{12}$ or Rh$_6$(CO)$_{16}$ and (R,R)-chiraphos to give D-citronellal of the formula (R-XIII)

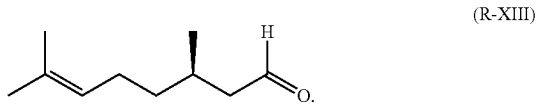

(R-XIII)

Besides the specified chiral ligands, for carrying out the hydrogenation method preferably to be carried out within the course of step a) of the method according to the invention, also the ligands specified in WO 2006/040096 are suitable, in particular the ligands of the general formulae (VIII), (IX) and (X), preferably those of the general formula (VIII),

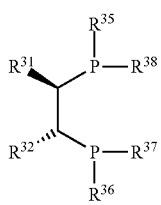

(VIII)

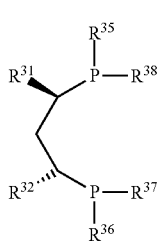

(IX)

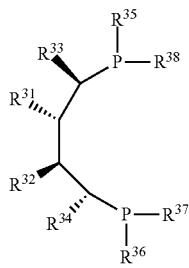

(X)

in which

R$^{31}$, R$^{32}$: in each case independently of one another are an unbranched, branched or cyclic alkyl radical having 1 to 20 carbon atoms which can optionally carry one or more, generally 1 to about 4, ethylenic double bonds and/or one or more, generally 1 to about 4, identical or different substituents selected from the group of the substituents OR$^{39}$, NR$^{40}$R$^{41}$, halogen, C$_6$-C$_{10}$-aryl and C$_3$-C$_9$-hetaryl, and R$^{31}$ and R$^{32}$ together can form a 4 to 20-membered ring which can include one or more, generally 1 or 2, O atoms, and R$^{33}$, R$^{34}$: in each case independently of one another are hydrogen or straight-chain or branched C$_1$- to C$_4$-alkyl and R$^{35}$, R$^{36}$, R$^{37}$, R$^{38}$: are in each case C$_6$- to C$_{10}$-aryl, which can optionally carry one or more, generally 1 to 8, preferably 1 to 4, substituents selected from the group of the substituents C$_1$- to C$_4$-alkyl, C$_6$- to C$_{10}$-aryl, C$_1$- to C$_4$-alkoxy and amino, and R$^{39}$, R$^{40}$, R$^{41}$: in each case independently of one another are hydrogen, C$_1$-C$_4$-alkyl, C$_6$-C$_{10}$-aryl, C$_7$-C$_{12}$-aralkyl or C$_7$-C$_{12}$-alkylaryl, where R$^{40}$, R$^{41}$: together can also be an alkylene chain having 2 to 5 carbon atoms, which may be interrupted by N or O.

Here, the specified radicals can be attributed the meanings specified by way of example in WO 2006/040096.

Preferably, the catalyst to be used for the hydrogenation is preformed under the conditions given in WO 2006/040096 and then the asymmetric hydrogenation is carried out in the presence of hydrogen which comprises about 600 to about 3000 ppm of carbon monoxide. Within the context of the preferred embodiment, the addition of solvents is advantageously dispensed with and the specified reactions are carried out in the substrate to be reacted and/or the product and optionally in high-boiling by-products as dissolution medium. Particularly preferably, the continuous reaction procedure is with reutilization and/or recycle of the homogeneous catalyst stabilized according to the invention.

A further preferred embodiment within the context of the hydrogenation according to step a) of the method according to the invention for producing menthol relates to a method for producing optically active carbonyl compounds by asymmetric hydrogenation of α,β-unsaturated carbonyl compounds in the presence of optically active transition metal catalysts which are soluble in the reaction mixture and which have at least one carbon monoxide ligand, where, for producing the optically active catalyst having at least one carbon monoxide ligand that is to be used in each case, a catalyst precursor is pretreated with a gas mixture comprising carbon monoxide and hydrogen and the asymmetric hydrogenation is carried out in the presence of carbon monoxide additionally fed to the reaction mixture, wherein i) the pretreatment of the catalyst precursor is carried out with a gas mixture comprising 20 to 90% by volume of carbon monoxide, 10 to 80% by volume of hydrogen and 0 to 5% by volume of further gases, where the specified volume fractions add up to 100% by volume, at a pressure of from 5 to 100 bar, ii) excess carbon monoxide is separated off from the catalyst obtained in this way prior to it being used in the asymmetric hydrogenation and iii) the asymmetric hydrogenation is carried out in the presence of hydrogen with a carbon monoxide content of from 100 to 1200 ppm.

Following the preforming, which can be carried out as described in WO 2006/040096, of the transition metal catalyst to be used or of its precursor according to step i), excess carbon monoxide is separated off from the catalyst obtained by preforming or pretreatment with said gas mixture, according to step ii) of the preferred hydrogenation method, prior to the catalyst being used in the asymmetric hydrogenation.

The term excess carbon monoxide is to be understood here as meaning the carbon monoxide which is present in gaseous or dissolved form in the reaction mixture obtained according to step i) by preforming and is not bonded to the transition metal catalyst or its precursor. Accordingly, the excess carbon monoxide not bonded to the catalyst is removed at least largely, i.e. to an extent such that any residual amounts of dissolved carbon monoxide do not become troublesome in the subsequent hydrogenation. This is usually ensured if about 90%, preferably about 95% or more, of the carbon monoxide used for the preforming is separated off according to step ii) of this preferred embodiment of the hydrogenation method. Preferably, according to step ii), excess carbon monoxide is removed completely from the catalyst obtained by preforming.

Removal of the excess carbon monoxide from the catalyst obtained according to step i) or from the reaction mixture comprising the catalyst according to step ii) of the preferred embodiment of the hydrogenation method can take place in various ways. Preferably, the catalyst or the mixture comprising the catalyst obtained by preforming according to step i) is decompressed to a pressure of up to about 5 bar (absolute), preferably to a pressure in the range from about 1 bar to about 5 bar, such that gaseous, nonbonded carbon monoxide escapes from the product of the preforming.

The aforementioned decompression of the preformed catalyst can take place, for example, using a high-pressure separator, as is known per se to the person skilled in the art. Separators of this type, in which the liquid is in the continuous phase, are described, for example, in: Perry's Chemical Engineers' Handbook, 1997, 7th edition, McGraw-Hill, pp. 14.95 and 14.96; prevention of possible drop entrainment is described on pages 14.87 to 14.90. Decompression of the preformed catalyst can take place in one stage or two stages until reaching the desired pressure in the range from 1 bar to about 5 bar, during which the temperature usually drops to 10 to 40° C.

Alternatively, removal of excess carbon monoxide according to step ii) can also be achieved by so-called stripping of the catalyst or of the mixture comprising the catalyst using a gas, advantageously using a gas which is inert under the reaction conditions. The term stripping is understood by the person skilled in the art here as meaning the introduction of a gas into the catalyst or the reaction mixture comprising the catalyst, as described, for example, in W. R. A. Vauck, H. A. Müller, Grundoperationen chemischer Verfahrenstechnik [Basic operations of chemical process technology], Deutscher Verlag für Grundstoffchemie Leipzig, Stuttgart, 10$^{th}$ edition, 1984, page 800. Suitable inert gases which may be mentioned here by way of example are: hydrogen, helium, neon, argon, xenon, nitrogen and/or $CO_2$, preferably hydrogen, nitrogen, argon.

After the preforming according to step i) and the freeing of the catalyst from excess carbon monoxide according to step ii), according to step iii) of this preferred embodiment of the hydrogenation method that can be used according to the invention, the asymmetric hydrogenation of the selected substrate is carried out in the presence of hydrogen with a carbon monoxide content of from 100 to 1200 ppm.

The addition of additional carbon monoxide to the reaction mixture of the asymmetric hydrogenation can be carried out in various ways: for example, the carbon monoxide can be admixed, for example, with the hydrogen used for the asymmetric hydrogenation, or else metered directly into the reaction solution in gaseous form. A further option consists, for example, in adding to the reaction mixture compounds which readily liberate carbon monoxide, such as, for example, formates or oxalyl compounds.

The fraction of carbon monoxide in the hydrogen used is, within the context of one preferred embodiment of the method according to the invention, about 300 to 1000 ppm, particularly preferably 400 to 800 ppm.

The asymmetric hydrogenation described above is advantageously carried out at a pressure of from about 1 to about 300 bar, preferably from about 10 to about 100 bar, in particular at about 50 to about 100 bar and at a temperature of generally about 0° C. to about 100° C., preferably about 0° C. to about 30° C., in particular at about 10° C. to about 30° C.

The selection of the solvent to be used for carrying out the asymmetric hydrogenation is not critical. Suitable solvents are, for example, those specified for carrying out the preforming according to the invention. The asymmetric hydrogenation is particularly advantageously carried out in the same solvent as the optional preforming carried out beforehand.

Suitable reaction vessels for carrying out the asymmetric hydrogenation described above are in principle all those which permit reactions under the stated conditions, in particular within the stated pressure and temperature ranges, and are suitable for hydrogenation reactions, such as, for example, autoclaves, tubular reactors, bubble columns and more besides.

If the hydrogenation according to step iii) of the hydrogenation method preferred within the context of the method according to the invention is carried out using high-boiling, generally viscous solvents, as are described, for example, in WO 2006/040096 for use in the course of the pretreatment of the catalyst according to step i) of the method according to the invention (for example the specified solvents octadecanol, biphenyl ether, texanol, Marlotherm®, Oxoöl 9N) or if the hydrogenation is carried out without the additional use of solvents, but with accumulation of the high boilers which form as by-products to a small extent (such as, for example, dimers or trimers which are formed by reactions of the starting materials or products and subsequent secondary reactions), it may be advantageous to ensure good gas feed and good thorough mixing of gas phase and condensed phase. This is possible, for example, by carrying out the hydrogenation step of the method in a gas circulation reactor. Gas circulation reactors are known per se to the person skilled in the art and described, for example, in P. Trambouze, J.-P. Euzen, Chemical Reactors, Ed. Technip, 2004, pp. 280-283 and P. Zehner, R. Benfer, Chem. Eng. Sci. 1996, 51, 1735-1744 and also e.g. in EP 1 140 349.

When using a gas circulation reactor as specified above, it has proven to be particularly advantageous to introduce the gas or gas mixture to be used (hydrogen comprising the carbon monoxide) into the gas circulation reactor in parallel to the starting materials introduced into the reactor and/or the circulating reaction mixture or the catalyst by means of a single nozzle or a two-material nozzle. Here, the two-material nozzle is notable for the fact that liquid and gas to be introduced into the reactor pass through two separate tubes, one within the other, under pressure to the nozzle mouth, where they are combined with one another.

The hydrogenation method preferred according to the invention can be carried out successfully with and without the addition of tertiary amines. Preferably, the method according to the invention is carried out in the absence, i.e. without the addition of additional tertiary amines or in the presence of only catalytic amounts of additional tertiary amines. The amount of amine used can here be between 0.5 and 500 mol equivalents, based on the amount of metal used, but is preferably 1 to 100 mol equivalents, based on the amount of metal used. The choice of tertiary amine is not critical. Besides short-chain alkylamines, such as, for example, triethylamine, it is also possible to use long-chain alkylamines, such as, for example, tridodecylamine. Within the context of a preferred embodiment, the hydrogenation method according to the invention is carried out in the presence of a tertiary amine, preferably tridodecylamine, in an amount of from about 2 to 30 mol equivalents, preferably about 5 to 20 mol equivalents and particularly preferably 5 to 15 mol equivalents, based on the amount of transition metal used.

The asymmetric hydrogenation method to be carried out preferably according to the invention is notable for the fact that the homogeneous catalysts used are stabilized by the carbon monoxide additionally introduced into the reaction system, as a result of which, firstly, the service life of the catalysts is significantly increased and, secondly, the reusability of the homogeneous catalysts is facilitated.

Thus, for example, the resulting reaction product can be removed from the reaction mixture by methods known per se to the person skilled in the art, such as e.g. by distillation, for example by means of a fine film evaporator, Sambays or the like, and the catalyst which remains, if appropriate following repeated preforming as described above, can be used in the course of further reactions.

Accordingly, the hydrogenation method to be used preferably according to the invention in the course of step a) can be operated either discontinuously or semicontinuously and also continuously and is suitable in particular for reactions on an industrial scale. Preference is given to carrying out the method continuously.

The pretreatment of the catalyst precursor (preforming) according to step i) that is to be carried out in the course of the asymmetric hydrogenation preferred according to the invention and the actual asymmetric hydrogenation according to step iii) are advantageously carried out in separate reaction vessels. When transferring the preformed catalyst to the actual hydrogenation reactor, preferably the gas circulation reactor as described above, the excess carbon monoxide can then be removed from the catalyst, for example by releasing the pressure used for the preforming.

The hydrogenation can also take place in two or more, preferably in two or three, particularly preferably in two, hydrogenation reactors connected in series. Here, it is possible to use different types of reactors or similar reactor types. In one preferred embodiment, the asymmetric hydrogenation is carried out, for example, in a cascade of two gas circulation reactors, where one functions as main reactor and the second as postreactor. To transfer the reaction mixture from the main reactor to the postreactor it is possible to use here, for example, a pressure gradient to be adjusted as desired.

The racemic or optically active citronellal accessible in this way is usually produced in high yield and in particular high chemical and optical purity. Depending on the requirements placed on the chemical purity of the resulting citronellal to be further reacted in the course of further step b), preferably D-citronellal, it can be further purified by separation and/or purification methods known per se to the person skilled in the art, such as, for example, chromatographic or distillative methods. It has proven to be advantageous to further purify the resulting citronellal by distillation, it being possible in principle to use all distillation methods and equipment that appear to be suitable to the person skilled in the art, such as, for example, distillation columns (packed or unpacked), falling film evaporators, thin film evaporators and the like. Said methods can also be carried out together, i.e. in succession. Thus, a prepurification of the citronellal-containing product mixture obtained by the presented hydrogenation by means of a falling film evaporator and subsequent fine distillation of the citronellal has proven to be advantageous.

For the distillative purification and/or removal of the resulting optically active or racemic citronellal, preference is given to carrying out a distillation by means of a dividing wall column, as is disclosed, for example, in DE 103 30 934 A1. Using a dividing wall column with about 30 to about 100, preferably about 45 to about 85, theoretical plates, it is possible, upon suitable selection of pressure and temperature of the distillation, to usually isolate citronellal with high purity, often with a purity of 98% by weight and above, preferably of 99% by weight and above.

Step b): Cyclization of Citronellal to Give Isopulegol

According to step b) of the method according to the invention, a cyclization of citronellal which has been obtained by the above-described step a) by catalytic hydrogenation of substance mixtures comprising neral and/or geranial, to give isopulegol is carried out in the presence of an acidic catalyst.

The cyclization of citronellal to isopulegol under acidic conditions has been known for a long time. An overview of the available acidic or Lewis-acidic reagents or catalysts can be found, for example, under E. J. Lenardao, G. V. Botteselle, F. de Azambuja, G. Perin, R. G. Jacob Tetrahedron 2007, 63, 6671-6712.

A broad diversity of systems is known as customary catalysts and reagents, such as for example: silica gel or aluminum oxide or mixtures thereof, as disclosed e.g. in WO 2004/089299, zeolites, as described e.g. for the case of boron-containing zeolites in WO 2004/101480. Further customary acidic or Lewis-acidic catalysts are, for example, zinc bromide, as described e.g. in Synthesis 1978, 147-148 and in EP 1053974 A1 or else tungsten-containing acids as described in BR 2005002489 A.

Moreover, EP-A 1 225 163 describes the cyclization of citronellal to isopulegol in the presence of tris(2,6-diphenylphenol)aluminum catalysts. Tris(2,6-diphenylphenol)-aluminum is known in the literature and as catalyst for selective 1,4-functionalizations of $\alpha,\beta$-unsaturated carbonyl compounds and for specific Claisen rearrangements, for example in Angew. Chem. Int. Ed. 2004, 43, 994. The specified catalyst system is also suitable for use in the course of step b) of the method according to the invention.

WO 2007/039342 and WO 2007/039366 likewise disclose aluminum-containing homogeneous catalysts, specifically those which have one or more siloxide ligands on the aluminum. The disclosed aluminum-siloxide compounds are suitable as catalysts for intramolecular Prins reactions, including the cyclization of citronellal to isopulegol.

According to the invention, preference is given to carrying out the cyclization of citronellal to isopulegol according to step b) in the presence of an aluminum-containing catalyst, specifically in the presence of a Lewis-acidic aluminum-containing catalyst.

A method for the cyclization of citronellal to isopulegol that is particularly preferred within the context of step b) of the method according to the invention is described in WO 2006/092433, to which reference is hereby made in its entirety and the disclosure of which, including all preferences and embodiments, should be considered part of the present disclosure. The cited patent application discloses specific diarylphenoxyaluminum compounds which are obtainable by reacting a bis(diarylphenol) ligand of the formula (I)

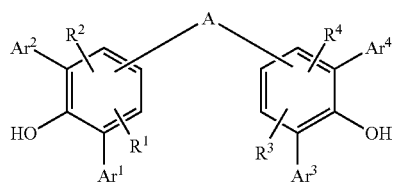

(I)

where

Ar$^1$, Ar$^2$, Ar$^3$, Ar$^4$ are identical or different and are in each case independently of one another an aryl radical having 6 to 15 carbon atoms or a heteroaryl radical having 2 to 15 carbon atoms which can optionally carry in each case 1 to 7 identical or different substituents selected from the group of the substituents C$_1$- to C$_6$-alkyl, C$_1$- to C$_6$-perfluoroalkyl, C$_1$- to C$_6$-alkoxy, C$_7$- to C$_{12}$-aralkyl, halogen, —SiR$^{5a}$R$^{6a}$R$^{7a}$, substituted or unsubstituted C$_6$- to C$_{10}$-aryl, —NR$^{8a}$R$^{9a}$, —SR$^{19a}$ and —NO$_2$, R$^1$, R$^2$, R$^3$, R$^4$ are identical or different and are in each case independently of one another hydrogen, C$_1$- to C$_6$-alkyl, C$_1$- to C$_6$-perfluoroalkyl, C$_1$- to C$_6$-alkoxy, C$_7$- to C$_{12}$-aralkyl, halogen, —SiR$^{5b}$R$^{6b}$R$^{7b}$, substituted or unsubstituted C$_6$- to C$_{10}$-aryl, —NR$^{8b}$R$^{9b}$, —SR$^{10b}$ and/or —NO$_2$, and R$^1$ or R$^2$ and/or R$^3$ or R$^4$, together with A, can form an aromatic or nonaromatic cycle, and A (1) is a straight-chain or branched and/or cyclic hydrocarbon radical having 1 to 25 carbon atoms which may be saturated or mono- or polyunsaturated and/or partially aromatic and can optionally have one or more identical or different heteroatoms selected from the group of the heteroatoms O, S and NR$^{11}$ and/or one or more identical or different functional groups selected from the group of the functional groups C(O), S(O) and S(O)$_2$, and can optionally carry one or more identical or different substituents selected from the group of the substituents C$_1$- to C$_6$-alkyl, C$_1$- to C$_6$-perfluoroalkyl, C$_1$- to C$_6$-alkoxy, C$_1$- to C$_{10}$-acyloxy, C$_7$- to C$_{12}$-aralkyl, halogen, —SiR$^{5c}$R$^{6c}$R$^{7c}$, substituted or unsubstituted C$_6$- to C$_{10}$-aryl, substituted or unsubstituted C$_2$- to C$_{10}$-hetaryl, —NR$^{8c}$R$^{9c}$, —SR$^{10c}$, —NO$_2$, C$_1$- to C$_{12}$-acyl and C$_1$- to C$_{10}$-carboxyl, or (2) is an aryl radical having 6 to 15 carbon atoms or a heteroaryl radical having 2 to 15 carbon atoms which can optionally carry in each case 1 to 5 substituents selected from the group of the substituents C$_1$- to C$_6$-alkyl, C$_1$- to C$_6$-perfluoroalkyl, C$_1$- to C$_6$-alkoxy, C$_7$- to C$_{12}$-aralkyl, halogen, —SiR$^{5d}$R$^{6d}$R$^{7d}$, substituted or unsubstituted C$_6$- to C$_{10}$-aryl, —NR$^{8d}$R$^{9d}$, SR$^{10d}$ and NO$_2$, or (3) is a functional group or a heteroatom selected from the group —O—, —S—, —N(R$^{11}$)—, —S(O)—, —C(O)—, —S(O)$_2$—, —P(R$^{11}$)—, —(R$^{11}$)P(O)— and —Si(R$^{12}$R$^{13}$), where the radicals R$^{5a}$, R$^{6a}$, R$^{7a}$, R$^{8a}$, R$^{9a}$, R$^{10a}$ to R$^{5d}$, R$^{6d}$, R$^{7d}$, R$^{8d}$, R$^{9d}$, R$^{10d}$ and R$^{11}$ to R$^{13}$ are in each case independently of one another C$_1$- to C$_6$-alkyl, C$_7$- to C$_{12}$-aralkyl and/or substituted or unsubstituted C$_6$- to C$_{10}$-aryl, and the radicals R$^{8a}$ and R$^{9a}$, R$^{8b}$ and R$^{9b}$, R$^{9c}$ and R$^{9b}$, R$^{8d}$ and R$^{9d}$ can independently of one another in each case together also form a cyclic hydrocarbon radical having 2 to 8 carbon atoms which can have one or more identical or different heteroatoms selected from the group O, S and NR$^{11a}$, and R$^{11a}$ can have the meanings given for R$^{11}$, with an aluminum compound of the formula (XIV)

$$(R^{14})_{3-p}AlH_p$$ (XIV), where

Al is aluminum and

R$^{14}$ is a branched or unbranched alkyl radical having 1 to 5 carbon atoms and p is 0 or an integer from 1 to 3, and/or with an aluminum compound of the formula (XV)

$$MAlH_4$$ (XV), where

Al is aluminum and

M is lithium, sodium or potassium.

The bis(diarylphenol) ligands of the formula (I) to be used for producing the diarylphenoxyaluminum compounds to be used preferably in the course of step b) of the method according to the invention have two phenol systems which are in each case substituted in both ortho positions relative to the phenolic hydroxy group by aromatics or heteroaromatics (Ar$^1$ to Ar$^4$) and are linked together via a structural element A and can optionally also carry further substituents (R$^1$ to R$^4$). The specified diarylphenoxyaluminum compounds are obtained as reaction products or product mixtures of the reaction of the aforementioned bis(diarylphenol) ligands of the formula (I) with the aluminum compounds (XIV) or (XV).

Diarylphenoxyaluminum compounds to be used preferably within the context of the method according to the invention are those which are obtainable by the aforementioned reaction of ligands of the general formulae (Ia)

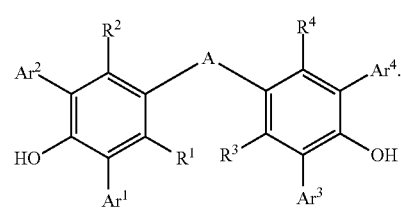

(Ia)

The ligands of the formula (Ia) likewise have two phenol systems which are in each case substituted in both ortho positions relative to the phenolic hydroxy group by aromatics or heteroaromatics ($Ar^1$ to $Ar^4$) and are linked together via a structural element A and can optionally also carry further substituents ($R^1$ to $R^4$), where the structural element A is linked to the two phenol systems in each case in the para position relative to the phenolic hydroxy group. Here, the radicals $Ar^1$, $Ar^2$, $Ar^3$, $Ar^4$, the radicals $R^1$, $R^2$, $R^3$, $R^4$ and the structural element A can be attributed the same meanings as specified above for formula (I).

Particularly preferred bis(diarylphenol) ligands for producing the diarylphenoxyaluminum compound to be used preferably according to the invention within the context of step b) are those which are obtainable by reacting ligands of the formulae ($Ia_1$), ($Ia_2$) or ($Ia_3$) as described in WO 2006/092433. A diarylphenoxyaluminum compound to be used in particular within the context of step b) of the method according to the invention is one which is obtainable by reacting a bis(diarylphenol) ligand of the formula (XI)

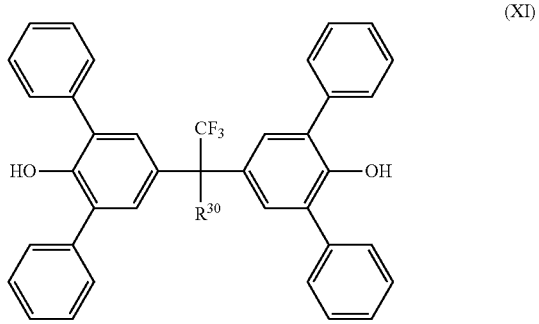

(XI)

where the radical $R^{30}$ is $C_1$- to $C_6$-alkyl or $C_1$- to $C_6$-perfluoroalkyl, with an aluminum compound of the formula (XIV) and/or (XV), preferably with trimethyl- and/or triethylaluminum and particularly preferably with triethylaluminum, as described in the aforementioned WO 2006/092433.

Here, $C_1$- to $C_6$-alkyl are to be understood as meaning straight-chain or branched alkyl radicals having 1 to 6 carbon atoms, such as, for example, methyl, ethyl, propyl, isopropyl, n-butyl, sec-butyl, tert-butyl, n-pentyl or n-hexyl, preferably methyl, ethyl, isopropyl.

The term $C_1$- to $C_6$-perfluoroalkyl is to be understood here as meaning alkyl radicals having 1 to 6 carbon atoms in which all of the hydrogen atoms are substituted by fluorine atoms, such as, for example, trifluoromethyl, pentafluoroethyl, heptafluoropropyl, heptafluoroisopropyl, nonafluorobutyl, preferably trifluoromethyl.

A diarylphenoxyaluminum compound that is particularly preferred within the context of the present invention is one which is obtainable by reacting the bis(diarylphenol) ligand of the formula ($Ia_2$-3)

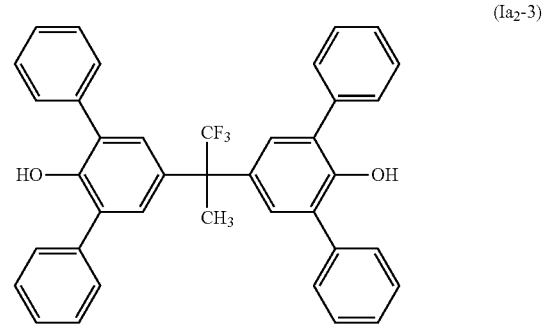 [SMILES: CC(c1cc(-c2ccccc2)c(O)c(-c2ccccc2)c1)(c1cc(-c2ccccc2)c(O)c(-c2ccccc2)c1)C(F)(F)F]

($Ia_2$-3)

with trimethyl- or triethylaluminum, preferably triethylaluminum, under the conditions stated in the aforementioned WO 2006/092433, including all of the preferred embodiments and combinations thereof described therein.

A further bis(diarylphenol) ligand preferred according to the invention is the ligand of the formula ($Ia_2$-1) having two trifluoromethyl groups

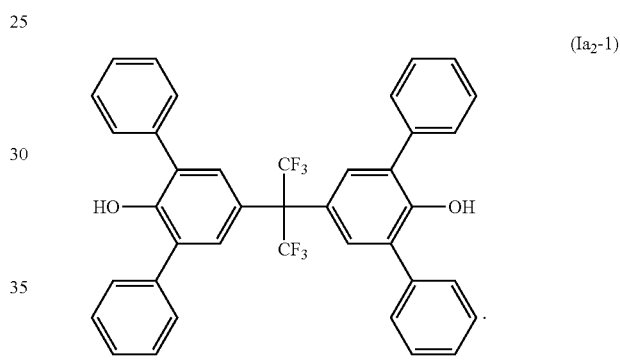

($Ia_2$-1)

Within the context of a preferred embodiment, step b) to be carried out according to the invention is carried out in the form of a method for producing isopulegol of the formula (XII)

(XII)

comprising the cyclization of citronellal of the formula (XIII)

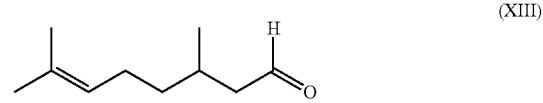

(XIII)

in the presence of a catalyst which is obtainable by reacting a bis(diarylphenol) ligand of the formula (I)

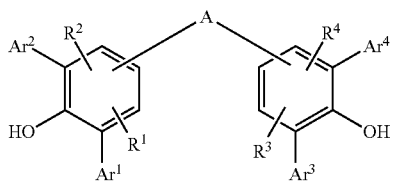 (I)

where
$Ar^1$, $Ar^2$, $Ar^3$, $Ar^4$, $R^1$, $R^2$, $R^3$, $R^4$ and A have the meanings given above for formula (I) with an aluminum compound of the formula (XIV)

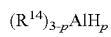 (XIV), where
Al is aluminum and
$R^{14}$ is a branched or unbranched alkyl radical having 1 to 5 carbon atoms and
p is 0 or an integer from 1 to 3,
and/or
with an aluminum compound of the formula (XV)

 (XV), where
Al is aluminum and
M is lithium, sodium or potassium.

The details for carrying out this preferred embodiment of the cyclization method to be carried out according to the invention can be found in the already cited WO 2006/092433, to which reference is made in its entirety also in this respect.

The bis(diarylphenoxy)aluminum compounds used preferably according to the invention for the cyclization according to step b) are obtained, for example, by reacting the bis(diarylphenol) ligands of the formulae (I) or (Ia) described above with an aluminum compound of the formula (XIV)

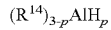 (XIV).

Here, $R^{14}$ is a branched or unbranched alkyl radical having 1 to 5 carbon atoms, such as, for example, methyl, ethyl, propyl, isopropyl, butyl, isobutyl, pentyl, isopentyl or neopentyl. The index p is 0 or an integer from 1 to 3. Preferably, the index p is 1 or 0, particularly preferably 0. Preferred compounds of the formula (XIV) are, for example, trimethylaluminum, triethylaluminum, diisobutylaluminum hydride, particularly preferably trimethylaluminum and triethylaluminum.

Alternatively to this, the bis(diarylphenoxy)aluminum compounds to be used preferably according to the invention are also obtained by reacting the bis(diarylphenol) ligands of the formulae (I) or (Ia) as described above with an aluminum compound of the formula (XV)

 (XV), where M is lithium, sodium or potassium. Consequently, of suitability for producing the bis(diarylphenoxy)aluminum compounds to be used preferably according to the invention by reacting the bis(diarylphenol) ligands of the formulae (I) or (Ia) as described above are also lithium aluminum hydride, sodium aluminum hydride and potassium aluminum hydride, and also mixtures thereof. Moreover, mixtures of said compounds of the formulae (XIV) and (XV) are also suitable for producing bis(diarylphenoxy)aluminum compounds used according to the invention by reaction with the bis(diarylphenol) ligands of the formulae (I) or (Ia) as described above.

The reaction is advantageously carried out such that one of the bis(diarylphenol) ligands of the formulae (I) or (Ia), particularly preferably the ligand of the formula (Ia$_2$-3), as described above is brought into contact with a compound of the formula (XIV) or (XV). Advantageously, the reaction is carried out in an inert organic solvent, such as, for example, toluene, cyclohexane, dichloromethane, xylene, ethylbenzene, chlorobenzene, tetrahydrofuran, diethyl ether, methyl tert-butyl ether, ethyl acetate, pentane, hexane, dichloroethane, dimethylformamide (DMF), dimethyl sulfoxide (DMSO) and the like, with the use of predried or anhydrous solvents being considered to be particularly advantageous. Usually, the reaction takes place at temperatures in the range from about −100° C. to about 100° C., preferably at about −50° C. to about 50° C., particularly preferably at about −30° C. to about 30° C.

During the production of the bis(diarylphenoxy)aluminum compounds to be used preferably according to the invention in the course of step b), the phenolic hydroxy groups of the bis(diarylphenol) ligands of the formulae (I) or (Ia) react with the compound(s) of the formulae (XIV) and (XV). Theoretically, each aluminum atom can react with 1 to 3 phenolic hydroxy groups. On account of the steric properties or requirements of the bis(diarylphenol) ligands of the formulae (I) or (Ia) used, the result here may be the formation of relatively high molecular weight structures, such as linear structures or networks.

Advantageously here, the molar ratio of the bis(diarylphenol) ligands of the formulae (I) or (Ia) to the compounds of the formula (XIV) and/or (XV) used is chosen such that the amount of compounds of the formulae (XIV) and/or (XV) that have not completely reacted is as low as possible. Preferably, said ratio is selected such that, after bringing the bis(diarylphenol) ligands of the formulae (I) or (Ia) into contact with the compound(s) of the formulae (XIV) and (XV), unreacted compound of the formula (XIV) and/or (XV) is no longer present. Taking into consideration the economic aspect, it is advisable to keep the excess of the ligands of the formulae (I) or (Ia) used low. Particularly preferably, bis(diarylphenol) ligands of the formulae (I) or (Ia) and the compounds of the formulae (XIV) and/or (XV) are used in a molar ratio of from about 4:1 to about 1:1, very particularly preferably from about 3:1 to about 1.5:1 and most preferably in the molar ratio of about 1.5:1.

For producing the bis(diarylphenoxy)aluminum compounds to be used preferably according to the invention, within the context of one preferred embodiment of the present invention, the procedure involves introducing as initial charge, depending on the solubility, an approximately 0.001 to about 1 molar solution of the selected ligand of the formula (I) or (Ia) in a suitable organic solvent, for example toluene, at a temperature of from about −10 to about 30° C., and adding an aluminum compound of the formula (XIV) and/or (XV), preferably in the form of a solution, for example a solution of trimethyl- or triethylaluminum in toluene.

The reaction between the ligands of the formula (I) or (Ia) used and the aluminum compounds of the formulae (XIV) and/or (XV) generally takes place rapidly and is in most cases complete after about 10 min to about 2 h, often after about 1 h, depending on the reaction conditions chosen. When using less reactive reactants, it may be advantageous to increase the temperature of the reaction mixture for a short time.

Depending on the chosen reaction conditions, in particular with regard to the solubility of the ligands of the formula (I) or (Ia) to be reacted and the aluminum compound of the formula (XIV) and/or (XV) in the selected solvents, the concentrations and also the reaction temperatures, the bis(diarylphenoxy)aluminum compounds to be used preferably according to the invention in the course of step b) are obtained in the form of a solid, a suspension or a solution in the solvent or solvent mixture used. The resulting bis(diarylphenoxy)aluminum compounds used preferably according to the invention can be further used or separated off in the form obtained in each case and be freed from the solvents used.

Isolation can take place here by methods which are known to the person skilled in the art and appear to be advantageous. Preferably, the isolation, storage and/or further treatment of the bis(diarylphenoxy)aluminum compounds to be used preferably according to the invention is carried out with extensive exclusion of oxygen and moisture.

For carrying out the method for producing isopulegol preferred according to the invention, the procedure advantageously involves firstly providing a solution of the bis(diarylphenoxy)aluminum compounds used according to the invention in a suitable solvent, as described above. According to the invention, the racemic or nonracemic citronellal to be cyclized is then added to this solution. The citronellal can be added here as such or in the form of a solution, advantageously in one of the aforementioned suitable solvents. Within the context of one preferred embodiment of the method according to the invention, a solution of the selected ligand of the formulae (I) or (Ia) in toluene is firstly prepared and then, advantageously with stirring, the selected aluminum compound of the formula (XIV) and/or (XV), preferably trimethyl- or triethylaluminum in toluenic solution is added.

Of suitability in principle as starting material for carrying out the cyclization method preferred according to the invention is citronellal, which may be prepared by any method. However, within the context of the present invention, preference is given to using optically active citronellal as can be obtained according to above-described step a) by asymmetric hydrogenation of geranial and/or neral. Preference is given to using citronellal which has a purity of from about 90 to about 99.9% by weight, particularly preferably from about 95 to about 99.9% by weight.

The addition of the citronellal to be cyclized advantageously takes place at temperatures in the range from about −40° C. to about 40° C., preferably in the range from about −20° C. to about 20° C. For this, the prepared solution of the bis(diarylphenoxy)-aluminum compound used according to the invention is advantageously cooled to a temperature within this range, e.g. to a temperature in the range from −10° C. to 10° C., and precooled citronellal or a precooled solution of citronellal is added.

The addition of the citronellal or of the solution thereof can be performed such that either the total amount is added in one go or it is added to the prepared catalyst solution in portions or else continuously. Suitable solvents are in turn the aforementioned solvents, in particular toluene. Preference is given to using the citronellal to be cyclized as it is, i.e. without the further addition of solvents. When using a solvent, the total amount of solvent (for catalyst production and for carrying out the cyclization reaction) is advantageously selected such that the volume-based ratio of citronellal to be reacted to the solvent is about 2:1 to about 1:20, preferably from about 1.5:1 to about 1:10.

The quantitative ratio between the citronellal to be reacted and the amount used of the bis(diarylphenoxy)aluminum compound used according to the invention is determined by the amount of the compounds of the formula (I) or (Ia) and of the formula (XIV) and/or (XV) used for the production thereof, i.e. by the quantitative ratio of ligand used to aluminum compound of the formula (XIV) and/or (XV) used.

According to the invention, the amount of citronellal to be reacted relative to the amount of aluminum compound of the formula (XIV) and/or (XV) used is chosen such that the molar ratio is about 5:1 to about 1000:1, preferably about 10:1 to about 500:1, particularly preferably about 50:1 to about 200:1.

Irrespective of this, the ratio between ligand of the formula (I) or (Ia) used and the aluminum compound of the formula (XIV) and/or (XV) used can be varied within the limits specified above for producing the bis(diarylphenoxy)aluminum compound to be used preferably according to the invention.

Depending on the choice of reaction partners and reaction conditions, the cyclization of citronallal to isopulegol generally takes place quickly and is usually largely completed after about 0.5 to about 10 h, often after about 5 h. The reaction progress can be monitored easily by methods known per se to the person skilled in the art, for example by chromatographic, specifically gas-chromatographic, methods or else HPLC methods.

Within the context of one preferred embodiment of the cyclization method preferred according to the invention, the cyclization of citronellal to isopulegol is carried out in the presence of an auxiliary (iv), for example an acid, preferably an organic acid. By way of example, organic acids that can be used advantageously are: acetic acid, propionic acid, benzoic acid, toluenesulfonic acid, methanesulfonic acid, preferably acetic acid. Said acids are advantageously used in an amount of from about 0.5 to about 10% by weight, based on the amount of citronellal to be reacted. Advantageously, they are added to the reaction mixture together with the citronellal, e.g. in the form of a mixture.

In one particularly preferred embodiment, the method preferred according to the invention for producing isopulegol by cyclization of citronellal is carried out in the presence of at least one auxiliary (iv) which is selected from carboxylic anhydrides, aldehydes, ketones and vinyl ethers.

The auxiliaries (iv) of said substance classes can be used in each case individually or in the form of mixtures with one another. In the case of mixtures, preference is given to using those which consist of compounds of one substance class. Particularly preferably, individual compounds are used. Using said compounds, as described below, it is generally possible to largely suppress the formation of undesired by-products.

Within the context of one preferred embodiment, the above-described cyclization of citronellal is carried out in the presence of bis(diarylphenoxy)aluminum compounds in the presence of a carboxylic anhydride of the formula (XVI)

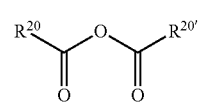 (XVI)

where the radicals $R^{20}$ and $R^{20'}$ may be identical or different, preferably identical, and are a branched or unbranched $C_1$-$C_{12}$-alkyl radical or $C_7$-$C_{12}$-aralkyl radical or a $C_6$-$C_{10}$-aryl radical, where the specified radicals may in each case have one or more, generally 1 to about 3, identical or different substituents selected from the group $OR^{10e}$, $SR^{10f}$, $NR^{8e}R^{9e}$ and halogen and where $R^{20}$ and $R^{20'}$ can together also form a 5- to 8-membered ring which can have one or more ethylenic double bonds and one or more identical or different heteroatoms selected from the group O, S and $NR^{11b}$ and where $R^{10e}$, $R^{10f}$, $R^{8e}$, $R^{9e}$ and $R^{11b}$ can have the meanings given above for $R^{11}$.

Within the context of a further preferred embodiment, the cyclization of citronellal is carried out in the presence of an aldehyde (different from citonellal) of the formula (XVII)

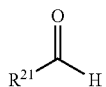

(XVII)

where the radical $R^{21}$ is a branched or unbranched $C_1$-$C_{12}$-alkyl radical or $C_7$-$C_{12}$-aralkyl radical or a $C_6$-$C_{10}$-aryl radical, where the specified radicals can in each case have one or more, preferably 1 to 3, identical or different substituents selected from the group $OR^{10e}$, $SR^{10f}$, $NR^{8e}R^{9e}$ and halogen and where $R^{10e}$, $R^{10f}$, $R^{8e}$ and $R^{9e}$ can have the meanings given above for $R^{11}$.

Within the context of a further preferred embodiment, cyclization of citronellal is carried out in the presence of a ketone of the formula (XVIII)

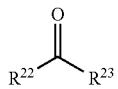

(XVIII)

where the radicals $R^{22}$ and $R^{23}$ may in each case be identical or different and are a branched or unbranched $C_1$-$C_{12}$-alkyl radical or $C_7$-$C_{12}$-aralkyl radical or a $C_6$-$C_{10}$-aryl radical or a $C_1$-$C_6$-alkoxycarbonyl radical, where said radicals can in each case have one or more, preferably 1 to 3, identical or different, substituents selected from the group $OR^{10e}$, $SR^{10f}$, $NR^{8e}R^{9e}$ and halogen, and where $R^{22}$ and $R^{23}$ together can also form a 5- to 8-membered ring which can have one or more ethylenic double bonds and one or more identical or different heteroatoms selected from the group O, S, $NR^{11b}$ and where $R^{10e}$, $R^{10f}$, $R^{8e}$, $R^{9e}$ and $R^{11b}$ can have the meanings given above for $R^{11}$.

Alternatively to the aforementioned carbonyl compounds, it is also possible to use vinyl ethers of the general formula (XIX)

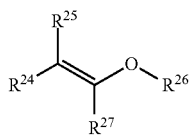

(XIX)

in the course of the cyclization method preferred according to the invention, where the radicals $R^{24}$, $R^{25}$, $R^{26}$ and $R^{27}$, in each case independently of one another, may in each case be identical or different and are a branched or unbranched $C_1$-$C_{12}$-alkyl radical or $C_7$-$C_{12}$-aralkyl radical or a $C_6$-$C_{10}$-aryl radical, where said radicals can in each case have one or more, preferably 1 to 3, identical or different substituents selected from oxo, $OR^{10e}$, $SR^{10f}$, $NR^{8e}R^{9e}$ and halogen and where $R^{25}$ and $R^{26}$ together can also form a 5- to 8-membered ring which can have one or more ethylenic double bonds and one or more, usually 1 or 2, identical or different heteroatoms selected from the group O, S, $NR^{11b}$, and where $R^{10e}$, $R^{10f}$, $R^{8e}$, $R^{9e}$ and $R^{11b}$ can have the meanings given above for $R^{11}$.

$C_1$-$C_{12}$-Alkyl here is $C_1$-$C_6$-alkyl as described above and, moreover, for example heptyl, octyl, nonyl, decyl, undecyl or dodecyl. In cases where two alkyl radicals together form a ring, alkyl radicals are also to be understood as meaning alkylenyl radicals. $C_7$-$C_{12}$-Aralkyl radicals and $C_6$-$C_{10}$-aryl radicals can, for example, be attributed the meanings specified above. By way of example, $C_1$-$C_6$-alkoxycarbonyl radicals that may be mentioned are: methoxycarbonyl, ethoxycarbonyl, propoxycarbonyl and isopropoxycarbonyl, preferably methoxycarbonyl and ethoxycarbonyl.

Within the context of one preferred embodiment of the cyclization method preferred according to the invention, the cyclization of citronellal is carried out in the presence of a carboxylic anhydride of the formula (XVI), where the radicals $R^{20}$ and $R^{20'}$ are identical and are a branched or unbranched $C_1$-$C_{12}$-alkyl radical or $C_7$-$C_{12}$-aralkyl radical or a $C_6$-$C_{10}$-aryl radical, and where $R^{20}$ and $R^{20'}$ can together also form a 5- to 8-membered ring which can have one or more ethylenic double bonds and one or more identical or different heteroatoms selected from the group $OR^{10e}$, $SR^{10f}$, $NR^{11b}$, and $R^{10e}$, $R^{10f}$ and $R^{11b}$, independently of one another, can have the meanings given above for $R^{11}$.

Particular preference is given to using those carboxylic anhydrides in which the radicals $R^{20}$ and $R^{20'}$ are identical and are a branched or unbranched $C_1$-$C_{12}$-alkyl radical or a $C_6$-$C_{10}$-aryl radical. By way of example, carboxylic anhydrides to be used particularly preferably according to the invention are: acetic anhydride, propionic anhydride, pivalic anhydride and benzoic anhydride.

Aldehydes of the formula (XVII) which can likewise preferably be used according to the invention are, for example, acetaldehyde, propionaldehyde and chloral (trichloroacetaldehyde).

If the cyclization of citronellal preferred according to the invention is carried out within the context of a further preferred embodiment in the presence of a ketone of the formula (XVIII), those ketones with an activated, i.e. low-electron, carbonyl function are used advantageously. By way of example, mention may be made of the following ketones, which are suitable to a particular degree for use in the course of the method according to the invention: 1,1,1-trifluoroacetone, 1,1,1-trifluoroacetophenone, hexafluoroacetone, methyl pyruvate and ethyl pyruvate.

Examples of vinyl ethers of the formula (XIX) which can likewise be used preferably according to the invention within the context of this embodiment of step b) are: methyl vinyl ether, ethyl vinyl ether, isobutyl vinyl ether and 3,4-dihydro-2H-pyran.

Said compound classes can be used with equal good success within the context of this preferred embodiment of the method according to the invention. As regards practical aspects, such as, for example, higher reaction rate, the use of aldehydes and/or low-electron ketones has proven to be advantageous.

The amount of carboxylic anhydride, aldehyde, ketone and/or vinyl ether to be used preferably can be varied within wide limits and is governed by the type of substance used and the degree of purity or the presence of impurities still not identified more specifically. Usually, said compounds or mixtures thereof are used in an amount of from about 0.01 mol % to about 5 mol %, preferably from about 0.1 mol % to about 2 mol %, based on the amount of citronellal used.

The type and method of the reaction procedure, for example the configuration of reactors or the sequence of the addition of individual reaction partners are not subject to any particular requirements provided a reaction procedure with extensive exclusion of oxygen and water is ensured.

To carry out this preferred embodiment of the cyclization method to be carried out according to the invention in the course of step b), the procedure advantageously involves firstly preparing a solution of the bis(diarylphenoxy)aluminum compound to be used according to the invention in a suitable solvent as described above. A mixture of the racemic or nonracemic, preferably nonracemic, i.e. optically active citronellal with the selected carboxylic anhydride, the aldehyde, the activated ketone and/or the vinyl ether is then preferably added to this solution. Alternatively to this, it is also possible, for example, to firstly admix the solution of the bis(diarylphenoxy)aluminum compound to be used preferably according to the invention with the carboxylic anhydride, the aldehyde, the ketone and/or the vinyl ether optionally selected in each case and then to add the racemic or optically active citronellal to be cyclized.

It has proven to be advantageous to meter in the citronellal or the mixture of citronellal with the selected compound to the catalyst solution or the reaction mixture within a period of from about 30 min to about 6 h, preferably within about 2 h to about 4 h. The citronellal can be added here as such or in the form of a solution, advantageously in one of the aforementioned suitable solvents. In the course of a further preferred embodiment of the method preferred according to the invention, firstly a solution of the selected ligand of the formulae (I) or (Ia) in toluene is prepared and then, expediently with stirring, the selected aluminum compound of the formula (XIV) and/or (XV), preferably trimethyl- or triethylaluminum in toluenic solution, is added.

Within the context of this embodiment, the addition of the citronellal to be cyclized or of the mixture of citronellal with the selected carboxylic anhydride, aldehyde, activated ketone and/or the vinyl ether takes place advantageously at temperatures in the range from about −40° C. to about 40° C., preferably in the range from about −20° C. to about 20° C. For this, the prepared solution or suspension of the bis(diarylphenoxy)aluminum compound to be used preferably according to the invention is advantageously cooled to a temperature within this range, e.g. to a temperature in the range from −10° C. to 10° C., and the further reactants are added in precooled form.

The addition of the mixture of citronellal and of the selected further compound can be performed such that either the total amount of citronellal is added all at once or it is added to the prepared catalyst solution in portions or else continuously. Suitable solvents are in turn preferably the aforementioned solvents, in particular toluene. Preferably, the citronellal to be cyclized is used in the form of a mixture with the selected carboxylic anhydride, aldehyde, activated ketone and/or vinyl ether without the further addition of solvents. When using a solvent, the total amount of solvent is advantageously selected such that the volume-based ratio of citronellal to be reacted relative to the solvent is about 1:1 to about 1:20, preferably from about 1:1 to about 1:10.

It has been found that some of the catalyst complex is usually deactivated during the reaction in the course of the preferred cyclization method described above. This is attributable inter alia to ligand exchange processes between the bis(diarylphenol) ligands of the formula used in each case of the bis(diarylphenoxy)aluminum compounds used and the isopulegol that is formed by cyclization. The deactivated form of the catalyst is soluble in the reaction mixture, depending on the choice of solvents used, usually in contrast to the active polymeric catalyst.

In one preferred embodiment, simple physical separation methods (e.g. filtration or centrifugation of the still active catalyst) can be used to separate off the deactivated part of the catalyst together with the remaining reaction mixture. The retained, still active part of the catalyst can, if desired, be supplemented with fresh catalyst and be reused without noteworthy loss in activity, preferably in the course of a further cyclization reaction according to the invention of citronellal to isopulegol.

Alternatively, the amount of catalyst used can be selected such that the total catalyst complex used in the course of and/or after the end of the cyclization reaction according to the invention is deactivated and thus soluble, which can be seen from a clear reaction mixture. In this connection, it is advantageously notable that in this case, on account of the above-described ligand exchange processes, the bis(diarylphenol) ligand of the formula (I) used in each case is liberated without carrying out hydrolysis separately.

Surprisingly, it has been found that isopulegol can be distilled off in high purities from the aluminum-containing reaction products of the cyclization of citronellal without prior hydrolysis of the diarylphenoxyaluminum compounds used in each case as catalyst (if appropriate following distillative removal of a solvent used and/or additionally used auxiliaries). In this connection, as a rule no recognizable undesired or troublesome by-products are formed in the distillation bottom. In a specific embodiment, the addition of a suitable, inert, high-boiling solvent takes place before or during distillative separation in step I). This then gives a solution of the ligand of the formula (I) in the heated high boiler used in each case in the distillation bottom.

The cyclization method to be carried out preferably according to the invention in the course of step b) is equally suitable, as already mentioned, for the cyclization of racemic and/or also nonracemic, i.e. optically active citronellal to racemic and nonracemic isopulegol.

Consequently, in one preferred embodiment, the method according to the invention serves to produce optically active isopulegol by cyclization of active citronellal.

In particular, the cyclization method preferred according to the invention serves for producing L-(−)-ispulegol starting from D-(+)-citronellal.

Said bis(diarylphenol) ligands can, following use of the diarylphenoxyaluminum compounds obtainable therefrom as catalysts for the cyclization of citronellal to isopulegol, on account of their good crystallization behavior, be recovered in a particularly advantageous manner discontinuously or preferably semicontinuously or completely continuously and thus render themselves useful for further reactions. A particularly preferred embodiment of the cyclization to be carried out preferably according to the invention in the course of step b) therefore comprises a method of working up an aluminum-containing reaction product from the production of isopulegol by cyclization of citronellal, comprising i) isopulegol,
ii) at least one ligand of the formula (I),

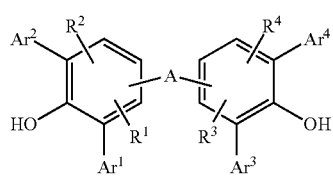

where the radicals $Ar^1$, $Ar^2$, $Ar^3$, $Ar^4$, $R^1$, $R^2$, $R^3$, $R^4$ and A can have the meanings given above,
in free and/or complex-bonded form,
in which I) the aluminum-containing reaction product is subjected to distillative separation to give an isopulegol-enriched top product and an isopulegol-depleted bottom product,
II) the isopulegol-depleted bottom product is brought into close contact with an aqueous base to give an aluminum-containing aqueous phase and an organic phase comprising the majority of the ligands of the formula (I),
III) the ligand of the formula (I) is separated off from the organic phase.

In one preferred embodiment of the cyclization preferred according to the invention and to be carried out in the course of step b), in the presence of the aforementioned diarylphenoxyaluminum compounds work-up to be carried out preferably, the ligand of the formula (I) is separated off from the organic phase by crystallization.

The bis(diarylphenol) ligands of the formula (I) obtained by the cyclization method preferred according to the invention can usually be reacted without further purification steps in the course of a new batch with the corresponding aluminum compounds of the formulae (XIV) or (XV), as defined below, to give the reactive catalyst complex, with no or no noteworthy weakening in the reactivity being established for catalyst complexes recreated in such a way.

Within the context of the cyclization to be carried out preferably according to the invention in the course of step b) in the presence of the specified diarylphenoxyaluminum compounds and their preferred work-up, the term "ligand in free or complex-bonded form" comprises both the free form of the ligand and also all conceivable forms which can be converted to the free form under the process conditions. By way of example, mention may be made here of alcoholates of the ligand which are converted to the free form of the ligand by basic hydrolysis.

Within the context of the present invention, the expression "aqueous base" generally comprises aqueous solutions, the pH of which is greater than 7. In particular, these are aqueous solutions of alkali metal and alkaline earth metal hydroxides, specifically aqueous solutions of KOH and NaOH.

Within the context of the cyclization or work-up method preferred according to the invention, the expression "aluminum-containing reaction product" describes a reaction product which comprises at least one compound which comprises aluminum in ionic form, covalent form or complex-bonded form. These are compounds of aluminum as result under the conditions of the method according to the invention from the compounds of the formula $(R^{14})_{3-p}AlH_p$ (XIV) or $MAlH_4$ (XV) used in the cyclization of citronellal, as defined above.

Within the context of the present cyclization or work-up method preferred according to the invention, the expression "majority" should be understood as meaning a percentage fraction of the total amount of a compound present which is greater than 50%, preferably greater than 80% and particularly preferably greater than 90%.

Step I):

In step I) of the work-up method preferred according to the invention, the aluminum-containing reaction product from the production of isopulegol by cyclization of citronellal is subjected to a distillative separation to give an isopulegol-enriched top product and an isopulegol-depleted bottom product.

In one specific embodiment, in step I), a solvent which has a higher boiling point than isopulegol is used. Consequently, undesired thermal stressing of the bottom ingredients can be avoided. In particular, the ligands of the formula (I) present therein are not present in a form free from solvent during the removal of the isopulegol. The higher-boiling solvent can be added to the aluminum-containing reaction product before and/or during the distillative separation. Preferably, a higher-boiling solvent is used, the boiling point of which is above the boiling point of isopulegol under the conditions of the distillation. Preferably, the boiling point of the introduced solvent under the conditions of the distillation is at least 5° C., preferably at least 10° C. and in particular at least 20° C., above the boiling point of the isopulegol.

Preferred higher-boiling solvents which have such a boiling point are, for example, hydrocarbons, such as phenylcyclohexane, benzyltoluene, dibenzyltoluene, 1-methylnaphthalene and tridecane, 1-decanol, 1,2-propylene carbonate, ethers, such as diethylene glycol dibutyl ether, tetraethylene glycol dimethyl ether and dibenzyl ether, and also technical-grade mixtures of these solvents. Particular preference is given to mixtures which comprise phenylcyclohexane as main constituent.

When using at least one higher-boiling solvent, the isopulegol-depleted bottom product obtained in step I) is an organic phase comprising the higher-boiling solvent, the majority of the ligands of the formula (I), and optionally at least one aluminum-containing compound.

Preferably, the distillative removal of isopulegol in step I) takes place at a bottom temperature of preferably at most 250° C., preferably at most 150° C. and particularly preferably at most 100° C. The lower bottom temperature is generally noncritical and is generally at least 0° C., preferably at least 20° C. In order to maintain these maximum temperatures, the distillation can, if desired, be carried out under a suitable vacuum.

The pressure in step I) of the work-up method preferred according to the invention is, irrespective of the particular embodiment, generally in a range from 0.1 to 1500 mbar, preferably in a range from 1 to 500 mbar and particularly preferably in a range from 5 to 100 mbar.

Irrespective of the composition of the aluminum-containing reaction product from the cyclization of citronellal and of the use of a higher-boiling solvent, the distillative removal of the isopulegol can take place continuously or discontinuously, preferably continuously. In one suitable procedure, the higher-boiling solvent is added to the reaction product from the cyclization of citronellal before the distillative removal and, in the course of the distillation, the amount of high-boiling solvent present in the bottom is subsequently kept constant.

For the distillative removal in step I), the customary equipment known to the person skilled in the art can be used (see e.g. Sattler, Thermische Trennverfahren [Thermal separation methods], $2^{nd}$ edition, 1995, Weinheim, p. 135ff; Perry's Chemical Engineers Handbook, $7^{th}$ edition, 1997, New York, Section 13). These include distillation columns which can be provided with packings, internals etc. The distillation columns used can comprise separating internals, such as separating trays, e.g. perforated trays, bubble-cap trays or valve trays, structured packings, e.g. sheet metal or fabric packings, or random beds of packings. The number of plates required in the column(s) used and the reflux ratio depend substantially on the purity requirements and the relative boiling point of the constituents of the aluminum-containing reaction product from the production of isopulegol by cyclization of citronellal and of the higher-boiling solvent, it being possible for the person skilled in the art to determine the specific design and operating data by known methods. The distillative separation can take place e.g. in one or more distillation columns coupled together.

Likewise suitable for the distillative separation in step I) of the work-up method preferred according to the invention are customary evaporators, preferably evaporators with forced circulation, particularly preferably falling film evaporators.

Depending on any additional components which may be present in the aluminum-containing reaction product from the cyclization of citronellal, the composition of the top product obtained during the distillative separation may make it necessary in some cases to subject this top product to a further work-up step.

In one specific embodiment of the method, preferred according to the invention in the course of step b), for working-up an aluminum-containing reaction product from the production of isopulegol by cyclization of citronellal, the reaction product additionally comprises a lower-boiling solvent (iii).

Within the context of the present invention, the expression "lower-boiling solvent (iii)" refers to the boiling point of the isopulegol. Of particular suitability for this are those solvents or solvent mixtures which, under the conditions of the distillative separation, have a boiling point which is at least 5° C., preferably 10° C. and in particular 20° C., below that of the isopulegol under the particular conditions.

Within the context of the preferred work-up method, preferred solvents with such a boiling point are inert organic solvents or mixtures thereof, such as, for example, aromatic solvents, e.g. toluene, ethylbenzene or xylene, halogenated solvents, e.g. dichloromethane, dichloroethane or chlorobenzene, aliphatic solvents, e.g. pentane, hexane or cyclohexane, ethers, e.g. tetrahydrofuran, diethyl ether, methyl tert-butyl ether, esters, e.g. ethyl acetate, or dimethylformamide (DMF), dimethyl sulfoxide (DMSO) and the like. It is particularly preferably toluene.

If the aluminum-containing reaction product to be worked up comprises such a lower-boiling solvent, then this is removed at least partially from the reaction product in one suitable embodiment prior to the distillative removal of the isopulegol. Removal of the lower-boiling solvent preferably likewise takes place by distillation. Depending on the boiling point of the lower-boiling solvent, it is possible to use the customary aforementioned distillation devices.

In one further suitable embodiment, the distillative separation of the aluminum-containing reaction product takes place in step I) to give an isopulegol-enriched top product which simultaneously comprises at least some, preferably the majority, of the lower-boiling solvent. In this case, the top product can be subjected to a further separation, preferably likewise by distillation.

The separated-off lower-boiling solvent is advantageously returned to the cyclization of the citronellal, where it is used as solvent. In this way, the work-up method preferred according to the invention requires—apart from supplements which are required as a result of unavoidable losses—the mere single provision of an amount of the lower-boiling solvent.

In one specific embodiment of the method to be carried out preferably according to the invention for the cyclization of citronellal to isopulegol and also for the work-up of an aluminum-containing reaction product from the production of isopulegol by cyclization of citronellal, the reaction product additionally comprises an auxiliary (iv).

Within the context of step b) of the present invention, the term "auxiliary (iv)" refers to compounds which are added during the cyclization of citronellal in order to suppress undesired secondary reactions. Preference is given to the auxiliaries (iv) selected from organic acids, carboxylic anhydrides, aldehydes (with the exception of citronellal), ketones and vinyl ethers, as are described in WO 2006/092433, to which reference is made in its entirety also in this regard, and also as are described above.

In a further specific embodiment of the present cyclization or work-up method preferred according to the invention, the auxiliaries (iv), as described above, are selected from carboxylic anhydrides, aldehydes (with the exception of citronellal), ketones and vinyl ethers.

The auxiliaries (iv) of the specified substance classes can in each case be present individually or in the form of mixtures in the reaction product to be worked up. Preferred mixtures are those which consist of compounds of one substance class. Particularly preferably, the reaction product comprises a single auxiliary.

Preferably, the auxiliaries (iv) present in the reaction product from the cyclization of citronellal are likewise at least partially removed and returned as far as possible to the cyclization of citronellal.

If, under the conditions of the distillation, the auxiliaries (iv) have a boiling point which is below, or only slightly above, i.e. less than 30° C., the boiling point of the isopulegol, these can be recovered from the fully reacted mixture by distillation to a large extent and to a degree to which they have not optionally themselves been reacted. Depending on the boiling point of the auxiliary, the customary aforementioned distillation devices can be used.

If, under the conditions of the distillation, the auxiliaries (iv) have a boiling point which is significantly above, i.e. at least 30° C., the boiling point of the isopulegol, these remain in the bottom product and are, if necessary, removed in step II) of the work-up method preferred according to the invention, if their physical properties permit this.

In a further suitable embodiment, the distillative separation of the reaction product takes place in step I) to give an isopulegol-enriched top product which simultaneously comprises at least some, preferably the majority, of the auxiliary (iv). If necessary, this main product can comprise a lower-boiling solvent, as detailed previously. In this case, the top product can be subjected to a further separation, preferably likewise by distillation. The separated-off auxiliary (iv), optionally together with the lower-boiling solvent, is returned advantageously to the cyclization of the citronellal, where it is used e.g. for suppressing undesired secondary reactions. In this way, the work-up method preferred according to the invention—with the exception of supplements which are required as a result of unavoidable losses—requires the mere single provision of an amount of the auxiliary (iv).

The isopulegol separation, the introduction of the higher-boiling solvent and optionally the removal of low boilers, i.e. the removal of optionally present solvents and volatile auxiliaries from the cyclization of citronellal can be combined in different ways:

In one suitable embodiment, a so-called dividing wall column is used for the distillation, i.e. feed point and a side take-off are located on opposite sides of a dividing wall which extends over a section of the longitudinal expansion of the column. Distillation columns of this type which comprise a dividing wall are known per se to the person skilled in the art. If side take-off and feed are located in the region of the dividing wall, a system analogous to a Brugma or Petlyuk system is the result. Distillations of this type using dividing wall columns are described in DE-A-33 02 525 and EP-A-0 804 951, to which reference is hereby made in their entirety. In this case, the top product drawn off can for example be a fraction enriched in low-boiling components, and the side take-off can be a stream comprising the majority of isopulegol. The higher-boiling solvent is supplied below the feed point, preferably into the bottom of the column and just above the bottom. A solution of the majority of the ligand of the formula (I) in the higher-boiling solvent is produced as bottom product.

In one alternative embodiment, coupled columns are used for the distillation. This embodiment may be advantageous if the reaction product of the cyclization of citronellal comprises a solvent and/or a volatile auxiliary, as explained in more detail below.

In this case, mixtures of isopulegol and solvents with a lower or slightly higher boiling point and/or auxiliary (iv) can form the top product of the first column and, in the second column, can be subjected to a separation to give a stream comprising at least the majority of the isopulegol and an isopulegol-depleted stream comprising the lower-boiling solvents and/or auxiliaries of the cyclization.

Streams which comprise lower-boiling solvents (iii) and auxiliary (iv) of the cyclization preferred according to the invention can generally be returned to the cyclization without further separation.

The ligands of the formula (I) are produced, optionally in the form of their complexes or other derivatives, as bottom product of the first column.

Step II):

In step II) of the work-up method to be carried out preferably according to the invention in the course of step b), the isopulegol-depleted bottom product is brought into close contact with an aqueous base to give an aluminum-containing aqueous phase and an organic phase comprising the majority of the ligands of the formula (I). Preferred aqueous bases are those specified above.

Besides the ligand of the formula (I) in free or complex-bonded form, the isopulegol-depleted bottom product obtained in step I) can comprise at least one further difficultly volatile component. These include e.g. higher-boiling solvents added in step I), the reaction products of the aluminum-containing compounds used preferably for the cyclization of citronellal to isopulegol, and any auxiliaries (iv) not separated off in step I). Since aluminum-containing components and/or the auxiliaries (iv) accumulate especially in the case of a continuous method and have an adverse effect specifically on the yield and purity of the separation in step III), it is advantageous to remove these compounds as completely as possible. This is true specifically for the aluminum-containing compounds.

The bringing into contact in step II) preferably takes place by extraction. The number of extraction stages is preferably in a range from 1 to 20 stages.

The extractants used are the aforementioned aqueous bases. Consequently, these expressions are used synonymously within the'context of the present invention.

For the extraction, the isopulegol-depleted bottom product from step I) is brought into close contact with an aqueous base. Separating the phases gives a phase comprising the majority of the ligand of the formula (I) and an aqueous phase enriched in aluminum-containing compounds. The aqueous phase is then removed. The bringing into contact can take place continuously or discontinuously.

For the discontinuous procedure, the isopulegol-depleted bottom product from step I) and the aqueous extractant are brought into contact in a suitable vessel with mechanical agitation, e.g. stirring, the mixture is left to rest for phase separation and one of the phases is removed by expediently drawing off the denser phase at the bottom of the vessel.

A plurality of discontinuous separating operations can be carried out in succession in a type of cascade, in which case the phase separated off from the aqueous phase and comprising the majority of the ligand of the formula (I) is in each case brought into contact with a fresh portion of the aqueous extractant and/or the aqueous extractant is conveyed countercurrently.

Preferably, the extraction takes place continuously. For the continuous procedure of the extraction, the aqueous extractant and the stream of isopulegol-depleted bottom product from step I) are continuously passed to suitable apparatuses in an analogous manner to the discontinuous variant. At the same time, a discharge of the phase comprising the majority of the ligand of the formula (I) and a discharge of the aqueous phase enriched in aluminum-containing compounds are continuously removed from the apparatus in which the separation of the phases takes place.

The extraction takes place in at least one stage, e.g. in a mixer/separator combination. Suitable mixers are either dynamic or static mixers. An extraction in two or more stages takes place, for example, in a plurality of mixer/separators or extraction columns.

In one suitable embodiment, at least one coalescing device is used for improving the phase separation. This is preferably selected from coalescing filters, electrocoalescers and combinations thereof. When using mixer/separator devices for the extraction, the use of coalescing filters, such as candle filters or sand filters, has proven to be advantageous for improving phase separation. The filter can be installed here directly after the mixer (stirring container)

and/or in the organic discharge from the separator. Also preferred for improving phase separation is the use of electrocoalescers. These have proven suitable for separating aqueous foreign phases of up to 5 mass %. The use of coalescing devices in the work-up method preferred according to the invention is also advantageously suitable for separating finely dispersed aqueous phase from the organic discharge of an extraction column comprising the majority of the ligand of the formula (I).

In one suitable embodiment, the extraction takes place in at least one mixer/separator combination for the extraction of aluminum-containing components from the isopulegol-depleted bottom product from step I). The use of a further mixer/separator combination is particularly advantageous for subsequently reextracting and thus returning to the process fractions of the ligand of the formula (I) or, if appropriate, of the higher-boiling solvent which, if appropriate, with the aluminum-containing compounds to be separated off, partially pass into the extractant.

Under certain circumstances, it may be advantageous to subject the organic phase comprising the majority of ligands of the formula (I) to a drying step before separating off the ligand in step III) or after separating it off. Suitable drying methods are the customary ones known to the person skilled in the art, in particular the adsorption to dehydrating agents, e.g. using a zeolithic molecular sieve.

In an alternative embodiment of the work-up method preferred according to the invention in the course of step b), after bringing the isopulegol-depleted bottom product into contact with the aqueous base, the water is completely or at least partially removed by distillation.

In order to prevent the ligand of the formula (I) from separating off prematurely, specifically by crystallization, at no point during step II) should the solubility of the ligand in the organic phase be exceeded. This can take place through appropriate selection of the temperature and/or the amount and type of any added solvents.

Consequently, in one preferred embodiment of the work-up method preferred according to the invention, a discharge of the heated bottom product from step I) is brought into close contact with a heated aqueous base.

Within the context of the present work-up method, the expression "heated" refers to a temperature above room temperature and below the respective boiling point temperatures of the aqueous or organic solutions under the reaction conditions in question. In particular, the expression "heated" refers to a temperature in the range from 25° C. to 150° C., specifically in the range from 70° C. to 100° C.

Depending on the auxiliaries used, if appropriate, in the cyclization, preferred according to the invention, of citronellal in the presence of diarylphenoxyaluminum compounds, the isopulegol-depleted bottom product can, if appropriate, comprise further components not separated off in step I). These are preferably separated off in step II). In this case, the aqueous phase obtained can be subjected to a suitable separation process in order to recover these components, e.g. an auxiliary (iv).

Step III):

In step III) of the work-up method preferred according to the invention in the course of step b), the ligand of the formula (I) is separated off from the organic phase comprising the majority of the ligand obtained in step II) by crystallization, where step III) can be carried out continuously or discontinuously. Suitable embodiments of this step are, for example, crystallization and/or complete or at least partial distillative removal of volatile constituents.

In one preferred embodiment of the cyclization or work-up method preferred according to the invention, the ligand of the formula (I) is separated off by crystallization.

For the crystallization of the ligand of the formula (I), the solubility of the ligand of the formula (I) in the organic phase from step II) must firstly be exceeded. This can take place, for example, by a cooling process of the organic phase or by (partial) distillative separation of the solvent. Methods for this purpose are known to the person skilled in the art. For the technical configuration of the crystallization preferred according to the invention in the course of the preferred work-up method, customary cooling crystallizers, evaporating crystallizers, vacuum crystallizers, crystallizing troughs or spray crystallizers, for example, are suitable.

In one preferred embodiment, the crystallization, to be carried out preferably, of the ligand of the formula (I) takes place by cooling the organic phase from step II) of the method. In general, crystallization takes place at a temperature in the range from −50° C. to 100° C., preferably in the range from −20° C. to 50° C. and specifically in a range from 10° C. to 40° C.

This process can be accelerated by adding seed crystals.

The crystalline ligand of the formula (I) can be isolated from the solution, for example, by filtration, flotation, centrifugation or sieving.

The ligand of the formula (I) retained in this way can, if appropriate, be dried by suitable drying methods. Methods for this are known to the person skilled in the art. For example, for the technical configuration of the drying, customary roller dryers, disk dryers, chamber dryers, fluidized-bed dryers or radiation dryers are suitable.

The organic phase depleted in ligand of the formula (I) can again be added to the process before or during step I).

In one suitable embodiment of the work-up method preferred according to the invention, the crystallization takes place upon cooling to room temperature from a heated, saturated organic phase obtained in step II).

The method is suitable to a particular extent for producing racemic isopulegol starting from racemic citronellal, and also for producing optically active isopulegol, preferably L-isopulegol, by cyclization of corresponding optically active citronellal. The cyclization under the stated conditions in the presence of the diarylphenoxyaluminum compounds, as described above and preferred in the course of the method according to the invention, generally proceeds in a highly diastereoselective manner and largely with the retention of the stereochemical information, i.e. of the enantiomer excess of the citronellal used, preferably of the D-citronellal used.

The isopulegol obtainable in this way by the cyclization of citronellal as explained above can then be further purified by suitable separating and/or purification methods, in particular by distillation, and be at least largely freed from undesired impurities or by-products. Of particular suitability for carrying out such a distillative purification is a dividing wall column or an interconnection of two thermally coupled columns with side take-off, where the isopulegol can be obtained in purified and/or enriched form at the side take-off in liquid form. Using a dividing wall column with a total number of from about 30 to about 200, preferably about 45 to about 90, theoretical plates and one or more, preferably one or two side take-off points, it is possible, upon appropriate selection of pressure and temperature of the distillation, usually to isolate isopulegol with high purity, often with a purity of 97% by weight and above, preferably of 98% by weight and above. It is advantageous here to work at absolute pressures in the column of from 10 to 500 mbar, preferably at 50 to 200 mbar. Within the context of one preferred embodiment, the isopulegol obtained by cyclization of citronellal is purified by distillation, in which case the purification is carried out in a dividing wall column having 30 to 200 theoretical plates and one or more side take-off points at an absolute operating pressure of from 10 to 500 mbar.

Specific embodiments of such material separations by distillation by means of a dividing wall column can be found in the above description of the distillative separation of geranial- and neral-containing substance mixtures and also the fine distillation of menthol described below. On account of the melting point of isopulegol below 14° C. (corresponds approximately to the melting point of pure L-isopulegol), where appropriate, measures known to the person skilled in the art are to be employed in order to avoid undesired solidification of the discharges from the dividing wall column at relatively low ambient temperatures, for example at a colder time of year.

Step c): Purification of Isopulegol by Crystallization

According to step c) of the method according to the invention, a purification of isopulegol obtainable as described above according to step b) of the method according to the invention by crystallization is carried out.

The crystallization of isopulegol is known to the person skilled in the art and disclosed, for example, in U.S. Pat. No. 5,663,460. The patent describes the purification of (−)-n-isopulegol by crystallization from petroleum ether or advantageously from acetone at temperatures of from −20° C. to −60° C. Here, an increase in the optical purity can also be achieved.

In addition, U.S. Pat. No. 3,218,361 discloses a method for the crystallization of isopulegol from substance mixtures comprising isopulegol and diastereomers of isopulegol. The crystallization is carried out here at temperatures below 0° C., preferably below −30° C. and for example at −65° C. and can be carried out either from the solution or from the melt.

WO 2007/023109, to which reference is hereby made in its entirety and the disclosure of which including all preferences and embodiments is to be considered part of the present disclosure, discloses a method for producing enriched isopulegol, specifically enriched L-isopulegol of the formula (XX)

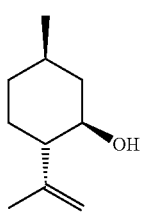

(XX)

by crystallization from a melt comprising L-isopulegol of the formula (XX).

Such a method for the purification of isopulegol, specifically of optically active L-isopulegol by melt crystallization constitutes a preferred method for the purification of isopulegol by crystallization according to step c) of the method according to the invention.

Suitable starting materials for carrying out the crystallization according to step c) are melts which comprise racemic or optically active, preferably optically active, isopulegol of the formula (XX), preferably in the form of its L-enantiomer L-isopulegol, as is shown in formula (XX) in its absolute configuration.

Step c) of the present invention accordingly relates to a method for the purification of isopulegol by crystallization from a melt which, besides isopulegol, also comprises other undesired impurities or compounds, for example by-products which have been produced in the production of the isopulegol used, but is essentially free from solvents.

The term "enriched isopulegol" within the context of the crystallization to be carried out according to step c) of the present invention is to be understood as meaning that isopulegol which has a higher content of L-isopulegol than the material serving as starting material for carrying out the crystallization, preferably the melt crystallization. In particular, within the context of step c), the term "enriched isopulegol" is to be understood as meaning that which has a chemical purity of at least about 90% by weight, preferably at least about 95% by weight and particularly preferably about 95 to about 99.95% by weight. In this connection, isopulegol of the formula (XX), also referred to below as n-isopulegol, can be present in the mixture with one or more of the three further possible diastereomers of isopulegol, namely iso-isopulegol of the formula (XXI), neo-isopulegol of the formula (XXII) and neoiso-isopulegol of the formula (XXIII).

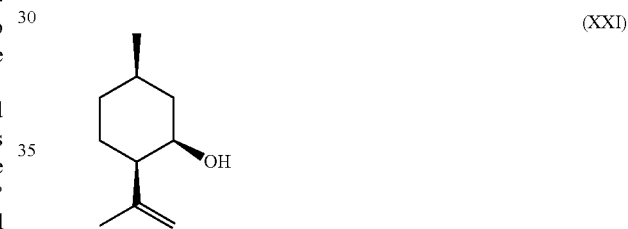

(XXI)

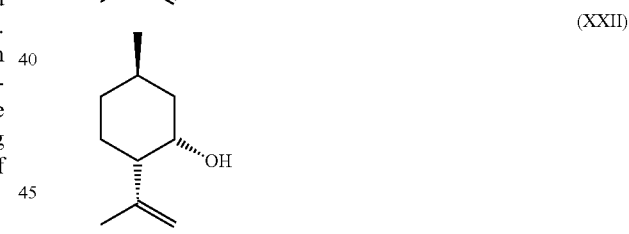

(XXII)

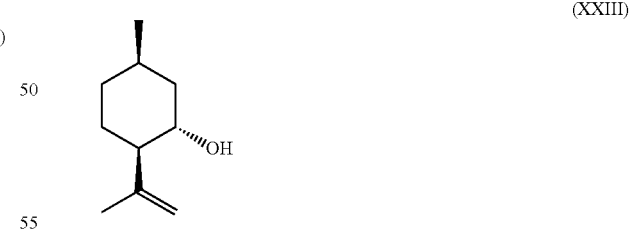

(XXIII)

A suitable starting material for carrying out the method according to the invention is isopulegol of any origin, i.e. isopulegol isolated from natural sources or synthetically produced isopulegol, but preferably synthetically produced isopulegol, in particular that which can be obtained according to step b) described above. The melt to be used preferably according to the invention preferably consists to at least about 70% by weight, particularly preferably to at least about 75% by weight, very particularly preferably to about 80 to about 100% by weight and especially preferably to about 85 to about 100% by weight, of isopulegol and its diastereomers iso-isopulegol of the formula (XXI), neo-isopulegol of the formula (XXII) and neoiso-isopulegol of the formula (XXIII).

A preferred embodiment of the crystallization according to step c) of the method according to the invention relates to a method for producing enantiomer- and/or diastereomer-enriched n-isopulegol of the formula (XX) by crystallization from a melt comprising n-isopulegol of the formula (XX) and optionally further diastereomers of isopulegol.

The n-isopulegol of the formula (XX) obtainable from the melt by the crystallization according to step c) of the method according to the invention is usually produced in diastereomer-enriched form. The term "diastereomer-enriched" is to be understood here as meaning that the products obtainable in the course of the crystallization have a higher content of the desired diastereomer n-isopulegol relative to the other diastereomers specified above than the melt used preferably according to the invention. In particular, the term diastereomer-enriched isopulegol is to be understood as meaning one which comprises to at least 80 to 99.9% by weight, preferably 90 to 99.8% by weight and particularly preferably 95 to 99.5% by weight, n-isopulegol of the formula (XX) as well as together up to 20% by weight, preferably up to 10% by weight, particularly preferably 5 to 0.5% by weight, of the further diastereomers of the formulae (XXI), (XXII) and/or (XXIII).

When using optically active starting materials, i.e. starting materials in which the two enantiomers of the n-isopulegol are not present in the same ratio, within the context of one preferred embodiment of the crystallization method according to step c), enantiomer-enriched n-isopulegol is obtained. The term enantiomer-enriched is to be understood here as meaning that the products obtainable according to the invention have a higher content of one enantiomer of n-isopulegol relative to the other enantiomer, i.e. have a higher enantiomer excess (ee), than the melt used according to the invention.

The crystallization method to be carried out according to the invention in accordance with step c) accordingly also permits the production of enantiomer- and diastereomer-enriched n-isopulegol by crystallization from a melt comprising optically active n-isopulegol with a slight enantiomer excess.

Starting materials preferred according to the invention, or melts thereof, comprise n-isopulegol with an enantiomer excess of at least about 75%, particularly preferably of at least about 80% ee, very particularly preferably of about 85 to about 95% ee and especially preferably from 85 to 90% ee.

When using optically active starting materials as described above, in the course of the crystallization method according to step c) of the method according to the invention, upon appropriate selection of the process parameters, usually enantiomer-enriched n-isopulegol of the formula (XX) is obtained with an enantiomer excess of at least about 85%, preferably about 90 to about 100% ee, particularly preferably about 95 to about 99.9% ee and very particularly preferably about 97 to about 99.9% ee.

In addition, when using optically active starting materials as described above, besides the enantiomer-enriched isopulegol described above, also enantiomer-depleted isopulegol is obtained, the term enantiomer-depleted isopulegol being understood as meaning isopulegol which has a lower enantiomer excess than the isopulegol used in the crystallization according to step c). The enantiomer-depleted isopulegol obtained in this way usually has a low enantiomer excess of up to about 20%, corresponding to a molar ratio of the enantiomers L-isopulegol to D-isopulegol of about 60:40. Preferably, the enantiomer-depleted isopulegol obtained in this way has an enantiomer excess of up to 15% ee, preferably of up to 10% ee, particularly preferably of up to 7% ee and very particularly preferably of up to 5% ee.

The melt crystallization to be carried out preferably according to step c) of the method according to the invention can be carried out, for example, in the form of a layer crystallization or in the form of a suspension crystallization. To carry out a layer crystallization, a cooled surface is usually introduced into the melt of the optionally optically active isopulegol used as starting material. Thereafter, a crystal layer of optionally enantiomer- and/or diastereomer-enriched isopulegol is formed on the cooled surface introduced and can then be separated from the remaining mother melt. The crystalline enriched isopulegol obtained in this way can be melted again in further, assistant-free purification steps (e.g. by washing with pure product, "sweating" just below the melting point). This operation can then be repeated as often as desired to increase the purity and the yield in the molten crystallizate and in the mother melt. In general, during the layer crystallization to be carried out advantageously in the course of step c) of the method according to the invention, dynamic methods should be differentiated from static methods. In dynamic methods, the mother phase, i.e. the molten starting material, is usually moved actively or passively along the crystallizate or the cooling surface. In the course of static methods, the melt crystallization to be carried out preferably according to the invention is carried out in a resting melt.

The melt crystallization according to step c) to be carried out preferably according to the invention can also be carried out in the form of a dynamic layer crystallization. Within the context of an again preferred embodiment, this variant is carried out in tube bundle heat eschangers as described in G. F. Arkenbout, Melt Crystallization Technology, Lancater/PA, Technomic Publ. Co., 1995 (chap. 6.2). Here, melt and coolant, e.g. in the form of a trickle film, are conducted along the inner and outer walls of the heat exchangers. Such an apparatus allows easier removal of the obtained crystalline isopulegol from the mother melt and any obtained sweating fractions by simple efflux under the effect of gravity and, apart from a circulation pump, does not require any further stirring elements.

To carry out a dynamic layer crystallization, the optionally optically active isopulegol serving as starting material, usually having a temperature which is above its melting point and can be read off from the melt diagram, is introduced into the melt crystallizer as described above and conducted through the cooled tube bundle heat exchanger by pumped circulation. To achieve an advantageous crystallization result, the lowering of the cold carrier temperature is preferably selected such that a crystal layer of thickness from about 1 mm to about 50 mm, preferably about 5 mm to about 20 mm, is formed within a period of time of from about 0.5 h to about 10 h, preferably within from about 1 h to about 4 h. The coolant temperatures required for this purpose are generally about 1 K to about 40 K, preferably from about 5 K to about 20 K, below the particular melting temperature.

After carrying out the dynamic layer crystallization, the mother melt which remains is usually discharged. By raising the temperature of the heating or cooling medium of the heat exchanger, it is possible to melt any adhering mother melt residues or any incorporated impurities, or to remove them by drainage. Advantageous heat carrier temperatures are in the range from about 15° C. to about 60° C., particularly advantageously from about 20 to about 30° C. During this process, referred to as "sweating", according to the purity requirements, from about 1 to about 50% by weight, often from about 5 to about 20% by weight, of the crystallized isopulegol can be melted again. Finally, the enantiomer- or diastereomer-enriched crystal layer which remains is advantageously melted off and either fed to its further use or crystallized once again for further purification or increase in the enantiomer or diastereomer excess. The mother melt, separated off as described, and the fraction released by "sweating" can be returned to the method according to the invention to increase the yield. Alternatively, there is the option, before the "sweating" of the crystal layer, to wash it by bringing it into contact with molten pure product, i.e. to free it from any firmly adhering mother liquor. When using optically active starting materials, enantiomer-depleted or racemic isopulegol is obtainable from the mother liquor obtainable in this way.

The crystallization, preferred in the course of step c) of the method according to the invention, of isopulegol or n-isopulegol from the melt is carried out advantageously at temperatures in the range from about −20° C. to about 15° C., preferably in the range from about −10° C. to about 15° C. and particularly preferably in the range from about −5° C. to about 14° C. The precise position of the temperature range depends here on the optical and chemical starting purity of the starting material and the desired yield and can be read off by the person skilled in the art from the melt diagram of the isopulegol used in each case.

In the case of the inventive production method to be carried out in the course of step c) for enriched, preferably enantiomer- or diastereomer-enriched isopulegol, all specified methods can be used with good success. Within the context of one preferred embodiment of the method according to the invention, the crystallization is carried out in the form of a static layer crystallization, i.e. in a static layer crystallizer with internal heat exchanger surfaces.

The arrangement of said heat exchanger surfaces is not subject here to any particular requirements. Usually, the isopulegol serving as starting substance is introduced into the melt crystallizer with a temperature which can be read off from the melt diagram and is above its melting point, and the contents of the crystallizer are cooled, depending on the purity of the starting material, to temperatures of from about −20° C. to about 15° C., preferably from about −10° C. to about 15° C., within a period of time of from about 5 h to about 30 h, preferably from about 10 to about 20 h. To achieve an advantageous crystallization result, preference is given to selecting cooling rates of from about 0.1 K/h to about 20 K/h, particularly preferably of from about 0.5 K/h to about 5 K/h.

Following crystallization of the desired amount of starting material, the mother melt which remains is advantageously discharged. By slowly raising the temperature of the heating/cooling medium of the heat exchanger, it is possible to melt any adhering mother melt residues or any incorporated impurities, or to remove them by drainage. Advantageous heating rates are in the range between about 0.1 and about 20 K/h, preferably in the range from about 0.5 to about 5 K/h. In this process, which is referred to as "sweating", depending on the purity requirements, from about 3 to about 60% by weight, often about 10 to about 30% by weight, of the crystallized isopulegol can be melted again. Finally, the enantiomer-enriched crystal layer which remains can advantageously be melted off and either fed to its further use or crystallized once again for further purification or increase in the enantiomer excess. The mother melt separated off as described and the fraction released by "sweating" can be returned to the melt crystallization method preferred according to the invention to increase the yield.

The melt crystallization to be carried out preferably according to the invention in the course of step c) can alternatively also be carried out in the form of a suspension crystallization. In this case, the crystals are usually produced in suspended form in their mother melt without any need for a crystal layer to form. Here, a continuous procedure at constant temperature and a discontinuous procedure with gradually lowered temperature are possible. Suitable cooling surfaces here are, for example, walls of a stirred vessel equipped with a close-clearance stirrer, so-called scratching coolers or the wiped surfaces in a cooling disk crystallizer. Alternatively, the melt can also be cooled by applying a vacuum and adiabatic evaporation of the substance of value (or, less preferably, of a solvent added as an auxiliary). The suspended crystals can then be separated off in a manner known per se to a person skilled in the art, e.g. using any desired filter element, e.g. a suction filter, a centrifuge or a belt filter. Owing to the extremely high purifying action that is achievable in principle, the separation can also be carried out by means of a scrubbing column, in which case the suspension of pure product melted at the bottom which has been conducted from the top toward a filter is conveyed countercurrently as a scrubbing medium.

The isopulegol, in particular the enantiomer-depleted or racemic isopulegol as described above, obtained by crystallization as described above according to step c) of the method according to the invention can also be further purified by further separating methods, preferably by distillation. In this connection, the use of dividing wall columns or interconnections of columns in the form of a thermal coupling have proven to be advantageous from the point of view of processing and costs.

Step d): Catalytic Hydrogenation of Isopulegol to Give Menthol

According to step d) of the method according to the invention, a catalytic hydrogenation of isopulegol obtained according to step c) to menthol is carried. Suitable starting materials for carrying out the catalytic hydrogenation are either the enantiomer- or diastereomer-enriched isopulegol obtained according to step c) or the enantiomer-depleted and racemic isopulegol separated off as by-product in the course of the crystallization.

Within the context of one preferred embodiment, the catalytic hydrogenation of racemic or optically active isopulegol according to step d) of the method according to the invention is carried out in the presence of a heterogeneous nickel-containing catalyst. When using enantiomer-enriched or enantiomerically pure isopulegol, preferably L-isopulegol, the catalytic hydrogenation according to step d) is preferably carried out in the presence of a heterogeneous nickel- and copper-containing catalyst.

DE 577 036 discloses a method for producing synthetic menthol by hydrogenation of thymol. Nickel, nickel/copper and cobalt catalysts are described as suitable catalysts.

Specific nickel catalysts have also been used for the catalytic hydrogenation of piperitol to give menthol, as described in GB 1,503,723.

EP 1 532 091 discloses a method for producing racemic menthol by catalytic hydrogenation of isopulegol which has been used in the form of a diastereomer mixture of 70.1% isopulegol, 18.1% neo-isopulegol, 6.8% iso-isopulegol and 2.6% neoiso-isopulegol. The catalyst used was Raney nickel doped with iron and chromium. This gave menthol in the form of a mixture of the possible diastereomers which consisted to 61.4% of menthol and to 35.6% of the further diastereomers of menthol.

A further route to menthol is that of processes for the diastereoselective cyclization of citronellal to isopulegol, as described, for example, in the aforementioned EP 1 225 163 or WO 2006/092433. The isopulegol obtained in this way can then be hydrogenated to menthol in a further step.

R. H. Pickard et al. described, in J. Chem. Soc. 1920, 1248-1263, the production of L-menthol by catalytic hydrogenation of L-isopulegol in the presence of colloidal palladium.

B. Dudley Sully et al. describe, in P.& E.O.R. 1068, 235-366, the production of L-menthol by hydrogenation of L-isopulegol in the presence of Raney nickel at a temperature of 120° C.

EP 1 053 974 discloses a method for the catalytic hydrogenation of isopulegol to menthol in the presence of a catalyst of 5% palladium on carbon at a hydrogen pressure of 5 bar.

EP 0 394 842 relates to catalysts for the hydrogenation of aliphatic unsaturated compounds, which comprises nickel and copper and is characterized by a content of from 20 to 75% by weight of nickel oxide, 10 to 75% by weight of zirconium dioxide and 5 to 50% by weight of copper oxide, in each case based on the oxidic, unreduced catalyst. Examples of substrate specified are: butyne-2-diol-1,4, butene-2-diol-1,4 and 2-ethylhexen-2-al.

According to one particularly preferred embodiment within the context of step d) of the method according to the invention, a method for producing racemic or optically active menthol of the formula (XXIV) is carried out

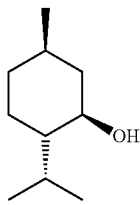

(XXIV)

by catalytic hydrogenation of racemic or optically active isopulegol of the formula (XX)

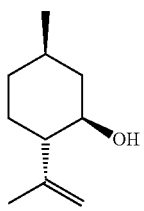

(XX)

in the presence of hydrogen and a catalyst comprising
  30 to 70% by weight of oxygen-containing compounds of nickel, calculated as NiO,
  15 to 45% by weight of oxygen-containing compounds of zirconium, calculated as $ZrO_2$,
  5 to 30% by weight of oxygen-containing compounds of copper, calculated as CuO and
  0.1 to 10% by weight of oxygen-containing compounds of molybdenum, calculated as $MoO_3$, where the data in % by weight are based on the dry unreduced catalyst.

A suitable starting material for carrying out the hydrogenation method preferred according to the invention in the course of step d) in the presence of said nickel- and copper-containing catalysts is racemic or optically active isopulegol of the formula (XX), although it is possible in principle to use isopulegol of any purity. However, the method according to the invention is suitable preferably for converting isopulegol of high purity, i.e. of isopulegol with a purity of 80% by weight or higher, preferably of 90% by weight or higher. Especially suitable as starting material for carrying out the method according to the invention is isopulegol having a chemical purity of 97% by weight or higher, preferably of from 98 to 100% by weight, particularly preferably of from 98.5 to 99.9% by weight, very particularly preferably of at least 99 to 99.9% by weight. Here, the term chemical purity also comprises the diastereomer purity of the isopulegol used with respect to the diastereomers iso-isopulegol of the formula (XXI), neo-isopulegol of the formula (XXII) and neoiso-isopulegol of the formula (XXIII).

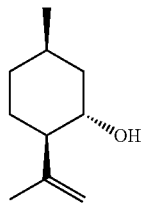

(XXI)

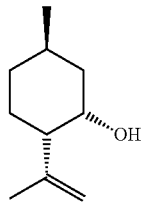

(XXII)

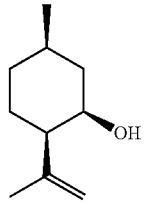

(XXIII)

Accordingly, an isopulegol that is particularly preferred as starting material for carrying out the catalytic hydrogenation according to step d) of the method according to the invention has a diastereomer purity, as described above, of 97% by weight or higher, preferably of from 98 to 100% by weight, particularly preferably of from 98.5 to 99.9% by weight and very particularly preferably of at least 99 to 99.9% by weight. Here, the specified formulae, like all formulae depicted within the context of the present invention, can in each case represent both enantiomers (or mixtures thereof) and serve to illustrate the relative configuration of the stereogenic centers.

According to the invention, isopulegol can be used in racemic or nonracemic, i.e. optically active form, in the course of step d). When using racemic isopulegol of the formula (XX), in accordance with the invention, racemic menthol of the formula (XXIV) is obtained. When using optically active, preferably enantiomer-enriched and particularly preferably enantiomerically pure isopulegol of the formula (XX), optically active menthol of the formula (XXIV) is accordingly obtained. If isopulegol in optically active form is used, preference is given according to the invention to those mixtures which comprise predominantly the L-isopulegol enantiomer, as reproduced in its absolute configuration for example in formula (XX).

In the course of step d) of the method according to the invention, use is made in the case of the reaction of enantiomer-enriched isopulegol, i.e. D- or preferably L-isopulegol with an enantiomer excess (ee) of 80% or higher, preferably of 85 or better 90% ee or higher, particularly preferably 95 to 100% ee, very particularly preferably 96 to 99.9% ee, further preferably 97 to 99.8% ee, even more preferably 98 to 99.7% ee and especially preferably 98.5 to 99.6% ee. Starting from L-isopulegol in optically active form produces, in the manner according to the invention, L-menthol, as reproduced in its absolute configuration in formula (XXIV), in optically active form.

The catalytic hydrogenation method preferred according to the invention is carried out in the presence of hydrogen and in the presence of a heterogeneous catalyst, the heterogeneous catalyst to be used comprising 30 to 70% by weight, preferably 40 to 60% by weight, of oxygen-containing compounds of nickel, calculated as NiO, 15 to 45% by weight, preferably 20 to 40% by weight, of oxygen-containing compounds of zirconium, calculated as $ZrO_2$, 5 to 30% by weight, preferably 10 to 25% by weight, of oxygen-containing compounds of copper, calculated as CuO and 0.1 to 10% by weight, preferably 0.5 to 5% by weight of oxygen-containing compounds of molybdenum, calculated as $MoO_3$, if appropriate as well as further components in an amount of from 0 to 10% by weight, preferably 0 to 5% by weight, such as, for example, graphite. Here, the data in % by weight refer to the dry unreduced catalyst.

Since the concentration data is in each case—unless stated otherwise—based on the catalytically active mass of the catalyst, the catalystically active mass of the catalyst is defined hereinbelow as the sum of the masses of the catalytically active zirconium, nickel, copper and molybdenum in the catalyst, in each case calculated as $ZrO_2$, NiO, CuO and $MoO_3$, respectively, after the last heat treatment thereof and before the reduction thereof with hydrogen.

Within the context of one preferred embodiment, for carrying out the hydrogenation method according to step d) preferred according to the invention, use is made of those catalysts comprising
- 45 to 55% by weight of oxygen-containing compounds of nickel, calculated as NiO,
- 25 to 35% by weight of oxygen-containing compounds of zirconium, calculated as $ZrO_2$,
- 5 to 20% by weight of oxygen-containing compounds of copper, calculated as CuO,
- 1 to 3% by weight of oxygen-containing compounds of molybdenum, calculated as $MoO_3$ and
- 0 to 5% by weight further components, where the data in % by weight add up to 100% by weight and are based on the dry unreduced catalyst. According to the invention, particular preference is given to those catalysts which consist of the aforementioned components in the weight fractions likewise specified above.

A catalyst that is particularly preferred for use in the course of step d) of the method according to the invention consists to 49 to 53% by weight of NiO, to 15 to 19% by weight of CuO, to 28 to 32% by weight of $ZrO_2$ and to 1 to 2% by weight of $MoO_3$, and optionally to 0 to 3% by weight of further components, such as, for example, graphite, the fractions by weight of the individual components selected in each case adding up to 100% by weight. Catalysts of this type are known and can be produced, for example, as described in EP 0 696 572, to which reference is made in this regard in its entirety.

The catalysts to be used preferably according to the invention in the course of step d) can be produced, for example, using precipitation methods. Thus, for example, they can be obtained by a coprecipitation of the nickel and copper components from an aqueous salt solution comprising these elements by means of mineral bases in the presence of a slurry of a sparingly soluble, oxygen-containing zirconium compound, and subsequent washing, drying and calcination of the resulting precipitate. Sparingly soluble oxygen-containing zirconium compounds which can be used are, for example, zirconium dioxide, zirconium oxide hydrate, zirconium phosphates, borates and silicates. The slurries of the sparingly soluble zirconium compounds can be prepared by suspending finely particulate powders of these compounds in water with vigorous stirring. These slurries are advantageously obtained by precipitating the sparingly soluble zirconium compounds from aqueous zirconium salt solutions by means of mineral bases.

Preference is given to producing the catalysts which can be used in the course of step d) of the method according to the invention via a coprecipitation of all of their components. For this, an aqueous salt solution comprising the catalyst components is expediently admixed at elevated temperature and with stirring with an aqueous mineral base, in particular an alkali metal base—for example sodium carbonate, sodium hydroxide, potassium carbonate or potassium hydroxide—until the precipitation is complete. The type of salts used is generally unimportant—since the principal factor in this procedure is the solubility in water of the salts, one criterion is their good solubility in water required for producing these relatively highly concentrated salt solutions. It is considered to be self-evident that when selecting the salts of the individual components, naturally only salts with those anions which do not lead to disruption, whether by causing undesired precipitations or by complicating or preventing the precipitation through complex formation, are selected.

Catalysts which can be used according to the invention in the course of step d) and having particularly advantageous properties are obtainable by precipitating some of the zirconium component of the catalyst, expediently from an aqueous zirconium salt solution, separately in a precipitation apparatus by adding aqueous mineral bases. The remainder of the zirconium component of the catalyst can then be precipitated onto the thus obtained, preferably freshly precipitated zirconium oxide hydrate, together with the other catalytically active components in a coprecipitation, as has been described above. In this connection, it has generally proven to be particularly expedient to preliminarily precipitate 10 to 80% by weight, preferably 30 to 70% by weight and in particular 40 to 60% by weight, of the total amount of zirconium of the catalytically active mass.

The precipitates obtained in these precipitation reactions are generally chemically nonuniform and consist, inter alia, of mixtures of the oxides, oxide hydrates, hydroxides, carbonates and insoluble and basic salts of said metals. For the filterability of the precipitates, it may be found to be favorable if they are aged, i.e. if they are left alone for a certain time after the precipitation, if appropriate at elevated temperature or while passing air through.

The precipitates obtained by these precipitation methods can be further processed as usual to give the finished catalysts that can be used preferably according to the invention in the course of step d). After washing, they are generally dried at 80 to 200° C., preferably at 100 to 150° C., and then calcined. The calcination is performed generally at temperatures between 300 and 800° C., preferably at 400 to 600° C., in particular at 450 to 550° C.

After the calcination, the catalyst is expediently conditioned, whether by adjusting it to a particular particle size by grinding, or by grinding and then mixing it with shaping auxiliaries such as graphite or stearic acid, pressing to pellets by means of a tableting press and heat-treating. The temperatures correspond here in general to the temperatures during the calcination.

The catalysts produced in this way comprise the catalytically active metals in the form of a mixture of their of oxygen-containing compounds, i.e. in particular as oxides and mixed oxides.

The catalysts produced in this way can be stored and used as such. Before they are used as catalysts in the course of step d) of the method according to the invention, they are usually prereduced. However, they can also be used without prereduction, in which case they are then reduced by the hydrogen present in the reactor under the conditions of the hydrogenation to be carried out according to the invention. For the prereduction, the catalysts are generally exposed to a nitrogen-hydrogen atmosphere firstly at 150 to 200° C. over a period of from 12 to 20 hours, and then treated in a hydrogen atmosphere at 200 to 300° C. for a further up to approximately 24 hours. During this prereduction, some of the oxygen-containing metal compounds present in the catalysts are usually reduced to the corresponding metals, such that they are present in the active form of the catalyst together with the different types of oxygen compounds.

In general, the catalysts to be used in the course of step d) of the hydrogenation method according to the invention are preferably used in the form of unsupported catalysts. The term "unsupported catalyst" refers to a catalyst which, in contrast to a supported catalyst, consists only of catalytically active mass. Unsupported catalysts can be used in such a way that the catalytically active mass ground to powder is introduced into the reaction vessel, or in such a way that the catalytically active mass, after grinding, mixing with shaping auxiliaries, shaping and heat-treatment, is arranged in the reactor in the form of catalyst moldings—for example as spheres, cylinders, tablets, rings, spirals, strands and the like.

Within the context of one preferred embodiment of the catalytic hydrogenation method to be carried out according to step d), the selected heterogeneous catalyst is used in the form of a fixed-bed catalyst.

For carrying out the catalytic hydrogenation according to step d) of the method according to the invention, the isopulegol starting material as described above is brought into contact with hydrogen and the selected catalyst. The hydrogen can be used in undiluted form, usually in a purity of about 99.9% by volume or in diluted form, i.e. in the form of mixtures with inert gases, such as, for example, nitrogen or argon. Preference is given to using hydrogen in undiluted form.

The hydrogenation of isopulegol can be carried out with good success without the addition of solvent or in the presence of organic solvents that are inert under the reaction conditions, such as, for example, methanol, ethanol, isopropanol, hexane, heptane, cyclohexane and the like. Preferably, the hydrogenation according to step d) of the method according to the invention is carried out without the addition of solvent.

The catalytic hydrogenation of isopulegol according to step d) can be carried out at a hydrogen pressure (absolute) in the range from 1 to 200 bar, preferably from 2 or better from 3 to 200 bar, particularly preferably from 4 or 5 to 150 bar, particularly preferably 5 to 100 bar and very particularly preferably in the range from 5 to 50 bar. The reaction temperature selected for carrying out the hydrogenation according to the invention is advantageously a temperature in the range from 20 to 150° C., preferably 40 to 130° C., particularly preferably 60 to 110° C. and very particularly preferably from 70 to 100° C.

In practice, when carrying out the hydrogenation of isopulegol according to step d), the procedure generally involves feeding the isopulegol to be converted to the catalyst, which is usually located in a preferably externally heated fixed-bed reactor, such as, for example, a tubular reactor, autoclave or tube bundle reactor, at the desired reaction temperature and the desired pressure. Here, the catalyst is generally loaded with 0.1 to 1.0, preferably 0.1 to 0.6 and particularly preferably with 0.2 to 0.4 kg of isopulegol per kg of catalyst and per hour. It may be expedient here to heat the isopulegol to be used before it is fed to the reaction vessel or the reactor, specifically preferably to the reaction temperature.

The reactor can be operated either in liquid-phase mode or in trickle mode, i.e. the starting materials can be passed through the reactor either from the bottom upward or from the top downward. The hydrogenation method according to the invention can be carried out either discontinuously or continuously. In both cases, unreacted starting material can be circulated together with the hydrogen.

The hydrogenation to be carried out preferably according to the invention in the course of step d) can also be carried out stepwise in a cascade of a plurality of, i.e. 2 to generally 4, preferably 2 or 3 and particularly preferably in two reactors connected in series, preferably fixed-bed reactors. Here, the main conversion of the reaction is achieved in the first reactor, usually referred to as the main reactor, under the reaction conditions described above, and the resulting crude product is fed to a second reactor, usually referred to as the postreactor, in which the as yet unreacted starting material is converted in the manner according to the invention at least largely to menthol, or in the case of the use, preferred according to the invention, of enantiomer-enriched or enantiomerically pure L-isopulegol, to L-menthol. Here, the reaction conditions can preferably be selected independently of one another within the aforementioned ranges.

The hydrogenation method described above can be carried out discontinuously, semicontinuously or fully continuously. Preference is given to carrying out the method continuously, in particular fully continuously, in which case the starting materials are introduced continuously into the reactor and the resulting reaction mixture or reaction product is discharged continuously from the reactor. It has furthermore proven advantageous, on account of the position of the melting point of the menthol reaction product according to the invention, specifically L-menthol, to provide heating of the transport lines used.

The described hydrogenation method to be carried out preferably in the course of step d) permits the production of, as desired, racemic or optically active menthol by catalytic hydrogenation of corresponding racemic or optically active isopulegol, usually resulting in the formation of undesired diastereomers of menthol only to a low degree. The method according to the invention accordingly produces, when using isopulegol with a corresponding purity, menthol of the formula (XXIV) in a chemical purity of 97% by weight or higher, preferably of 98 to 100% by weight, particularly preferably of 98.5 to 99.9% by weight, very particularly preferably of at least 99 to 99.9% by weight. Here, the term "chemical purity" also comprises the diastereomer purity of the resulting menthol with respect to the diastereomers neoiso-menthol of the formula (XXV), neo-menthol of the formula (XXVI) and iso-menthol of the formula (XXVII). Accordingly, the method according to the invention in the frame preferably produces menthol of the formula (XXIV) with a diastereomer purity of 97% by weight or higher, preferably of 98 to 100% by weight, particularly preferably of 98.5 to 99.9% by weight and very particularly preferably of at least 99 to 99.9% by weight.

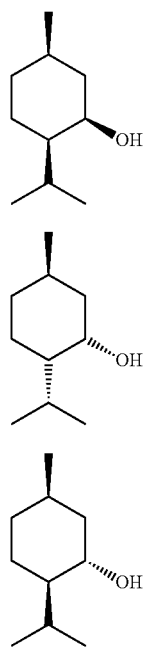

(XXV)

(XXVI)

(XXVII)

When isopulegol is used in optically active form, according to the invention preferably those mixtures which comprise predominantly the L-isopulegol enantiomer, the process product obtained according to the invention in the course of step d) is generally menthol in optically active form, preferably in the form of (−)- or L-menthol.

The explained catalytic hydrogenation preferred according to the invention in the presence of the above-described nickel- and copper-containing catalysts generally proceeds largely without noteworthy racemization of the material used. Consequently, depending on the enantiomer excess of the optically active isopulegol used, optically active L-menthol, preferably when L-ispulegol is used, is obtained with an enantiomer escess(ee) of 80% or higher, preferably of 85 or 90% ee or higher, particularly preferably 95 to 100% ee, particularly preferably 96 to 99.9% ee, very particularly preferably 97 to 99.8% ee, even more preferably 98 to 99.7% ee and especially preferably 98.5 to 99.6% ee.

The menthol obtained according to the invention, in particular the optically active menthol obtained, is moreover notable for a particularly low content of the undesired by-products menthone of the formula (XXVIII) and isomenthone of the formula (XXIX) and neoiso-menthol of the formula (XXV).

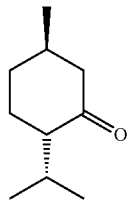

(XXVIII)

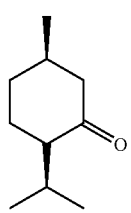

(XXIX)

These by-products are generally obtained in the course of the hydrogenation method preferred according to the invention only in a fraction, based on the amount of menthol obtained, of up to 0.5% by weight, preferably 0.4% by weight, particularly preferably 0.3% by weight, in particular 0.2% by weight and very particularly preferably 0.1 to 0% by weight.

As described above, in the crystallization to be carried out according to the invention according to step c), preferably the described melt crystallization using optically active isopulegol-comprising substance mixtures, as well as enantiomer-enriched or enantiomerically pure isopulegol, also, as described under step c), racemic or enantiomer-depleted isopulegol is produced. This racemic or enantiomer-depleted isopulegol can be hydrogenated in the course of the catalytic hydrogenation according to step d) in an advantageous manner by means of the preferred catalysts to give racemic or enantiomer-depleted menthol. In addition, it is also possible to hydrogenate racemic or enantiomer-depleted isopulegol of this type by methods of the prior art, for example by catalytic hydrogenation in the presence of hydrogen and Raney nickel as catalyst to give racemic or enantiomer-depleted menthol.

e) Fine Distillation of Menthol

The above-described method for the catalytic hydrogenation of isopulegol purified beforehand by crystallization, preferably by melt crystallization, generally produces racemic and optically active menthol, preferably racemic or enantiomer-depleted menthol and L-menthol of high chemical purity, also with regard to undesired diastereomers of menthol and, in the case of enantiomer-enriched optically active menthol, of high enantiomer purity. To guarantee the highest quality standards, especially with regard to the sensory, specifically olfactory properties of the resulting menthol, and also with regard to the purity requirements in pharmacopeia, it has proven to be advantageous to subject the enantiomer-enriched optically active menthol obtained according to step d) or racemic or enantiomer-depleted menthol to a final distillation. The method according to the invention therefore comprises, in the context of a preferred embodiment as further optional step e), the distillative purification of racemic and/or optically active menthol obtained according to steps a) to d) or of racemic and/or optically active menthol obtained according to steps 0) to d), preferably by means of a dividing wall column.

Various purification methods for menthol are described in the literature. For example, the person skilled in the art is aware, besides the fractional distillation with and without steam, as described, for example, in DE 568 085 or DE 1 189 073 and U.S. Pat. No. 1,930,411, JP 27003884 or JP 32009869, of extraction methods and crystallization methods.

These methods are sometimes also used in combination, e.g. as combinations of crystallization and fractional distillation, or else in combination with chemical reactions or derivatizations.

GB 285,394 relates to a method for producing racemic menthol by hydrogenating thymol, fractional distillation of the mixtures obtained therefrom and subsequent freezing of neomenthol out of the menthol fractions.

GB 285,833 describes a method for producing thymol by fractional distillation of mixtures which have been obtained from the condensation of cresol with acetone and, besides thymol, comprise isomeric methyl isopropyl phenols.

U.S. Pat. No. 2,827,497 discloses a method in which diastereomer mixtures of menthol obtained by fractional distillation and fractional crystallization are subjected to an oxidation and then further purified by another fractional distillation.

EP 0 242 778 describes a method for separating diastereomer mixtures, including mixtures of menthol, isomenthol, neomenthol and neoisomenthol, by extractive distillation, i.e. by distillation with addition of specific auxiliaries, such as, for example, succinamide.

The methods described mostly have the disadvantage that auxiliaries are used (steam or extractive distillation), or solids are produced. The fractional batch distillations are in most cases disadvantageous with regard to their yield of product of value since the product is thermally stressed for a longer period.

EP 1 514 955 relates to a method for the distillative work-up of the electrolysis discharge of the electrochemical oxidation of 1,1,2,2-tetramethoxyethane with methanol to give trimethyl orthoformate in a liquid electrolyte, where a dividing wall column having 30 to 150 theoretical plates is used.

DE 103 30 934 discloses a method for the continuous isolation of citronellal or citronellol from a crude mixture comprising at least one of these compounds by rectification. Preference is given here to using starting mixtures which are obtained by partial hydrogenation of citral or citronellal.

DE 102 23974 relates to a method for the continuous isolation of two stereoisomeric isoprenoid alcohols, specifically nerol and geraniol, from a crude mixture by rectification, where the crude mixture is introduced laterally into a feed column, at least one take-off column coupled to the feed column is provided, and a first and second isoprenoid alcohol are drawn off from the take-off column. Here, the feed and take-off columns are coupled such that there is no cross-mixing of vapors and condensate at least in the region of the take-off of the isoprenoid alcohols.

The distillative purification of menthol, specifically of L-menthol from its diastereomers neoisomenthol and isomenthol is usually very complex especially on account of the very small boiling point difference of ca. 2° C. at ambient pressure.

Within the context of one preferred embodiment, optional step e) of the method according to the invention is carried out in the form of a continuous method for producing racemic or optically active menthol of the formula (XXIV)

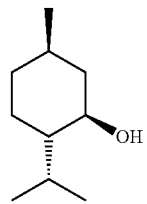

(XXIV)

in pure or enriched form by distillatively separating off racemic or optically active menthol from substance mixtures comprising racemic or optically active menthol and diastereomers of menthol, where the distillative separation is carried out in a dividing wall column having 50 to 300 theoretical plates and one or more side take-off points at an absolute operating pressure of from 5 to 500 mbar.

The starting materials used to carry out the separating method to be carried out preferably in the course of optional step e) are substance mixtures which comprise racemic or optically active menthol, preferably optically active menthol, particularly preferably L-menthol and diastereomers of menthol.

Diastereomers of menthol which may be mentioned are the above-depicted compounds neoisomenthol of the formula (XXV), neomenthol of the formula (XXVI) and isomenthol of the formula (XXVII), which, depending on the nature of the mixture serving as starting material, may be present in racemic or nonracemic, i.e. optically active form. Said diastereomers may be present in the substance mixtures to be used according to the invention in the course of step e) individually or in the form of mixtures with one another. The substance mixtures to be used as starting material in the course of the separating method preferred according to the invention comprise, besides menthol of the formula (XXIV) in racemic or optically active form, at least one of the diastereomers of the formulae (XXV), (XXVI) or (XXVII), but usually a mixture of two or all three of said diastereomers.

In the course of the method to be carried out if desired according to step e), preference may also be given to using those substance mixtures which, besides the aforementioned diastereomers of menthol, also comprise, also comprise isopulegol of the formula (XX)

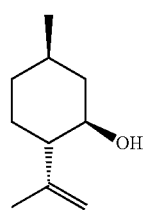

(XX)

and/or diastereomers thereof and also, if appropriate, menthone of the formula (XXVIII) and/or isomenthone of the formula (XXIX) depicted above.

The specified compounds may be present here, depending on the type, origin or production method of the substance mixture used in each case, in racemic or optically active form.

Diastereomers of isopulegol of the formula (XX), in particular L-isopulegol, which may be mentioned are the likewise above-depicted compounds iso-isopulegol of the formula (XXI), neo-isopulegol of the formula (XXII), neoiso-isopulegol of the formula (XXIII), which may likewise be present in racemic or nonracemic form depending on the type of mixture serving as starting material.

One preferred embodiment of the method to be carried out preferably according to optional step e) relates to the production of L-menthol in pure or enriched form by distillatively separating off L-menthol from substance mixtures comprising L-menthol and diastereomers of the menthol of the formulae (XXV), (XXVI) and/or (XXVII) and optionally isopulegol of the formula (XX) and/or diastereomers thereof of the formulae (XXI), (XXII) and/or (XXIII) and, if appropriate, menthone of the formula (XXVIII) or isomenthone of the formula (XXIX).

Suitable feed materials for carrying out the method to be carried out in the course of optional step e) are substance mixtures which comprise racemic or optically active menthol, preferably L-menthol in optically active form, preferably those which consist predominantly of racemic or optically active menthol, preferably L-menthol. Among these, preference is given to those substance mixtures which comprise at least 80% by weight or better 85 or even better 90% by weight to 99.9% by weight, particularly preferably 95 to 99.8% by weight and very particularly preferably at least 96% by weight, 97% by weight or most preferably at least 98% by weight to 99.7% by weight, 99.6% by weight or most preferably up to 99.5% by weight, of racemic or optically active menthol, preferably L-menthol, and, in addition, in a small amount, i.e. in a fraction of up to 20% by weight, preferably from 0.1 up to 10% by weight and particularly preferably from 0.2 up to 5% by weight, particularly preferably from 0.3 or better 0.4% by weight up to 2.5% by weight, even more preferably up to 1.5% by weight, better up to 1% by weight and most preferably up to 0.5% by weight, of further components, such as, for example, diastereomers of menthol, by-products such as isopulgol or diastereomers thereof, or menthone or isomenthone or other impurities, such as, for example, solvent residues or water.

When using substance mixtures which comprise menthol in optically active form, preferably L-menthol, it is usually present in an enantiomer excess of 90% ee or higher, preferably 95% ee, particularly preferably 97% ee or even more preferably 98% ee or higher, i.e. up to 100% ee or preferably up to 99.9% ee. Correspondingly optically active menthol, preferably L-menthol, in pure or enriched form is obtained from these substance mixtures in the course of the separating method to be carried out preferably according to the invention, the enantiomer excess of the product obtained generally corresponding, at least substantially, to the enantiomer excess of the menthol in the substance mixture used. When using substance mixtures comprising racemic menthol, racemic menthol of the formula (I) in pure or enriched form is obtained in accordance with the invention.

Within the context of one preferred embodiment of the method to be carried out according to optional step e), the starting material used is a substance mixture which has an enantiomer excess of more than 99.4%. Within the context of a further preferred embodiment of the method according to the invention, the starting material used is a substance mixture which consists to at least 98% by weight of menthol (L- or else D-menthol, preferably L-menthol) and in total to up to 2% by weight (in each case based on the mixture) of diastereomers of menthol and/or isopulegol and diastereomers thereof (in each case in the D or L form) and/or isomenthone or menthone and/or other components, such as alcohols, ketones, aldehydes, hydrocarbons or water, where the content of menthone and/or isomenthone and the content of other components is in each case less than 1% by weight (based on the mixture).

The distillative separation to be carried out if desired in the course of step e) is usually carried out by separating off the menthol used, preferably L-menthol-comprising substance mixture, into, in each case, one or more low-boiler, medium-boiler and high-boiler fraction or fractions, and removing menthol, preferably L-menthol in pure or enriched form, in liquid or gaseous form as a medium-boiler fraction at the side take-off point of the dividing wall column used.

The method to be carried out if desired in the course of step e) is accordingly also a continuous method for isolating menthol, preferably L-menthol, preferably a continuous method for isolating menthol in pure or enriched form by distillative separation of menthol from substance mixtures comprising menthol and its diastereomers as described above, where the distillative separation is carried out in a dividing wall column having 50 to 300 theoretical plates and one or more side take-off points at an absolute operating pressure of from 5 to 500 mbar.

The dividing wall column to be used for this has a total number of plates of from 50 to 300, preferably 100 to 200 and very particularly preferably 120 to 180 theoretical plates, and one or more, preferably 1 to 3, in particular 1 or 2 and very particularly preferably 1 side take-off point or side take-off points.

The method to be carried out preferably according to optional step e) is carried out at an absolute operating pressure in the dividing wall column of from 5 to 500 mbar, preferably of from 10 to 200 mbar, particularly preferably of from 20 to 120 mbar and very particularly preferably of from 20 to 100 mbar and especially preferably at an absolute operating pressure of from 40 to 100 mbar. Preferably, the dividing wall column is operated in such a way that the absolute top pressure is 10 to 100 mbar, particularly preferably 10 to 80 mbar, very particularly preferably 10 to 60 mbar, even more preferably 20 to 60 mbar and especially preferably 40 to 60 mbar. Likewise preferably here, the dividing wall column is operated such that the absolute bottom pressure is 20 to 500 mbar, particularly preferably 30 to 200 mbar or better up to 100 mbar, even more preferably 40 to 200 mbar or better up to 100 mbar and very particularly preferably 50 to 100 mbar.

The reflux ratio when carrying out the preferred separating method according to step e) can be varied within wide limits and is usually about 5:1 to about 2000:1, preferably about 20:1 to 1000:1 and particularly preferably about 50:1 to about 500:1. Also advantageous is a dephlegmator procedure, i.e. only the return stream is condensed in the top condenser of the column and returned to the column. In such an energetically favorable case of partial condensation, the top product to be discharged is produced exclusively in the aftercooler, which can be operated at a lower temperature. It is advantageous here to provide a heat carrier circulation system such that the temperature of the cooling medium in the aftercooler can be controlled within a range from 5° C. to about 50° C., in order, if appropriate, to be able to remelt solids formed by desublimation from time to time.

For this reason, it is also advantageous to provide a means of feeding the main condenser and/or the postcondenser of the column with a heat carrier medium (cooling medium) whose temperature can be controlled from 0° C. to 60° C., preferably from 20 to 60° C. For this purpose, for example, water can be pumped in circulation through the heat exchanger with the aid of a centrifugal pump, and a temperature control system can be used if required to feed cold or hot water into this pumped circulation system. Of course, electrical heating of this circuit with a flow heater incorporated into the circuit, or conventional heating with steam are also possible.

By virtue of the separating method preferred according to the invention in accordance with optional step e), menthol, preferably L-menthol in pure or enriched form is obtainable. The term "menthol in enriched form" is to be understood as meaning menthol, preferably L-menthol-containing substance mixtures which have a higher content of menthol or L-menthol than the substance mixture which comprises menthol or preferably L-menthol that is to be used in each case according to the invention. Preferably, the term "menthol in enriched form" is to be understood as meaning menthol, preferably L-menthol, which has a purity, i.e. a content, of more than 80 to 99.5% by weight, preferably from 85 to 99.5% by weight, particularly preferably of 90% by weight or even more, preferably of 95% by weight to 99.5% by weight. The method preferred in the course of step e) also permits the production of menthol, preferably L-menthol in pure form. The term "menthol in pure form" is understood as meaning menthol, preferably L-menthol, with a content of greater than or equal to 99% by weight, preferably greater than or equal to 99.1% by weight, preferably of at least 99.2% by weight, further preferably of at least 99.3% by weight, even more preferably of at least 99.4% by weight and especially preferably of at least 99.5% by weight, again preferably of at least 99.6% by weight, further preferably of at least 99.7% by weight and most preferably of 99.8% by weight to 99.99% by weight, preferably up to 99.98% by weight, particularly preferably up to 99.97% by weight, even more preferably up to 99.96% by weight and most preferably up to 99.95% by weight. Here, the data in % by weight, like all data in % by weight within the context of the present invention, are based on the total amount of the respective mixture.

The feed, i.e. the substance mixture to be used can be fed in liquid or gaseous form to the dividing wall column and be separated there into a top and bottom fraction, and also one or more side discharges, preferably one side discharge. In one side discharge, the menthol product of value, preferably L-menthol, is produced in the desired purity, i.e. in enriched or pure form. In one particular embodiment of the preferred method for producing pure or enriched menthol, a postcondenser is connected downstream of the top condenser of the column and, as explained above, is cooled with a cooling liquid whose temperature can be controlled within the temperature range from 0 to 60° C., preferably from 20 to 60° C. (for example with glycol-containing water), and a low-menthol low-boiler fraction is also produced therein.

Method variants for the continuous distillative fractionation of multisubstance mixtures are explained above within the context of the method for producing neral in pure or enriched form by distillatively separating off neral from substance mixtures comprising neral and geranial.

FIG. 1 shows a preferred embodiment of the separation, to be carried out preferably according to the invention in the course of step e), of the menthol-comprising substance mixture to be used into a low-menthol top fraction (j), a menthol-rich side fraction (f) and a bottom fraction (g). The menthol-containing feed to the dividing wall column can take place in liquid form (b), in gaseous form (c), or in gaseous and liquid form.

The method preferred according to the invention in accordance with optional step e) is preferably carried out continuously. Consequently, the substance mixtures which comprise menthol, preferably L-menthol, and are to be used as the starting material are preferably fed continuously to the dividing wall column, and the products (fractions) and by-products obtained according to the invention are preferably discharged continuously.

A further condenser is usually connected downstream of the column to be used for this purpose, and its working temperature is 10 to 40 K, preferably 20 to 30 K, below the working temperature of the top condenser of the dividing wall column. With the aid of this, a majority of the low boilers still present in the top stream (k) can be precipitated.

Moreover, in the case of dividing wall columns, it may be advantageous to subject the feed stream to a preliminary evaporation and then to feed it to the column in biphasic form or in the form of two streams. This preliminary evaporation is appropriate particularly when the feed stream comprises relatively large amounts of low boilers. As a result of the preliminary evaporation, the stripping section of the column can be significantly deburdened.

The dividing wall columns to be used preferably in the course of step e) can be designed either as packed columns with random packings or structured packings, or as tray columns. In the method preferred according to the invention for producing menthol in pure or enriched form, it is advisable to use packed columns. In this context, structured sheet metal or fabric packings with a specific surface area of about 100 to 750 $m^2/m^3$, preferably about 350 to 500 $m^2/m^3$, are particularly suitable.

If, as in the case of the present separation, particularly high demands are placed on the purities of the products, it is favorable to equip the dividing wall with thermal insulation. A description of the various means of thermal insulation of the dividing wall can be found in EP-A 0 640 367. A double-wall design with an intermediate narrow gas space is particularly favorable.

When separating multisubstance mixtures into a low-boiler fraction, medium-boiler fraction and high-boiler fraction, specifications usually exist regarding the maximum permissible proportion of low boilers and high boilers in the medium-boiler fraction. In this connection, either individual components which are critical for the separating problem, so-called key components, or the sum of a plurality of key components, are specified. These key components within the context of the present invention are isomenthol as high-boiling secondary component, and neomenthol or a mixture of neo- and neoisomenthol as low-boiling secondary component.

Compliance with the specification for the high boilers in the medium-boiler fraction can be controlled, for example, via the division ratio of the liquid at the upper end of the dividing wall. In this connection, the division ratio of the liquid at the upper end of the dividing wall is preferably adjusted such that the concentration of the key components for the high-boiler fraction in the liquid at the upper end of the dividing wall constitutes 10 to 80%, preferably 30 to 50%, of the value which is to be achieved in the side take-off product. The liquid division is preferably adjusted to the effect that in the case of higher contents of key components in the high-boiler fraction, more liquid is passed to the feed section, and in the case of lower contents of key components in the high-boiler fraction, less liquid is passed to the feed section.

Accordingly, the specification for the low boilers in the medium-boiler fraction can be controlled by the heating output. In this connection, for example, the heating output in the evaporator is adjusted such that the concentration of key components in the low-boiler fraction in the liquid at the lower end of the dividing wall constitutes 10 to 80, preferably 30 to 50% of the value which is to be achieved in the side take-off product, and the heating output is preferably adjusted to the effect that in the case of a higher content of key components in the low-boiler fraction, the heating output is increased, and in the case of a lower content of key components in the low-boiler fraction, the heating output is reduced.

To compensate for disturbances in the feed amount or in the feed concentration, it has moreover proven to be advantageous, by means of a corresponding control mechanism, for example by means of suitable control specifications, in the process control system, to ensure that the flow rates of the liquids which to the column sections (2), i.e. the rectifying section of the feed section, and (5), i.e. the stripping section of the removal section, cannot drop below 30% of their normal value.

For the removal and division of the liquids at the upper end of the dividing wall and at the side removal point, both internal collecting spaces and those arranged outside the column are suitable for the liquid, these assuming the function of a pump reservoir or ensuring a sufficiently high static liquid height, which enable controlled further conduction of liquid by means of control elements, for example valves. When using packed columns, the liquid is first captured in collectors and passed from there into an internal or external collecting space.

Within the context of one particularly preferred embodiment, the separating method preferred according to the invention according to optional step e) is carried out in a plant as shown diagrammatically in FIG. 1. The preferred embodiment is notable for the fact that a dividing wall column (TK) is used which has a dividing wall (T) in the longitudinal direction of the column to form an upper common column region (1), a lower common column region (6), a feed section (2, 4) with rectifying section (2) and stripping section (4), and also a removal section (3, 5) with stripping section (3) and rectifying section (5).

The menthol-comprising substance mixture (a) serving as feed material is preferably fed to the middle region of the feed section (2, 4), the menthol, preferably L-menthol, in pure or enriched form is obtained as side take-off from the middle region of the removal section (3, 5), and one or more low-boiler fractions are removed from the upper common column region (1), and one or more high-boiler fractions are removed from the lower common column region (6).

The feed stream (a) can be introduced into the column (TK) via a preheater (VH) as a liquid (b), gaseous (c) or partially liquid and gaseous stream. The top stream of the column is completely or partially condensed in the condenser (K). In the case of partial condensation (dephlegmator operation), the offgas stream (k) of the top condenser (K) usually still comprises noticeable amounts of condensible low boilers, which can then be precipitated in a postcondenser operated at low temperature.

The top condenser (K) and/or the postcondenser may, for example, be designed as a plate apparatus and be integrated into the column jacket, preferably into the top of the column. To prevent solids formation, it may be advantageous to control the temperature of the condenser of the column, for example to temperatures of about 30 to about 50° C.

The top product precipitated in the condenser (K) is buffered in the distillate vessel (DB) and fed back to the column as the column return stream (i) by means of the return pump (RP). If required, a distillate fraction (j) can also be obtained therefrom. In the case of integration of the condenser into the top of the column, it is possible to dispense with the distillate vessel (DB) and the return pump (RP).

The bottom stream is advantageously fed to the bottom evaporator (SV) via the circulation pump (UP), which is preferably configured as a falling film evaporator. The bottoms discharge (g) of the column (TK) can also be withdrawn from this pumped circulation stream. Advantageously, the bottom stream (high-boiler fraction) of the column is removed as liquid stream (h) downstream of the bottom evaporator, optionally with the aid of a smaller pump (SP).

The bottom evaporator used for the dividing wall column may advantageously be a thin film apparatus, for example a falling film evaporator.

The product of value, i.e. menthol or L-menthol in pure or enriched form can be drawn off as liquid side take-off, stream (f), from the removal section of the dividing wall column (TK). It is also possible, if required, to remove the product of value stream (f) as a gaseous side-takeoff, although usually a further condenser is then required. On account of the melting point of L-menthol in pure or enriched form between 41 and 44° C., it is advantageous to insulate all product-conducting apparatuses (besides the column, also all containers and pumps) and lines, and also preferably all apparatuses and lines of the vacuum system, i.e. to insulate them thermally with suitable materials and to provide them with trace heating. In this connection, for example, electrical heating lines enclosed in the pipes, which are controlled using suitable instruments to temperatures of up to 70° C., preferably of 45 to 70° C., even more preferably to temperatures up to 60° C., especially preferably from 45 to 60° C., are advantageous. Alternatively, it is also possible to use conventional trace heating systems, such as, for example, jacketed tubes with warm water flowing through the jacket.

The upper common subregion (1) of the column usually has 5 to 50%, the rectifying section (2) of the feed section of the column 5 to 50%, the stripping section (4) of the feed section of the column 2 to 50%, the stripping section (2) of the removal section of the column 5 to 50%, the rectifying section (5) of the removal section 2 to 50%, and the common lower section (6) of the column 5 to 50%, of the total number of theoretical plates of the column, where the selected percentages add up to 100%.

Preferably, the upper common subregion (1) of the column has 10 to 25%, the rectifying section (2) of the feed section of the column 15 to 30%, the stripping section (4) of the feed section of the column 15 to 30%, the stripping section (2) of the removal section of the column 15 to 30%, the rectifying section (5) of the removal section 15 to 30%, and the common lower section (6) of the column 10 to 25%, of the total number of theoretical plates of the column, where the selected percentages add up to 100%.

The sum of the number of theoretical plates of subregions (2) and (4) in the feed section is preferably 80 to 110%, particularly preferably 95 to 105%, of the sum of the number of plates of subregions (3) and (5) in the removal section.

Within the context of one preferred embodiment of the preferred separating method according to step e), the feed point and the side take-off point are arranged, with regard to the position of the theoretical plates, at different heights in the column, in that the feed point is arranged 1 to 40, preferably 5 to 20, theoretical plates higher or lower than the side take-off point.

It has moreover proven to be advantageous if the subregion of the column which is divided by the dividing wall and consists of the subregions (2), (3), (4) and (5) or sections thereof is equipped with structured packings or random packings (for example fabric packings such as Montz A3-500, Sulzer BX or CY or sheet metal packings such as Montz B1-500 (Montz) or Mellapak (Sulzer).

The vapor stream at the lower end of the dividing wall can be adjusted through the selection and/or dimensioning of the separating internals and/or the incorporation of devices which generate a pressure drop, for example restrictors, such that the ratio of the vapor stream in the feed section to that of the removal section is 0.8:1.2, preferably 0.9:1.1.

The liquid effluxing from the upper common section (1) of the column is advantageously collected in a collecting space arranged within the column or outside of the column and is divided in a targeted manner by a fixed setting or control system at the upper end of the dividing wall such that the ratio of the liquid stream to the feed section to that to the removal section is 0.1:2.0 in the case of a predominantly liquid feed and 1.0:2 in the case of a gaseous feed. Here, the liquid feed is preferred according to the invention.

The liquid effluxing from the upper common subregion (1) to the feed section can be conveyed by means of a pump or introduced with quantitative control via a static feed height of at least 1 m, preferably by means of a cascade control system in conjunction with the liquid level control system of the collecting space. The control system is preferably adjusted such that the amount of liquid introduced to the feed section cannot drop below 30% of the desired normal value. Moreover, the division of the liquid effluxing from the subregion (3) in the removal section of the column to the side take-off and to the subregion (5) in the removal section of the column is advantageously adjusted by means of a control system such that the amount of liquid introduced to the subregion (5) cannot drop below a level of 30% of the desired normal value. The normal values here are advantageously assumed to be twice to four times the amount, based on the feed rate.

The dividing wall column preferably has, at the upper and lower ends of the dividing wall, sampling means; samples can be taken in liquid or gaseous form from the column, continuously or at time intervals, and can be examined with regard to their composition, preferably by gas chromatography.

The division ratio of the liquid at the upper end of the dividing wall is preferably adjusted such that the concentration of those components of the high-boiler fraction for which a particular concentration limit is to be achieved in the side take-off (specifically isomenthol) in the liquid at the upper end of the dividing wall constitutes 10 to 80% of the value which is to be achieved in the side take-off product. The liquid division should preferably be adjusted to the effect that in the case of higher contents of components of the high-boiler fraction, more liquid is passed to the feed section, and in the case of lower contents of components of the high-boiler fraction, less liquid is passed to the feed section.

The heating output in the evaporator (SV) is preferably adjusted such that the concentration of those components of the low-boiler fraction for which a particular concentration limit is to be achieved in the side take-off (specifically neoisomenthol) in the liquid at the lower end of the dividing wall constitutes 10 to 80% of the value which is to be achieved in the side take-off product. The heating output is advantageously adjusted to the effect that in the case of a higher content of components of the low-boiler fraction, the heating output is increased, and in the case of a lower content of components of the low-boiler fraction, the heating output is reduced.

The distillate removal, i.e. the removal of the low-boiling by-products takes place preferably with temperature control or else with quantitative control, depending on the amount of lower-boiling secondary components which are present in the feed mixture and are to be separated off. The control temperature used is advantageously a measurement site in the subregion (1) of the column which is arranged 3 to 10, preferably 4 to 6, theoretical plates below the upper end of the column.

The bottom product is preferably removed with temperature control or else with quantitative control, depending on the feed rate.

The removal of the menthol, preferably L-menthol, method product obtained as side product in pure or enriched form preferably takes place with level control, the control parameter used preferably being the liquid level in the column bottom.

The feed stream of the menthol-containing substance mixture to be used according to the invention is preferably partly or completely pre-evaporated and fed to the column in biphasic form or in the form of a gaseous stream and of a liquid stream.

Within the context of one preferred embodiment, in the course of optional step e) of the method according to the invention too, a dividing wall column is used, the dividing wall of which is not welded into the column, but is configured in the form of loosely inserted and adequately sealed subsegments.

The liquid division in the individual subregions of the column can preferably be adjusted inhomogeneously in a targeted manner, the liquid being introduced to an increased extent in the wall region especially in the subregions (2) and (5), and being introduced to a reduced extent in the wall region in subregions (3) and (4).

The division ratio of the return liquid between removal side and feed side of the dividing wall is preferably about 1:1 to about 3:1, preferably about 1:1 to about 2:1.

The position of the dividing wall in the individual subregions of the column can advantageously be adjusted such that the cross sections of feed and removal sections have different areas.

The L-menthol in pure or enriched form obtainable according to the invention can be obtained preferably continuously via the side take-off, or in the case that further side take-offs are provided, via the middle side take-off (f), and has, within the context of one preferred embodiment, a menthol content of more than 99.5% by weight, preferably of 99.5 to 99.95% by weight, and a content of the other diastereomers of menthol as described above of up to 0.3% by weight (in each case based on the product obtained), possibly in addition to very small amounts of further impurities.

Within the context of a further preferred embodiment, the menthol obtained according to the invention, preferably L-menthol in pure or enriched form, preferably in pure form, has a content of isopulegol and the diastereomers thereof as described above of together up to 0.5% by weight, preferably up to 0.3 and particularly preferably up to 0.1% by weight (based on the total amount of the product obtained). Within the context of a further preferred embodiment, the menthol obtained according to the invention, preferably L-menthol in pure or enriched form, preferably in pure form, has a content of menthone and isomenthone of up to 0.5% by weight, preferably up to 0.3 and particularly preferably up to 0.1% by weight (based on the total amount of the product obtained).

A further aspect of this optional step e) of the present invention relates to a device for carrying out the continuous distillation method as described above for producing racemic or optically active menthol in pure or enriched form.

The device according to the invention is shown in FIG. 1 and comprises a dividing wall column (TK) with 50 to 300 theoretical plates and one or more side take-off points, which has a dividing wall (T) in the longitudinal direction of the column to form an upper common column region (1), a lower common column region (6), a feed section (2, 4) with rectifying section (2) and stripping section (4), and a removal section (3, 5) with stripping section (3) and rectifying section (5), where all of the product-conducting constituents of the device (besides the column, also all containers, pumps and lines) and also preferably all apparatuses and lines of the vacuum system are thermally insulated with suitable materials and provided with trace heating.

In this connection, as already described above, electrical heating lines enclosed in tubes, for example, are advantageous, which are controlled with suitable instruments to temperatures of up to 70° C., preferably of 45 to 70° C., even more preferably to temperatures up to 60° C., especially preferably of 45 to 60° C. Alternatively, it is also possible to use conventional trace heating systems, such as, for example, jacketed tubes with warm water flowing through the jacket.

The above-described steps a) to d) and also the optional, i.e. additionally to be carried out if desired, steps 0) and e) open up, from the point of view of cost and processing, a very advantageous route to high-purity menthol. If desired, optically active or racemic menthol can be produced. Consequently, in one preferred embodiment, the present invention also relates to a method for producing optically active menthol, comprising the steps a.2) asymmetric catalytic hydrogenation of neral and/or geranial to give optically active citronellal,
b.2) cyclization of optically active citronellal obtained according to step a.2) to give optically active isopulegol in the presence of an acidic catalyst,
c.2) purification of optically active isopulegol obtained according to step b.2) by crystallization and
d.2) catalytic hydrogenation of optically active isopulegol obtained according to step c.2) to give optically active menthol.

According to step a.2), an asymmetric hydrogenation of neral and/or geranial, i.e. of neral of the formula (II) or geranial of the formula (III) or neral- and geranial-comprising substance mixtures as described above is carried out. Preferably, an asymmetric catalytic hydrogenation, as described above under step a), of pure or enriched neral is carried out. In an again preferred embodiment, this asymmetric catalytic hydrogenation according to step a.2) is carried out after the optional step 0) for producing pure or enriched neral by distillative separation of neral from substance mixtures comprising geranial and neral. In this way, optically active citronellal is accessible, if desired, depending on the configuration of the asymmetric catalytic hydrogenation, in the form of one of the two enantiomers, preferably in the form of D-citronellal.

The optically active citronellal obtainable according to step a.2) can then be cyclized according to step b.2) to give optically active isopulegol in the presence of an acidic catalyst. Suitable acidic catalysts which may be mentioned are the acidic or Lewis-acidic catalysts described above in step b), in particular the specified aluminum-containing Lewis-acidic catalysts, such as the diarylphenoxyaluminum compounds preferred according to the invention which are obtainable by reacting the aforementioned ligands of the formula (I) with specific aluminum compounds, such as, for example, trimethyl- or triethylaluminum.

The optically active isopulegol obtainable in this way is, according to step c.2) within the context of this preferred embodiment, purified by crystallization. In this connection, it is in principle possible to use crystallization methods from solution and also from the melt that are known per se to the person skilled in the art. Preference is given to carrying out a crystallization from the melt as described under step c), particularly preferably a static melt crystallization and very particularly preferably a static layer crystallization as described above. Within the context of this preferred embodiment of the method according to the invention, purified, i.e. enantiomer- and diastereomer-enriched isopulegol, preferably L-isopulegol, as described above is obtained.

Within the context of this embodiment of the method according to the invention, according to step d.2) the optically active isopulegol obtainable in this way is then catalytically hydrogenated to give optically active menthol. The catalytic hydrogenation of isopulegol to menthol is known to the person skilled in the art and can be carried out using a wide variety of customary heterogeneous hydrogenation catalysts. It has proven to be advantageous to carry out the catalytic hydrogenation in the presence of the nickel-, copper-, zirconium- and molybdenum-containing catalysts described above under step d) since in this case undesired by-products, such as the above-described diastereomers of menthol or the menthones are formed only to the smallest possible extent, which is of importance particularly for the odor and taste properties of the product obtained in this way.

According to a further preferred embodiment, the present invention relates to a method for producing enantiomer-enriched optically active menthol and racemic or enantiomer-depleted menthol, comprising the steps a.3) asymmetric catalytic hydrogenation of neral and/or geranial to give optically active citronellal with an enantiomer excess in the range from 70 to 99%,
b.3) cyclization of optically active citronellal obtained according to step a.3) to give optically active isopulegol in the presence of an acidic catalyst,
c.3) purification of optically active isopulegol obtained according to step b.3) by crystallization to give enantiomerically enriched isopulegol and (either) racemic or enantomerically depleted isopulegol and
d.3) catalytic hydrogenation of enantiomerically enriched optically active isopulegol obtained according to step c.3) to give optically active menthol and catalytic hydrogenation of racemic or enantiomerically depleted isopulegol to give racemic or enantomerically depleted menthol.

According to step a.3) of this preferred embodiment of the method according to the invention, an asymmetric catalytic hydrogenation, as described for example above under step a), of neral or geranial to give optrically active citronellal with an enantiomer excess in the range from 70 to 99%, preferably 80 to 99% ee and particularly preferably 85 to 95% ee, is carried out. For this, preference is given to using neral, particularly preferably neral accessible as described above under optional step 0) in enriched or pure form. A suitable catalyst system for carrying out the asymmetric, i.e. enantioselective hydrogenation has proven to be in particular the above-described catalyst formed from a rhodium compound soluble in the reaction mixture and in particular the chiral ligands (R,R)-chiraphos or (S,S)-chiraphos, preferably (R,R)-chiraphos. Preferably, the catalyst to be used is pretreated with a gas mixture comprising carbon monoxide and hydrogen and/or the hydrogenation is carried out in the presence of carbon monoxide additionally fed to the reaction mixture, as described in WO 2006/040096. Moreover, as described under step a), it has proven to be advantageous to separate off excess carbon monoxide following the pretreatment of the catalyst, and to carry out the asymmetric hydrogenation in the presence of hydrogen with a carbon monoxide content of from 100 to 1200 ppm.

The enantiomer excess of the citronellal obtainable in this way can be controlled here via the purity of the neral used, in particular via the content of geranial in the neral to be used since, under the selected reaction conditions, for example during the asymmetric hydrogenation, as described above under step a), of neral in the presence of a catalyst formed from a rhodium compound and (R,R)-chiraphos, neral is converted to the desired D-citronellal with high asymmetric induction, whereas the other enantiomer L-citronellal is formed from the possibly present geranial.

The optically active citronellal obtainable in this way with an enantiomer excess of 70 to 99%, preferably 80 to 99% ee and particularly preferably 85 to 95% ee is then cyclized according to step b.3) to give optically active isopulegol in the presence of an acidic catalyst, preferably by the method described above under step b) and also in WO 2006/092433, in the presence of diarylphenoxyaluminum compounds. This generally gives, largely without loss of the absolute stereochemical information of the optically active citronellal used, optically active isopulegol which is usually already notable for a high diastereomer purity.

According to step c.3) of this preferred embodiment of the method according to the invention, a purification of the optically active isopulegol obtained in this way is carried out by crystallization to give enantiomer-enriched isopulegol and either racemic or enantiomer-depleted isopulegol. The crystallization can be carried out here by methods known to the person skilled in the art, for example as solution crystallization. However, preference is given to carrying out a melt crystallization as described above under step b), particularly preferably in the form of a static layer crystallization. Here, it is possible to further purify the optically active isopulegol obtained according to step b.3), particularly with regard to the enantiomer and diastereomer purity. Besides enantiomer-enriched optically active isopulegol of high enantiomer purity, enantiomer-depleted or racemic isopulegol as described above under step b) is also obtained. Both products obtained in this way can be passed to separated further treatment.

According to step d.3) of this embodiment of the method according to the invention, a catalytic hydrogenation of enantiomer-enriched optically active isopulegol to enantiomer-enriched optically active menthol and a catalytic hydrogenation of racemic or enantiomer-depleted isopulegol to give racemic or enantiomer-depleted menthol is carried out. The two hydrogenations are carried out separately so as to avoid any back-mixing of the enantiomer-enriched and racemic or enantiomer-depleted streams separated by the preceding crystallization. In this connection too, various catalyst systems are available to the person skilled in the art for the catalytic hydrogenation of the ethylenic double bond of isopulegol, as described under step d). However, as already mentioned above under step d), it has proven to be advantageous to carry out the catalytic hydrogenation in the presence of the nickel-, copper, zirconium- and molybdenum-containing catalysts described above under step d), particularly if a high enantiomer and diastereomer purity of the product is desired.

One embodiment which is particularly preferred within the context of the present invention relates to a method for producing L-(−)-menthol, comprising the steps
a.4) asymmetric catalytic hydrogenation of neral to give D-(+)-citronellal,
b.4) cyclization of D-(+)-citronellal obtained according to step a.4) to give L-(−)-isopulegol in the presence of an acidic catalyst,
c.4) purification of L-(−)-isopulegol obtained according to step b.4) by crystallization and
d.4) catalytic hydrogenation of L-(−)-isopulegol obtained according to step c.4) to give L-(−)-menthol.

The starting material used for carrying out this preferred embodiment of the method according to the invention is neral, preferably that in pure or enriched form, as can be produced, for example, by the optional step 0) described above from geranial- and neral-containing mixtures. An again preferred variant of this embodiment accordingly additionally comprises step 0) for producing neral in pure or enriched form by distillative separation of neral- and geranial-containing substance mixtures.

According to step a.4), neral is converted by catalytic asymmetric hydrogenation to D-(+)-citronellal, i.e. (R)-citronellal, preferably by the method described above under step b) using (R,R)-chiraphos as chiral ligand and particularly preferably in the presence of carbon monoxide. Through the cyclization method as described under step b) in the presence of an acidic, preferably Lewis-acidic, aluminum-containing catalyst, such as, for example, those described in EP-A-1 225 163, or the preferred diarylphenoxyaluminum compounds, according to step b.4) L-(−)-isopulegol is obtained from D-(+)-citronellal. This can, as described above, be purified by crystallization, preferably by melt crystallization according to step c.4) and then, according to step d.4), be converted to L-(−)-menthol by catalytic hydrogenation as described above.

One embodiment that is very particularly preferred within the context of the present invention relates to a method for producing L-(−)-menthol and racemic or enantiomer-depleted menthol, comprising the steps
a.5) asymmetric catalytic hydrogenation of neral to give D-(+)-citronellal with an enantiomer excess of from 70 to 99%,
b.5) cyclization of D-(+)-citronellal obtained according to step a.5) to give L-(−)-isopulegol in the presence of an acidic catalyst,
c.5) purification of L-(−)-isopulegol obtained according to step b.5) by crystallization to give enantiomerically enriched L-(−)-isopulegol and (either) racemic or enantiomerically depleted isopulegol and
d.5) catalytic hydrogenation of enantiomerically enriched L-(−)-isopulegol obtained according to step c.5) to give L-(−)-menthol and catalytic hydrogenation of racemic or enantiomer-depleted isopulegol obtained according to step c.5) to give racemic or enantiomerically depleted menthol.

The method according to this embodiment permits the production of enantiomer-enriched optically active L-menthol and of racemic or enantiomer-depleted menthol which are obtained alongside one another as method products in high chemical purity. The starting material used is in turn neral, preferably that as can be obtained by the optional additional step 0). Within the context of an again preferred embodiment, the method for producing L-(−)-menthol and racemic or enantiomer-depleted menthol accordingly also comprises step 0) as described above concerning the production of neral in pure or enriched form by distillative separation of neral from neral- and geranial-containing mixtures, preferably using a dividing wall column as described above having 80 to 200 theoretical plates at an absolute operating pressure of from 5 to 200 mbar.

According to step a.5) of this embodiment, an asymmetric catalytic hydrogenation, as described above, of neral to D-(+)-citronellal with an enantiomer excess of from 70 to 99%, preferably 80 to 99% ee and particularly preferably 85 to 95% ee, is carried out. The D-(+)-citronellal obtained in this way is then cyclized, according to step b.5), to give L-(−)-isopulegol in the presence of an acidic catalyst as described above, preferably in the presence of a Lewis-acidic, aluminum-containing catalyst.

Then, for the purification of L-(−)-isopulegol to step c.5), the crystallization already described, preferably melt crystallization, is carried out, giving, alongside one another, enantiomer-enriched L-(−)-isopulegol and racemic or enantiomer-depleted isopulegol, i.e. isopulegol with an enantiomer excess of up to 15%, preferably of up to 10% ee, particularly preferably of up to 7% ee and very particularly preferably of up to 5% ee.

Finally, according to step d.5) of this particularly preferred embodiment of the method according to the invention, a catalytic hydrogenation of enantiomer-enriched L-(−)-isopulegol obtained according to step c.5) to give L-(−)-menthol, and a catalytic hydrogenation of racemic or enantiomer-depleted isopulegol likewise obtained according to step c.5) to give racemic or enantiomer-depleted menthol, as described above, are carried out.

The racemic or enantiomer-depleted menthol obtainable in this way can, corresponding to the enantiomer excess of the racemic or enantiomer-depleted isopulegol used, as defined above, likewise have an enantiomer excess of up to 15%, preferably of up to 10% ee, particularly preferably of up to 7% ee and very particularly preferably of up to 5% ee.

The racemic or optically active menthol, specifically L-menthol, obtained in the course of this preferred embodiment of the method according to the invention can then, if desired, be further purified in order to yet further increase the purity of the obtained method products. Accordingly, the embodiments described above can in each case also comprise as an additional step the optional step e), relating to a continuous method for producing optically active or racemic menthol in pure or enriched form by distillative separation of optically active or racemic menthol from substance mixtures comprising racemic or optically active menthol and diastereomers of menthol, the separation being carried out in a dividing wall column having 50 to 300 theoretical plates and one or more side take-off points at an absolute operating pressure of from 5 to 500 mbar.

The method according to the invention produces, in one preferred embodiment, L-(−)-menthol with a chemical purity of at least 99% by weight, preferably of from 99.5 to 99.99% by weight, especially preferably from 99.5 to 99.9% by weight and an enantiomer excess of at least 99%, preferably of from 99.5 to 99.9% ee.

The racemic or optically active menthol, preferably L-menthol, obtainable by the method according to the invention can be further utilized or sold in all forms known to the person skilled in the art, generally in the form of partially or completely solidified melts or in compacted form, e.g. as flakes, pressed articles, pellets, droplets and the like. Methods for compacting menthol are known to the person skilled in the art. For example, the simple flaking on a flaking roller is described, for example, in U.S. Pat. No. 3,023,253.

WO 2003/101924 discloses menthol pressed articles with a content of alpha-menthol of at least 70% by weight, and also a method for the production thereof.

A granulation method for producing spherical menthol particles is known, for example, from WO 2007/071512. Here, molten menthol is introduced directly into water at a temperature of from 0 to 12° C.

In the case of the racemic or enantiomer-depleted menthol as described above, the melt has proven especially useful as the most commonly handled form on account of the lower melting point in the range from 28 to 30° C.

By contrast, optically active menthol, preferably L-menthol as described above in pure form is preferably further used or sold in compacted form on account of better handling properties.

The method according to the invention opens up a particularly cost-effective route to optically active and racemic or enantiomer-depleted menthol, where the products obtained in the process are accessible in a small total number of stages, high yield and high quality corresponding to the quality requirements of many pharmacopeia. The starting material here is geranial or neral or preferably mixtures of geranial and neral. A starting material that is particularly preferred according to the invention is citral, which is readily available on an industrial scale and which, for its part, can be produced from the basic chemicals isobutene or isoprenol and prenol on practically any scale and independently of natural sources.

A particular advantage of the method according to the invention that should be emphasized is that it opens up the route to optically active, preferably practically enantiomerically and diastereomerically pure L-menthol and to racemic or enantiomer-depleted menthol. The quantitative ratio of the optically active or racemic or enantiomer-depleted products obtained according to the invention can be controlled here, if desired, via the composition of the neral- and geranial-containing substance mixture used. Thus, a higher content of neral in the asymmetric hydrogenation leads to a higher enantiomer excess of the optically active citronellal formed, whereas the yield of optically active isopulegol during the subsequent melt crystallization, during which optically active isopulegol is separated from racemic isopulegol, increases.

The examples below serve to illustrate the invention without limiting it in any way:

DISTILLATIVE SEPARATION OF NERAL-AND GERANIAL-CONTAINING MIXTURES

Example 1

The dividing wall column used for the following examples was constructed from five glass sections, each of length 1.2 m, with an internal diameter of 64 mm. A dividing wall made of sheet metal was inserted into the three middle sections. Above and below the dividing wall region, laboratory packings (Sulzer CY) were installed and, in the dividing wall region, metal fabric rings made of stainless steel with a diameter of 5 mm. In separating performance measurements which were carried out with the xylene isomer mixture at a top pressure of 60 mbar, an overall separating performance of 100 theoretical plates over the entire column and about 55 theoretical plates in the dividing wall region was measured. The total number of theoretical plates present was thus about 155. The column was equipped with an oil-heated thin film evaporator (0.1 m²) and a condenser cooled with cooling water.

Temperatures at different levels in the column and the top pressure and the pressure drop over the column were measured by means of a measurement recording system. The column had flow meters in the inlets and outlets, and also a return flow meter, the measurement of which served as the control parameter for the inlet temperature of the oil thermostat. This control system ensured a constant return rate, which also established a constant pressure difference. The division of the amount of liquid above the dividing wall between feed section and removal section of the dividing wall was realized by means of a swivel funnel on a time cycle.

At a height of 136 cm from the feed section of the dividing wall, 461 g/h of a liquid mixture, preheated to 110° C., of 48.7 GC area % neral, 47.8 GC area % geranial and 1.4 GC area % other citral isomers was fed to the column. The column was operated at a top pressure of 10 mbar and a return rate of 2.5 kg/h. Here, a pressure drop of about 34 mbar (±1 mbar) was established. At the top of the column, a temperature of 82.3° C. was measured, and in the bottom a temperature of 128.4° C. (±0.5 K). By means of a balance control system, the bottom take-off was fixed to 240 g/h and the distillate take-off to 20 g/h (±1 g/h). The reflux ratio was thus about 125:1. The liquid was divided above the dividing wall in a ratio of 1:1.1 (feed section:removal section). At a height of 490 cm in the removal section of the dividing wall, a gaseous side take-off (f) was removed and condensed in a glass condenser, from which, depending on the bottom fill level, about 200 g/h of pure product was removed by means of a pump.

The fractions obtained were analyzed by gas chromatography with the aid of a standard GC. Gas chromatography analyses were carried out according to the following method:
25 m OV-1, ID.: 0.32 mm, FD.: 0.31 µm; 50° C./2 min-10° C./min to 150° C., 5 min-20° C./min to 280° C./15 min; $t_R$ (citral isomer III): 10.4 min; $t_R$ (citral isomer IV): 10.7 min; $t_R$ (citral isomer V): 11.0 min; $t_R$ (neral I): 12.3 min; $t_R$ (geranial II): 12.6 min The pure product obtained at the side take-off comprised, besides 98.5 GC area % neral, also 0.3 GC area % geranial and 0.65 GC area % other citral isomers. In the bottom take-off, 92.5 GC area % geranial and 6.8 GC area % neral were determined by GC analysis, the distillate comprised 32.1 GC area % neral and 39.6 GC area % other citral isomers.

Example 2

The column described in Example 1 was supplemented by a further, gaseous side take-off (n) in the upper common column section (1), at a height of about 590 cm, which in turn was provided with a side condenser. By means of a balance control system, a removal amount of 15 g/h (±1 g/h) was fixed there.

At a height of 136 cm from the feed section of the dividing wall, 460 g/h of a liquid mixture, preheated to 110° C., of 50.2 GC area % neral, 47.2 GC area % geranial and 0.9 GC area % other citral isomers was fed to the column. The column was operated at a top pressure of 10 mbar and a return rate of 2.5 kg/h. A pressure drop of about 37 mbar (±1 mbar) was established. At the top of the column, a temperature of 68.8° C. was measured, and in the bottom a temperature of 130.1° C. (±0.5 K). By means of a balance control system, the bottom take-off was fixed to 240 g/h and the distillate take-off to about 3 g/h (±1 g/h). The reflux ratio was thus about 600 to 1200:1. The liquid was divided above the dividing wall in a ratio of 1:1.1 (feed section:removal section). At a height of 490 cm in the removal section of the dividing wall, a gaseous side take-off (f) was in turn removed and condensed in a glass condenser, from which, depending on the bottom fill level, about 200 g/h of pure product was removed by means of a pump.

The pure product obtained at the side take-off (f) comprised, besides 98.5 GC area % neral, also 0.3 GC area % geranial and 0.5 GC area % other citral isomers. The upper side take-off comprised, besides 55.5 GC area % neral, 29.5 GC area % other citral isomers. In the bottom take-off, 90.3 GC area % geranial and 8.9 GC area % neral were determined by GC analysis; the distillate comprised only traces of neral and 48.5 GC area % other citral isomers.

Example 3

In a simple glass laboratory column equipped with 6 m of Sulzer CY packing and without dividing wall and without side take-off (theoretical number of plates about 90) with an internal diameter of 50 mm, a mixture of 50.2 GC area % neral, 47 GC area % geranial and 1.3 GC area % other citral isomers was distilled continuously at a top pressure of 5 mbar. The feed amount was 500 g/h, and at the bottom 250 g/h were discharged. The pressure drop over the column was, at a reflux ratio of 11:1, about 28 mbar, the bottom temperature was 121° C. and the top temperature was 81° C.

At the top condenser, at about 20° C., ca. 250 g/h of a liquid distillate with a neral content of 88.1 GC area % and a geranial content of 2.7 GC area % were obtained, the content of other citral isomers in the distillate was in total 7.0 GC area %, which suggests a notable formation of these isomers under distillation conditions.

Examples of Step a): Catalytic Hydrogenation of Neral and/or Geranial to Citronellal Example 4

Asymmetric Hydrogenation of Cis-Citral in the Presence of Carbon Monoxide 17.9 mg of $Rh(CO)_2acac$ and 38.5 mg of (R,R)-chiraphos were dissolved in 20 g of toluene under a protective gas atmosphere and transferred to a 100 ml autoclave which had been flushed beforehand 3 times with a mixture of carbon monoxide and hydrogen (1:1, vol/vol). The mixture was stirred at a 1:1 $CO/H_2$ pressure of 8 bar and 60° C. for 3 h and then cooled to room temperature. By means of a pressure lock, 10.94 g of neral (ratio of the neral/geranial double-bond isomers=99.1:0.9; substrate/catalyst ratio=1000) were then injected with 15 bar of $H_2$. The reaction pressure was adjusted to 80 bar by injecting hydrogen. To reduce the partial CO pressure, the pressure was lowered three times and, after a further 3 h, lowered again to 8 bar and restored to 80 bar by injecting hydrogen. After 18 h, a conversion of 99.9% and a yield of D-citronellal of 99.8% with an optical purity of 90% ee was determined by gas chromatography.

Example 5

Asymmetric Hydrogenation of Neral in the Presence of Carbon Monoxide 17.0 mg of $Rh(CO)_2acac$ and 43.8 mg of (R,R)-chiraphos were dissolved in 0.8 ml of THF and stirred in an autoclave at 80 bar of synthesis gas ($H_2/CO=1:1$, vol/vol) and 60° C. for 8 h. Then, 39.00 g of neral (ratio of the neral/geranial double-bond isomers=95.2:4.8; substrate/catalyst ratio=4000) were dissolved and, together with the catalyst solution, were placed in a 100 ml autoclave which had been flushed beforehand three times with 1:1 $CO/H_2$ (vol/vol). The reaction pressure was adjusted to 80 bar by injecting hydrogen gas which comprised 1000 ppm of carbon monoxide. After 144 h, a conversion of 84.3% and a yield of 80.9% of D-citronellal with an optical purity of 64% ee was determined by gas chromatography.

Example 6

Asymmetric Hydrogenation of Neral with Reuse of the Catalyst 23.7 mg of $Rh(CO)_2$acac and 55.7 mg of (R,R)-chiraphos were dissolved in 24 g of THF under a protective gas atmosphere and placed in a 100 ml autoclave which had been flushed beforehand 3 times with 1:1 $CO/H_2$ (vol/vol). The mixture was stirred at a 1:1 $CO/H_2$ pressure of 80 bar and 60° C. for 3 h. The mixture was then cooled to room temperature and decompressed to a pressure of 8 bar of 1:1 $CO/H_2$. By means of a pressure lock, 13.2 g) of neral (ratio of the neral/geranial double-bond isomers=99.4:0.6) were injected with 15 bar of $H_2$. The reaction pressure was adjusted to 80 bar by injecting hydrogen. To reduce the partial CO pressure, the pressure was lowered 5 times to 8 bar and restored to 80 bar by injecting hydrogen. The content, determined by gas chromatography, of CO in the headspace was 510 ppm. After in each case 20 h and 40 h, a further 13.20 g and 19.80 g, respectively, of neral were added. After 66 h, a conversion of 75.8% and a yield of 72.8% of D-citronellal with an optical purity of 87% ee was determined by gas chromatography.

The overall turnover number based on the yield of D-citronellal was 1030.

Example 7

Asymmetric Hydrogenation of Cis-Citral while Distilling Off the Product and Reusing the Catalyst 8.4 mg of $Rh(CO)_2$acac and 21.6 mg of (R,R)-chiraphos were dissolved in 0.8 ml of THF and stirred in an autoclave at 80 bar of synthesis gas ($H_2/CO=1:1$, vol/vol) and 60° C. for 8 h. Afterward, 9 g of neral (ratio of the neral/geranial double-bond isomers=95.2:4.8) were introduced into the autoclave. The reaction pressure was adjusted to 80 bar by injecting hydrogen gas which comprised 1000 ppm of carbon monoxide. After 24 h, a conversion of 99% was achieved, the ee of the resulting D-citronellal was 83%.

After the product had been distilled off, a further 8.5 g of neral (ratio of the neral/geranial double-bond isomers=95.2:4.8) were added, and hydrogenation was carried out at 80 bar of hydrogen gas which comprised 1000 ppm of carbon monoxide for 48 h. The conversion was 36%, the ee of the resulting D-citronellal was 54%.

After the product had been distilled off once again, a further 6.8 g of neral (ratio of the neral/geranial double-bond isomers=95.2:4.8) were added, and hydrogenation was carried out at 80 bar of hydrogen gas which comprised 1000 ppm of carbon monoxide for 72 h. The conversion was 13%, the ee of the resulting D-citronellal was 30%.

The overall turnover number based on the yield of D-citronellal was 2312.

Example 8

Asymmetric Hydrogenation of Neral with Preformation, Removal of the Product and Reuse of the Catalyst 30 mg of $Rh(CO)_2$acac and 75 mg of (R,R)-chiraphos were dissolved in 3 ml of THF and stirred in an autoclave at 60° C. in the presence of 80 bar of synthesis gas ($H_2/CO=1:1$, vol/vol) for 20 h. Subsequently, 37 g of neral (ratio of the neral/geranial double-bond isomers=96.6:3.4) were added and the solution was introduced into a 100 ml autoclave which had been flushed beforehand three times with 1:1 $CO/H_2$ (vol/vol). The reaction pressure was adjusted to 80 bar by injecting hydrogen gas which comprises 1000 ppm of carbon monoxide. After 24 h, a conversion of >99% was achieved; the ee of the resulting D-citronellal was 87%.

After the product had been distilled off, the distillation residue was diluted with THF and stirred in an autoclave at 60° C. in the presence of synthesis gas ($H_2/CO=1:1$) at a pressure of 80 bar for 20 h. Afterward, a further 32 g of neral (ratio of the neral/geranial double-bond isomers=96.6:3.4) were added, and hydrogenation was carried out at a pressure of 80 bar of hydrogen gas which comprised 1000 ppm of carbon monoxide for 24 h. The conversion was >99%, the ee of the resulting D-citronellal was 87%.

After the product had been distilled off once again, the distillation residue was diluted with THF and stirred in an autoclave at 60° C. in the presence of 80 bar of synthesis gas ($H_2/CO=1:1$) for 20 h. Afterward, a further 32.96 g of neral (ratio of the neral/geranial double-bond isomers=96.6:3.4) were added and hydrogenation was carried out at a pressure of 80 bar of hydrogen gas which comprised 1000 ppm of carbon monoxide for 24 h. The conversion was 90%, the optical purity of the resulting D-citronellal was 88% ee.

The experiment was repeated once again with the addition of 33 g of neral (ratio of the neral/geranial double-bond isomers=96.6:3.4). At a conversion of 17%, D-citronellal was obtained with an optical purity of 89% ee.

The overall turnover number based on the overall yield of D-citronellal was 4975.

Example 9

Continuously Operated Asymmetric Hydrogenation of Neral

In a continuously operated laboratory apparatus, a solution of 2.13 g of $Rh(CO)_2$acac and 6.00 g of (R,R)-chiraphos in 70 g of THF and 60 g of Oxo oil 9N (BASF Aktiengesellschaft) which had been stirred beforehand for 20 h at 60° C. and a 1:1 $CO/H_2$ (vol/vol) pressure of 80 bar, and 170 g of neral (ratio of the neral/geranial double-bond isomers ca. 95:5) were introduced, and then the gas mixture in the preformation reactor of the apparatus was adjusted to 10 000 ppm of carbon monoxide in hydrogen (80 bar), and the temperature to 60° C. In the hydrogenation reactor, a gas mixture of 1000 ppm of carbon monoxide in hydrogen (80 bar) and a temperature of 25° C. were established.

The feed of fresh starting material was adjusted to 6 g/h. A product-containing fraction was distilled off continuously in vacuo such that the apparatus contents remained virtually constant. Over the course of 19 days, 6.01 mol (927.7 g) of D-citronellal were obtained. The overall turnover number based on the yield of D-citronellal was 10 914.

Example 10

Asymmetric Hydrogenation of Neral 12.3 mg of $Rh_4(CO)_{12}$ and 31.5 mg of (S,S)-chiraphos were dissolved in 15 g of toluene under a protective gas atmosphere and transferred to a 100 ml autoclave which had been flushed beforehand 3 times with $H_2$. The mixture was stirred at 1.5 bar of $H_2$ for 1.5 h and decompressed to standard pressure, and 1 g of neral (ratio of the neral/geranial double-bond isomers=98.7:1.3; substrate/catalyst ratio=100) dissolved in 15 g of toluene was added by means of a syringe. The reaction pressure was adjusted to 90 bar by injecting hydrogen. Gas chromatography reaction monitoring showed full conversion after 15 h and a yield, determined by gas chromatography, of 98% L-citronellal with an optical purity of 86% ee.

Examples of Step b): Cyclization of Citronellal to Isopulegol in the Presence of an Acidic Catalyst Example 11

Cyclization of Citronellal to Isopulegol with Recovery of 1,1-bis(2,6-diphenylphenol)-1-trifluoromethylethane ($Ia_2$-3)

Gas-chromatographic analyses (GC) were carried out according to the following method: 50 m CP-WAX, ID.: 0.32 mm, FD.: 1.2 µm; 80° C., 3° C./min-200° C., 15° C./min to 250° C.; $t_R$ (phenylcyclohexane): 30.7; $t_R$ (isopulegol): 26.3; $t_R$ (citronellal): 21.8.

The following HPLC method was used: CC250/4 Nucleodur C18 Gravity, 5 µm; C: water-0.05% $H_3PO_4$; D: acetonitrile 20:80; exit: 93 bar, 25° C.; $t_R$ (isopulegol): 3.3; $t_R$ (phenylcyclohexane): 10.5; $t_R$ (ligand ($Ia_2$-3)): 14.0.

Concentrations of the resulting reaction products in the distillation bottom and in the mother liquor (in each case in % by weight) were determined analytically by GC using an internal standard.

11.a) Cyclization of Citronellal 1,1-Bis(2,6-diphenylphenol)-1-trifluoromethylethane ($Ia_2$-3) (461 g, 0.785 mol) in anhydrous toluene (7.2 kg) was introduced as initial charge in a jacketed glass reactor with stirrer. At room temperature, a solution of triethylaluminum in toluene (445 ml, 400 mmol, 12% $AlEt_3$ in toluene) was added to the clear solution of the ligand. The solution was stirred for 1 h at 25° C. The resulting catalyst suspension was cooled to 0° C. and admixed over a period of 3 h with a mixture of citronellal (6697 g, 43 mol) and methyl pyruvate (33.6 g, 329 mmol). When the addition was complete, the reaction mixture was afterstirred for 3 h at 0° C. and for a further 2 h at 10° C. Toluene was separated off under reduced pressure. An isopulegol crude product was then separated off by distillation as top product with the addition of phenylcyclohexane (2770 g). Here, 3584 g of a bottom product were obtained.

11.b) Isolation of the Ligand ($Ia_2$-3)

3564 g of the bottom product from the cyclization of citronellal in the presence of a bis(diarylphenoxy)aluminum catalyst comprising phenylcyclohexane (69.9% by weight), isopulegol (3.05% by weight), citronellal (0.16% by weight) and citronellol (3.05% by weight) were introduced as initial charge in a jacketed reactor with stirrer and reflux condenser at a temperature of 90° C. 1792 g of a heated 2% strength NaOH solution were added to the heated solution. After stirring for one hour at 90° C., 1777 g of the aqueous phase were separated off from the organic phase. The remaining water from the organic phase was distilled off at 120° C. and 10 mbar. The hydrolyzed bottom product was cooled to 25° C. over the course of 12 hours. The resulting suspension of the ligand of the formula ($Ia_2$-3) was filtered and the ligand of the formula ($Ia_2$-3) obtained in this way was freed from volatile constituents at 3 mbar and 95° C. The ligand of the formula ($Ia_2$-3) was isolated as white solid with a yield of 282 g and a purity of 95%. According to HPLC analysis, the mother liquor (3130 g) comprised phenylcyclohexane (72.3% by weight), isopulegol (6.8% by weight) and ligand of the formula ($Ia_2$-3) (4.9% by weight). This demonstrates that the ligands used according to the invention are suitable in an advantageous manner for a continuous work-up. By contrast, when using the ligands described in EP-A 1 225 163, separation of the phases is not ensured in every case since these have a greater tendency to form stable emulsions.

Example 12

Cyclization of Citronellal to Isopulegol with Continuous Recovery of 1,1-bis(2,6-diphenylphenol)-1-trifluoromethylethane ($Ia_2$-3)

Analysis

Gas-chromatographic analyses were carried out according to the following method:
50 m CP-WAX, ID.: 0.32 mm, FD.: 1.2 µm; 80° C., 3° C./min-200° C., 15° C./min to 250° C.; $t_R$ (citronellal): 20.7; $t_R$ (isopulegol): 24.7; $t_R$ (phenylcyclohexane): 29.3; $t_R$ (citronellol): 31.7; $t_R$ (citronellyl citronellate): 48.2; $t_R$ (isopulegyl citronellate): 49.5.

12.a) Cyclization of Citronellal with Continuous Work-Up

In a jacketed glass reactor with stirrer, a solution of triethylaluminum in toluene (15% strength, 85 ml, 0.096 mol) was added at 20° C. over the course of about 10 min to a clear solution of 1,1-bis(2,6-diphenylphenol)-1-trifluoromethylethane ($Ia_2$-3) (114 g, 0.195 mol) in toluene (anhydrous, 1800 g). The solution was then stirred for 1 h at 20° C. The resulting catalyst suspension was transferred to a further jacketed glass reactor with stirrer, cooled to 0° C. and admixed over a period of 3 h with a mixture of D-citronellal (1620 g, 10.3 mol) and methyl pyruvate (8.1 g). When the addition was complete, the reaction solution was stirred at 0° C. until a content of <10 GC area % of D-citronellal was reached, warmed to 10° C. and stirred for a further 2 h at this temperature. Subsequently, the reaction solution was firstly transferred to a buffer container.

The reaction solution was passed to a plate column (15 plates, DN 50) continuously at a feed rate of 300 g/h. Toluene was removed from the column at a top pressure of about 100 mbar at a side take-off at the $10^{th}$ plate in the rectifying section, the bottom temperature being about 120° C. and the temperature of the side take-off and of the top of the column being 45° C. At the top of this column, the low-boilers were eliminated from the reaction solution.

A discharge of the bottom product from the plate column was fed continuously (120 to 140 g/h) into the center of a packed column (DN 50×120 cm, laboratory fabric packing, Sulzer DX). With the continuous addition of phenylcyclohexane (70 to 90 g/h) into the bottom of this packed column, L-isopulegol was distilled off as top product at a bottom temperature of 110° C. and a top pressure of 10 mbar. L-Isopulegol was isolated in a yield of 1625 g and in a purity of 93%.

12.b) Isolation of the Ligand (Ia$_2$-3) with Continuous Procedure

A discharge of the distillation bottom of the packed column was fed continuously (100 to 120 g/h) to a mixer-settler apparatus heated to 95° C. and consisting of two cascaded 250 ml stirred containers and a 150 ml phase separator. In the first 250 ml stirred container, the discharge of the distillation bottom of the packed column was admixed continuously with a feed of 2% strength sodium hydroxide solution (50 to 60 g/h). A discharge (150 to 180 g/h) of the mixed phase from the first stirred container was transferred to the 150 ml phase separator via the other 250 ml stirred container. In the phase separator, the continuous separation of the phases took place at a temperature of from 90 to 95° C. The height of the phase separation layer was controlled here with the help of conductivity measurements.

The discharge of the organic phase from the phase separator was collected continuously (100 to 120 g/h) in a further stirred container heated to 40 to 50° C. and left to crystallize prior to isolation of the ligand (Ia$_2$-3). A discharge of the aqueous phase from the phase separator was continuously pumped off.

The crystallized ligand (Ia$_2$-3) was filtered batchwise through a pressure filter at a nitrogen pressure of 4 bar. The filter cake was then washed with phenylcyclohexane. The washed ligand (106 g; HPLC % by weight: ligand 77%; phenylcyclohexane 22%) was dissolved in toluene and further used for producing the catalyst in step 2.a). The filtrate (919 g; % by weight according to GC: phenylcyclohexane 66%; L-isopulegol 5%; citronellol 6.1%; isopulegyl citronellate 4.3%; citronellyl citronellate 3.6%; % by weight according to HPLC: ligand 3.1%) was returned to the packed column described under 11.a).

Example 13

Continuous Purification of Isopulegol in a Dividing Wall Column

A laboratory dividing wall column was constructed from three glass sections with an internal diameter of 43 mm. The middle column section with a total length of 105 cm was provided with a glass dividing wall of thickness about 1 mm which had been fused in a fixed manner. In the region of the dividing wall, the column is equipped with 1 m of Sulzer DX packing on the feed side and 0.9 m of DX packing on the removal side. Above and below the dividing wall, glass sections of length 50 mm were used, each of which was equipped with 33 cm of Sulzer DX packings.

In separating performance measurements which were carried out with the xylene isomer mixture at a top pressure of 60 mbar, a total separating performance of about 32 theoretical plates over the entire column and about 18 theoretical plates in the dividing wall region was measured. The total number of theoretical plates present was thus about 50. The column was equipped with an oil-heated thin film evaporator (0.1 m$^2$) and a condenser cooled with cooling water at a temperature of 10° C. The inlet and outlet were in each case located in the middle of the dividing wall section.

The temperatures at various heights in the column and also the top pressure and the pressure drop over the column were measured by means of a measurement recording system. The column had flow meters in the inlets and outlets, and a flow meter with control of the return rate. This control system ensured a constant return rate, which also established a constant pressure difference. The division of the amount of liquid above the dividing wall between feed section and removal section of the dividing wall was realized by means of a swivel funnel on a time cycle.

In the middle of the column with respect to the feed section of the dividing wall, 250 g/h of an isopulegol mixture preheated to 80° C., which was obtained by cyclization of citronellal, as described in Example 12, was fed to the dividing wall column. The isopulegol mixture comprised, besides 93% by weight of isopulegol, 3.6% by weight of phenylcyclohexane, 0.3% by weight of citronellal, 0.1% by weight of citronellol and 1.3 GC area % toluene.

The fractions obtained were analyzed by gas chromatography using a standard GC. The internal standard used for the % by weight determination was 1-nonanol (weight ca. 10% of the total amount of sample).

Gas chromatography analyses were carried out by the following method:
50 m CP-Wax 52 CB, ID.: 0.32 mm, FD.: 1.2 µm; injector: 200° C.; detector: 250° C.; 80° C., 3° C./min-200° C., 15° C./min to 250° C.; t$_R$ (citronellal): 20.7; t$_R$ (isopulegol): 24.7; t$_R$ (phenylcyclohexane): 29.3; t$_R$ (citronellol): 31.7.

The column was operated at a top pressure of 100 mbar and a return rate of 1000 g/h. Here, a pressure drop of about 1 mbar was established. At the top of the column, a temperature of 109° C. was measured, and at the bottom a temperature of 139° C. (±0.5 K). The column was operated with 16 g/h (±2 g/h) of bottom take-off, and the distillate removal was adjusted by means of a balance control system to 4 g/h (±1 g/h). The reflux ratio was thus about 200:1. The condenser of the column was at a temperature of 10° C.

The liquid was divided above the dividing wall in a ratio of 1:2.4 (feed section:removal section). In the middle of the removal section of the dividing wall, a liquid side take-off (f) of about 230 g/h (±5 g/h) was removed with the aid of a membrane pump.

The pure product obtained at the side take-off comprised, besides 98.6% by weight of isopulegol, also 0.3% by weight of phenylcyclohexane. The distillation yield of isopulegol was thus 97.5%. The distillate comprised, besides 50 GC area % toluene, 47 GC % by weight of isopulegol and 1.0 GC % by weight of citronellal. In the bottom, besides 55% by weight of phenylcyclohexane, also 39.6% by weight of isopulegol and 1% of citronellol were analyzed.

Examples of Step c): Purification of Isopulegol by Crystallization

Example 14

Static Layer Crystallization of an Isopulegol Melt

A jacketed glass tube as a crystallizer was initially charged with 205 g of isopulegol of composition 95% (−)-n-isopulegol and 5% (+)-n-isopulegol (90% ee) with a melting point of 13° C. at a temperature of 15° C. The crystallizer was cooled down to 9° C. over the course of 30 h. The initially liquid product was present for the most part in solidified form at the end of the experiment. Subsequently, the jacket temperature was raised from 13° C. to 25° C. over the course of 10 h. Here, besides 70 g of mother liquor and 50 g of sweating fractions, 85 g of molten crystal layer were obtained. This end product had an optical purity of 99.9% ee based on (−)-n-isopulegol.

Example 15

Dynamic Layer Crystallization of an Isopulegol Melt

A stirred apparatus with a planar bottom cooled by means of a jacket (as described in G. F. Arkenbout, Melt Crystallization Technology, Lancater/PA, Technomic Publ. Co., 1995 (ch. 10.4.1)) was initially charged with 1003 g of isopulegol of composition 94.7% (−)-n-isopulegol and 5.3% (+)-n-isopulegol (89.4% ee) with a melting point of 10° C. at a temperature of 12° C. The cooling jacket of the crystallizer bottom was cooled to −14° C. over the course of 2 h. During this time, a 12 mm-thick crystal layer with a weight of 124 g was formed. The apparatus was then rotated through 180° and the jacket temperature was raised from 8° C. to 13° C. over the course of 10 h. This gave 52 g of sweating fractions and 124 g of molten crystal layer. This end product had an optical purity of 99% based on (−)-n-isopulegol.

Example 16

Suspension Crystallization of an Isopulegol Melt

A 1 l stirred crystallizer (as described in Arkenbout, ch. 10.4.2) was initially charged with 860 g of an isopulegol isomer mixture having an optical purity based on (−)-n-isopulegol: 95.2% (90.4% ee) as a melt. The melting temperature of the mixture was ca. 10° C. The stirrer used was a close-clearance helical stirrer. In-situ seeding of the melt was achieved by brief cooling down to 3° C. and subsequent heating to 9° C. The apparatus was then cooled to 7° C. with stirring over the course of 1.5 h. This established a solids content of the suspension of ca. 35% by weight. A sample was taken from this suspension and freed of adhering mother solution by centrifugation. After centrifuging for one minute, the crystals had a purity of 99% ee based on (−)-n-isopulegol, and of 99.4% after centrifuging for five minutes.

Comparative Example 1

Solution Crystallization of Menthol

In a 1 l stirred crystallizer, 560 g of a menthol isomer mixture (80% ee, purity with regard to (−)-menthol: 90%) were dissolved in 240 g of acetone. The saturation temperature of the mixture was 5.8° C. After cooling to 5.7° C., the supersaturated solution was seeded with 14 g of seed crystals of pure (−)-menthol and cooled further at a rate of from 0.5 to 1 K/h. Upon reaching a temperature of −6.9° C. and a solids content of 22.4% by weight in the suspension, a sample was taken and freed of adhering mother solution by centrifugation. The crystals had a purity of 98.2% (96.4% ee).

Comparative Example 2

Melt Crystallization of Menthol

A jacketed glass tube as a crystallizer was initially charged with 324 g of menthol of composition 95% (−)-menthol and 5% (+)-menthol (90% ee). The melting point of the mixture was 38° C. The crystallizer was cooled from 38.4° C. to 37.4° C. over the course of 15 h. The initially liquid product was present almost completely in solidified form at the end of the experiment. The jacket temperature was then raised from 38° C. to 39° C. over the course of 5 h. This gave two sweating fractions (51 g and 198 g) and 75 g of molten crystal layer. Analysis revealed that starting solution, both sweating fractions and the crystal layer had virtually identical ee values around 90%.

Examples of Step d): Catalytic Hydrogenation of Isopulegol to Menthol

Gas chromatography analyses were carried out according to the following method:
50 m CP-WAX, ID.: 0.32 mm, FD.: 1.2 µm; 80° C., 3° C./min-200° C., 10° C./min to 230° C.; $t_R$ (menthone): 26.9; $t_R$ (menthone): 28.1; $t_R$ (isopulegol): 30.7; $t_R$ (neomenthol): 31.2; $t_R$ (neoisomenthol): 32.6; $t_R$ (menthol): 32.7; $t_R$ (isomenthol): 34.1.

The isopulegol used was analyzed by gas chromatography as follows: 50 m CP-WAX, ID.: 0.32 mm, FD.: 1.2 µm; 80° C., 3° C./min-200° C., 15° C./min to 250° C.; $t_R$ (citronellal): 21.6; $t_R$ (isopulegol isomer): 25.4; $t_R$ (isopulegol): 25.9; $t_R$ (citronellol): 32.7.

Example 17

A hydrogenation apparatus consisting of a main reactor (MR) and a postreactor (PR) was used. The main reactor had 5 tubes, connected in series, having an internal diameter of 5 mm and a length of 1.3 m, which were filled with 61 g (127 ml) of a fixed-bed catalyst comprising 50% by weight of NiO, 17% by weight of CuO, 30.5% by weight of $ZrO_2$, 1.5% by weight of $MoO_3$ and 1% by weight of graphite in the form of tablets with a diameter and a height of in each case 3 mm. The postreactor (jacketed) consisted of a tube with an internal diameter of 5 mm and a length of 2.05 m, which was filled with 19 g of the same catalyst.

The fixed-bed catalyst installed in the main reactor and postreactor, comprising 50% by weight of NiO, 17% by weight of CuO, 30.5% by weight of $ZrO_2$, 1.5% by weight of $MoO_3$ and 1% by weight of graphite, was activated by the following method. The reactors were heated to 180° C. under ambient pressure with 42 l(STP)/h of nitrogen and 1.2 l(STP)/h of hydrogen, and kept under these conditions for 19 h. The hydrogen was increased from 1.2 to 6.5 l(STP)/h, and the reactor was kept at a temperature of 180° C. for a further 7.5 h. The nitrogen feed was turned off and the activation was continued with 6.5 l(STP)/h of hydrogen at 180° C. for 12 h. The hydrogen feed was then turned off and the nitrogen feed was adjusted to 6 l(STP)/h. The reactors were cooled to a temperature of 60° C. The hydrogen feed was reduced to 1.6 l(STP)/h and the isopulegol feed was started.

By means of a centrifugal pump, a circulation was pumped through the main reactor at a rate of about 500 g/h at a feed of L-isopulegol of 24.5 g/h (total amount 588 g) with a purity of 99.9% by weight and 99.8% ee. The hydrogen pressure was kept constant at 40 bar. The main reactor was operated at a temperature of 85° C. and the postreactor at 75° C. All pipelines were provided with electrical trace heating to prevent the crystallization of the enantiomerically pure L-menthol (m.p. 44° C.). This gave L-menthol in an amount of 597 g, corresponding to a rate of 24.9 g/h. The L-menthol obtained in this way (99.8% ee) was analyzed by gas chromatography. The chemical purity of the L-menthol discharge is listed in Table 1.

TABLE 1

| GC analysis of the L-menthol discharge (GC area %) | | | | | |
|---|---|---|---|---|---|
| Menthone/ isomenthone | L-Menthol | Neo- menthol | Neo- isomenthol | Iso- menthol | L-Isopulegol |
| 0 | 99.6 | 0.19 | 0 | 0 | 0.19 |

Example 18

Example 17 was repeated using L-isopulegol with a purity of 99.9% by weight and 99.8% ee, which was introduced into the reactor at a rate of 12.6 g/h (total amount 303 g) at a hydrogen pressure of 40 bar. The main reactor was heated to 80° C., the postreactor to 75° C. This gave L-menthol (99.8% ee) in an amount of 306 g, corresponding to a rate of 12.8 g/h. The chemical purity of the L-menthol discharge is listed in Table 2.

TABLE 2

GC analysis of the L-menthol discharge (GC area %)

| Menthone/<br>isomenthone | L-<br>Menthol | Neo-<br>menthol | Neo-<br>isomenthol | Iso-<br>menthol | L-<br>Isopulegol |
|---|---|---|---|---|---|
| 0 | 99.7 | 0.25 | 0 | 0 | 0 |

Example 19

Example 17 was repeated using L-isopulegol with a purity of 97.1% and 84% ee, which was introduced into the reactor at a rate of 24.5 g/h (total amount 466 g) at a hydrogen pressure of 40 bar. The main reactor was heated to 80° C., the postreactor to 70° C. The L-isopulegol used had the following composition: L-isopulegol: 97.1 GC % by weight, citronellol: 0.05 GC % by weight, citronellal: 0.40 GC % by weight, isopulegol isomer 0.45 GC % by weight, secondary component: 0.34 GC % by weight. This gave L-menthol (84% ee) in an amount of 468 g, corresponding to a rate of 24.6 g/h. The chemical purity of the L-menthol discharge is listed in Table 3.

TABLE 3

GC analysis of the L-menthol discharge (GC area %)

| Menthone/<br>iso-<br>menthone | L-<br>Menthol | Neo-<br>menthol | Neoiso-<br>menthol | Iso-<br>menthol | L-<br>Isopulegol | Secondary<br>comp. |
|---|---|---|---|---|---|---|
| 0.08/0 | 97.3 | 1.0 | 0.29 | 0.20 | 0.29 | 0.33 |

Example 20

A hydrogenation apparatus consisting of a main reactor (MR) and a postreactor (PR) was used. The main reactor had 5 tubes, connected in series, with an internal diameter of 5 mm and a length of 1.3 m, which were filled with 104 g (127 ml) of a fixed-bed catalyst consisting of 0.47% by weight of palladium on a $\gamma$-$Al_2O_3$ support in the form of extrudates with a length of 4 mm. The postreactor (jacketed) consisted of a tube with an internal diameter of 5 mm and a length of 1.9 m, which was filled with 27 g (35 ml) of the same catalyst.

By means of a centrifugal pump, a circulation was conducted through the main reactor at a rate of about 500 g/h at a feed of L-isopulegol of 24.5 g/h (total amount 588 g) with a purity of 99.8% and 99.8% ee at a constant hydrogen pressure of 30 bar. The main reactor was operated at a temperature of 50° C. and the postreactor at 60° C. All pipelines were provided with electrical trace heating to prevent crystallization of the enantiomerically pure L-menthol (m.p. 44° C.). This gave L-menthol (99.8% ee) in an amount of 597 g, corresponding to a rate of 24.9 g/h. The product obtained in this way was analyzed by gas chromatography. The results are listed in Table 4.

TABLE 4

GC analysis of the resulting L-menthol (GC area %)

| Menthone/<br>iso-<br>menthone | L-<br>Menthol | Neo-<br>menthol | Neoiso-<br>menthol | Iso-<br>menthol | L-<br>Isopulegol | Secondary<br>comp. |
|---|---|---|---|---|---|---|
| 0.64/0.56 | 97.5 | 0 | 0.66 | 0 | 0.29 | 0.10 |

Examples of Step e): Fine Distillation of Menthol

Example 21

A laboratory dividing wall column was constructed from five glass sections, each of length 1.2 m, with an internal diameter of 64 mm. A dividing wall made of sheet metal was inserted into the three middle sections. Above and below the dividing wall region, laboratory packings (Sulzer CY) were installed and, in the dividing wall region, metal fabric rings made of stainless steel with a diameter of 5 mm. In separating performance measurements which were carried out with the xylene isomer mixture at a top pressure of 60 mbar, an overall separating performance of 100 theoretical plates over the entire column and about 55 theoretical plates in the dividing wall region was measured. The total number of theoretical plates present was thus about 155. The column was equipped with an oil-heated thin film evaporator (0.1 $m^2$) and a condenser cooled with cooling water.

Temperatures at various levels in the column and the top pressure and the pressure drop over the column were measured by means of a measurement recording system. The column had flow meters in the inlets and outlets, and a return flow meter, the measurement of which served as the control parameter for the inlet temperature of the oil thermostat. This control system ensured a constant return rate, which also established a constant pressure difference. The division of the amount of liquid above the dividing wall between feed section and removal section of the dividing wall was realized by means of a swivel funnel on a time cycle.

In the middle of the column at a height of 331 cm from the feed section of the dividing wall, 1000 g/h of a liquid menthol of plant origin which had been preheated to 90° C. was fed to the column and comprised 99.58 GC area % menthol, 0.22 GC area % isopulegol, 0.11 GC area % other neomenthols and 0.03 GC area % isomenthol, and 0.02 GC area % neoisomenthol. The column was operated at a top pressure of 50 mbar and a return rate of 3.0 kg/h. Here, a pressure drop of about 34 mbar (±1 mbar) was established. At the top of the column, a temperature of 121° C. was measured, and in the bottom a temperature of 135° C. (±0.5 K). By means of a balance control system, the bottom take-off was fixed to 2 g/h (±1 g/h) and the distillate removal to 4 g/h (±1 g/h). The reflux ratio was thus about 750:1. The condenser of the column was at a temperature of 25° C. in order to prevent solids formation.

The liquid was divided above the dividing wall in a ratio of 1:1 (feed section:removal section). At a level of 300 cm in the removal section of the dividing wall, a gaseous side take-off (f) was removed and condensed in a glass condenser, from which, depending on the bottom fill level, about 992 to 995 g/h of pure product was removed by means of a pump.

The fractions obtained were analyzed by gas chromatography with the aid of a standard GC. Sample preparation: the (solidified) sample was heated to about 50° C. with melting and dissolved in toluene. The toluenic solution was injected into the gas chromatograph; during the integration, the toluene peak was correspondingly excluded.

Gas chromatography analyses were carried out according to the following method:
50 m CP-Wax 52 CB, ID.: 0.32 mm, FD.: 1.2 µm; injector: 200° C.; detector: 250° C.; 80° C.-3° C./min to 200° C., -10° C./min to 230° C./15 min;
$t_R$ (isopulegol): 30.07 min; $t_R$ (neomenthol): 31.08 min; $t_R$ (neoisomenthol): 32.5 min; $t_R$ (menthol): 32.8 min; $t_R$ (isomenthol): 33.8 min The pure product obtained at the side take-off comprised, as well as 99.94 GC area % L-menthol, also 0.02 GC area % isomenthol and traces of other menthol diastereomers. In the bottom take-off, 96.12 GC area % L-menthol was determined by GC analysis; the distillate comprised 44.7 GC area % L-menthol, 33.9 GC area % isopulegol, 12.9 GC area % neomenthol and 2.02 GC area % neoisomenthol. The distillation yield at the side take-off was thus above 99%.

Example 22

In the middle of the column at a height of 331 cm from the feed section of the dividing wall, 900 g/h of a liquid L-menthol of synthetic origin which had been preheated to 105° C., and obtained by catalytic hydrogenation of L-Isolulegol over a nickel-containing catalyst, and comprised 99.39 GC area % L-menthol, 0.29 GC area % isopulegol, 0.25 GC area % neomenthol and 0.011 GC area % isomenthol, and 0.044 GC area % neoisomenthol was fed to the dividing wall column from Example 21. The column was operated at a top pressure of 50 mbar and a return rate of 3.0 kg/h. Here, a pressure drop of about 35 mbar (±1 mbar) was established. At the top of the column, a temperature of 120° C. was measured, and in the bottom a temperature of 135° C. (±0.5 K). The column was operated without bottom take-off and the distillate removal was adjusted by means of a balance control system to 15 g/h (±1 g/h). The reflux ratio was thus about 200:1. The condenser of the column was at a temperature of 40° C. in order to prevent solids formation.

The liquid was divided above the dividing wall in a ratio of 1:1 (feed section:removal section). At a height of 300 cm in the removal section of the dividing wall, a gaseous side take-off (0 was removed and condensed in a glass condenser, from which, depending on the bottom fill level, about 885 to 890 g/h of pure product was drawn off by means of a pump.

The pure product obtained at the side take-off comprised, besides 99.93 GC area % L-menthol, also 0.027 GC area % neomenthol and traces of other menthol diastereomers. The distillate, also liquid at room temperature, comprised 73.1 GC area % L-menthol, 13.5 GC area % isopulegol, 10.9 GC area % neomenthol and 1.79 GC area % neoisomenthol. The continuously operated column was supplied with 22.05 kg of feed over the course of 24.5 h, and 21.6 kg of pure product were removed at the side take-off. The distillation yield at the side take-off was thus above 98.5%.

Example 23

In a glass laboratory column (theoretical number of plates of about 20) equipped with 1 m of Sulzer DX packing with an internal diameter of 50 mm, which is equipped with a boiler and a thin film evaporator (0.05 m²) in a pumped circulation system, 614 g of a synthetically produced L-menthol with 98.0 GC area % L-menthol, 1.69 GC area % isopulegol and 0.33 GC area % neomenthol were distilled batchwise at a top pressure of 50 mbar. The condenser of the column was operated with water at a temperature of 40° C.

The temperatures at the top of the column were between 122 and 123° C., and the bottom temperature was between 124° C. at the start and 125° C. toward the end of the distillation. The distillate container was electrically heated to about 60° C. in order to prevent solidification of the fraction. At a reflux ratio of 15:1, 3 fractions (31, 45 and 138 g) were obtained, and at a reflux ratio of 10:1 a further distillate fraction of 116 g. The first fraction obtained comprised 75.5 GC area % L-menthol, 19.6 GC area % isopulegol and 3.01 GC area % neomenthol and, and also remained liquid at room temperature. The second fraction comprised 90.6 GC area % menthol, 7.03 GC area % isopulegol and 1.49 GC area % neomenthol, and the third correspondingly 98.09 GC area % L-menthol, 0.98 GC area % isopulegol and 0.3 GC area % neomenthol. In the fourth fraction, a menthol purity of 99.52 GC area % was ultimately achieved. 197 g of residue were isolated from the boiler, with 98.5 GC area % L-menthol.

Example 24

A further laboratory dividing wall column was constructed from three glass sections with an internal diameter of 43 mm. The middle column section with a total length of 105 cm was provided with a glass dividing wall of thickness about 1 mm which had been fused in a fixed manner. In the region of the dividing wall, the column is equipped with 1 m of Sulzer DX packing on the feed side and 0.9 m of DX packing on the removal side. Above and below the dividing wall, glass sections of length 50 mm were used, each of which was equipped with 33 cm of Sulzer DX packings.

In separating performance measurements which were carried out with the xylene isomer mixture at a top pressure of 60 mbar, a total separating performance of about 32 theoretical plates over the entire column and about 18 theoretical plates in the dividing wall region was measured. The total number of theoretical plates present was thus about 50. The column was equipped with an oil-heated thin film evaporator (0.1 m²) and a condenser cooled with cooling water at a temperature of 25° C. The inlet and outlet were each present at the middle of the dividing wall and were each configured with heating. Return lines and bottom discharge lines were likewise provided with electrical trace heating.

The temperatures at various heights in the column, and also the top pressure and the pressure drop over the column were measured by means of a measurement recording system. The column had flow meters in the inlets and outlets, and a flow meter with control of the return rate. This control system ensured a constant return rate, which also established a constant pressure difference. The division of the amount of liquid above the dividing wall between feed section and removal section of the dividing wall was realized by means of a swivel funnel on a time cycle.

In the middle of the column with respect to the feed section of the dividing wall, 120 g/h of a liquid, virtually racemic menthol of synthetic origin, which had been preheated to 80° C. and obtained by catalytic hydrogenation of isolulegol over a nickel-containing catalyst, and comprised 85.1% by weight of menthol, 0.2% by weight of isopulegol, 3.4% by weight of neomenthol and 0.98% by weight of isomenthol, and 1.25 GC area % neoisomenthol was fed continuously to the dividing wall column. Moreover, 1.5 GC % by weight of the hydrocarbon phenylcyclohexane was present.

The fractions obtained were analyzed by gas chromatography with the help of a standard GC. Sample preparation: the (in some cases solidified) sample was heated to about 50°

C. with melting and dissolved in toluene. The toluenic solution was injected into the gas chromatograph; during the integration, the toluene peak was correspondingly excluded. The internal standard used for the % by weight determination was diethylene glycol diethyl ether (weight ca. 10% of the total amount of sample).

Gas chromatography analyses were carried out according to the following method:
50 m CP-Wax 52 CB, ID.: 0.32 mm, FD.: 1.2 µm; injector: 200° C.; detector: 250° C.; 80° C.-3° C./min to 200° C., −10° C./min to 230° C./15 min;
$t_R$ (diethylene glycol diethyl ether): 23.0 min, $t_R$ (isopulegol): 30.07 min; $t_R$ (neomenthol): 31.08 min; $t_R$ (neoisomenthol): 32.5 min; $t_R$ (menthol): 32.8 min; $t_R$ (isomenthol): 33.8 min, $t_R$ (phenylcyclohexane): 35.2 min The column was operated at a top pressure of 18 mbar and a return rate of 850 g/h. Here, a pressure drop of about 3 mbar was established. At the top of the column, a temperature of 101° C. was measured, and in the bottom a temperature of 105° C. (±0.5 K). The column was operated with 15 g/h (±2 g/h) of bottom take-off and the distillate removal was adjusted by means of a balance control system to 50 g/h (±5 g/h). The reflux ratio was thus about 17:1. The condenser of the column was at a temperature of 25° C. in order to prevent solids formation.

The liquid was divided above the dividing wall in a ratio of 3:4 (feed section:removal section). In the middle of the removal section of the dividing wall, a liquid side take-off (f) of about 55 g/h (±5 g/h) was removed with the aid of a membrane pump.

The pure product obtained at the side take-off comprised, besides 98.2% by weight of menthol, also 0.14% by weight of neomenthol and 0.92 GC % by weight of isomenthol, and 0.25 GC area % of neoisomenthol and about 0.45% by weight of phenylcyclohexane. The pure product had a specific rotation of −0.9 grd/(ml*g) (determination in accordance with USP30/NF25 "menthol").

The distillate, also liquid at room temperature, comprised 79.6% by weight of menthol, 0.67 GC % by weight of isopulegol, 6.9 GC % by weight of neomenthol and 2.5 GC area % neoisomenthol, and also 3.0% by weight of phenylcyclohexane. In the bottom, besides 85.7% by weight of menthol, 2.9% by weight of isomenthol was also measured.

The invention claimed is:

1. A method for producing optically active menthol, comprising the steps
  a2) pretreating an asymmetric rhodium complex with carbon monoxide to provide an asymmetric, hydrogenation rhodium catalyst that is soluble in a reaction mixture,
  b2) including neral and/or geranial in the reaction mixture, and in the presence of the catalyst of step a2), hydrogen, and 100 to 1200 ppm carbon monoxide, the hydrogenation of the neral and/or geranial provides optically active citronellal,
  c2) cyclization of optically active citronellal to give optically active isopulegol in the presence of an acidic catalyst,
  d2) purification of the optically active isopulegol by crystallization, and
  e2) contacting the optically active isopulegol from step d2) with a hydrogenation catalyst to provide the optically active menthol.

2. A method for producing optically active menthol, comprising the steps
  a1) forming an asymmetric rhodium catalyst that includes chiral diphos ligands and carbon monoxide,
  b1) catalytic hydrogenation of a mixture of neral and geranial to provide optically active citronellal in the presence of the catalyst formed from step a1) and 100 to 1200 ppm carbon monoxide,
  c1) cyclization of the optically active citronellal to give provide optically active isopulegol in the presence of an acidic catalyst,
  d1) purification of optically active isopulegol of step c1) by melt crystallization, and
  e1) catalytic hydrogenation of the purified isopulegol of step d1) to give optically active menthol, and purifying the optically active menthol by distillation, where the purification is conducted in a dividing wall column having 50 to 200 theoretical plates and one or more side take-off points at an absolute operating pressure of from 5 to 500 mbar.

3. The method of claim 2, wherein the cyclization according to step c1) is carried out in the presence of a Lewis-acidic aluminum-containing catalyst.

4. The method of claim 1, wherein in step e2), the hydrogenation catalyst is pretreated with a gas mixture comprising carbon monoxide and hydrogen.

5. The method of claim 2, wherein the dividing wall column has 100 to 200 theoretical plates.

6. A method for producing enantiomerically enriched L-(−)-menthol and racemic or enantiomerically depleted menthol, comprising the steps
  a) asymmetrically catalytically hydrogenating neral to give D-(+)-citronellal with an enantiomer excess of from 70 to 99%, the asymmetric hydrogenation conducted in the presence of an asymmetric rhodium catalyst that includes chiral diphos ligands,
  b) cyclizing the D-(+)-citronellal of a) in the presence of an acidic catalyst to give L-(−)-isopulegol,
  c) purifying L-(−)-isopulegol of b) by crystallization to give enantiomerically enriched L-(−)-isopulegol and racemic or enantiomerically depleted isopulegol,
  d) catalytically hydrogenating the L-(−)-isopulegol of c) to give L-(−)-methanol,
  e) catalytically hydrogenating the racemic or enantiomerically depleted isopulegol of c) to give racemic or enantiomerically depleted menthol.

7. The method of claim 1, wherein the crystallization is conducted in a static layer crystallizer comprising an internal heat exchanger surface.

8. The method of claim 1, wherein the acidic catalyst is an aluminum-containing Lewis-acid catalyst.

9. The method of claim 1, wherein step c2) provides enriched isopulegol with a chemical purity of at least about 95% by weight.

10. The method of claim 2, wherein the acidic catalyst is a diarylphenoxyaluminum compound.

11. A method for producing optically active menthol comprising:
  providing a hydrogenation rhodium catalyst with the asymmetric ligand (R,R)-chiraphos;
  providing a mixture of neral and geranial, wherein the mixture comprises 0.5 to 20% by weight geranial and 99.5 to 80% by weight neral, or the mixture is citral;
  contacting the mixture of neral and geranial with the (R,R)-chiraphos, rhodium catalyst in the presence of hydrogen and 100 to 1200 ppm carbon monoxide, the hydrogenation of the neral and geranial provides optically active D-(+)-citronellal;
  contacting the optically active D-(+)-citronellal in the presence of a Lewis-acidic aluminum-containing catalyst to provide optically active L-(−)-isopulegol;

purification of the L-(−)-isopulegol by distillation or crystallization and separating the L-(−)-isopulegol from the Lewis-acidic catalyst; and contacting the purified L-(−)-isopulegol with a hydrogenation catalyst to give L-(−)-menthol.

12. The method of claim 11, wherein the purification of the L-(−)-isopulegol is carried out by vacuum distillation in the presence of a solvent having a boiling point that is at least 20° C. greater than the boiling point of the L-(−)-isopulegol.

13. The method of claim 11, wherein the purification of the L-(−)-isopulegol is carried out by melt crystallization to provide L-(−)-isopulegol with a purity of 95 to 99.5% by weight.

14. The method of claim 1, wherein the asymmetric, hydrogenation rhodium catalyst includes diphos ligands selected from the group consisting of formulae (VIII), (IX), and (X)

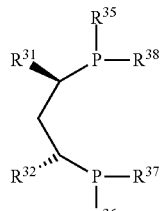

(VIII)

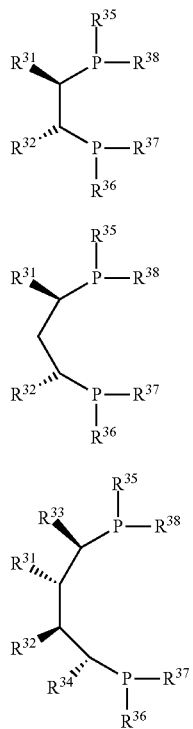

(IX)

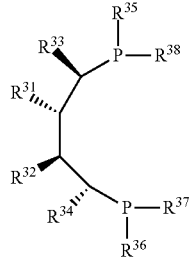

(X)

wherein:

R$^{31}$, R$^{32}$ in each case independently of one another are an unbranched, branched or cyclic alkyl radical having 1 to 20 carbon atoms, which can optionally carry one or more, ethylenic double bonds and/or one or more substituents selected from OR$^{39}$, NR$^{40}$R$^{41}$, halogen, C$_6$-C$_{10}$-aryl and C$_3$-C$_9$-hetaryl, and R$^{31}$ and R$^{32}$ together can form a 4 to 20-membered ring which can include one or more O atoms;

R$^{33}$, R$^{34}$ in each case independently of one another are hydrogen or straight-chain or branched C$_1$- to C$_4$-alkyl;

R$^{35}$, R$^{36}$, R$^{37}$, R$^{38}$ are in each case C$_6$- to C$_{10}$-aryl, which can optionally carry 1 to 4, substituents selected from C$_1$- to C$_4$-alkyl, C$_6$- to C$_{10}$-aryl, C$_1$- to C$_4$-alkoxy and amino; and R$^{39}$, R$^{40}$, R$^{41}$ in each case independently of one another are hydrogen, C$_1$-C$_4$-alkyl, C$_6$-C$_{10}$-aryl, C$_7$-C$_{12}$-aralkyl or C$_7$-C$_{12}$-alkylaryl, where R$^{40}$, R$^{41}$ together can form an alkylene chain having 2 to 5 carbon atoms, which may be interrupted by N or O.

15. The method of claim 6, wherein the chiral diphos ligands are selected from the group consisting of formulae (VIII), (IX), and (X)

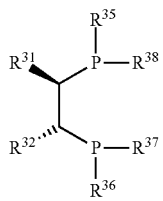

(VIII)

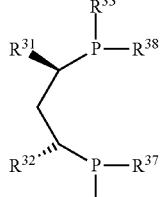

(IX)

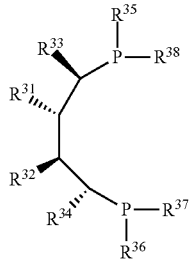

(X)

wherein

R$^{31}$, R$^{32}$ in each case independently of one another are an unbranched, branched or cyclic alkyl radical having 1 to 20 carbon atoms, which can optionally carry one or more, ethylenic double bonds and/or one or more substituents selected from OR$^{39}$, NR$^{40}$R$^{41}$, halogen, C$_6$-C$_{10}$-aryl and C$_3$-C$_9$-hetaryl, and R$^{31}$ and R$^{32}$ together can form a 4 to 20-membered ring which can include one or more O atoms;

R$^{33}$, R$^{34}$ in each case independently of one another are hydrogen or straight-chain or branched C$_1$- to C$_4$-alkyl;

R$^{35}$, R$^{36}$, R$^{37}$, R$^{38}$ are in each case C$_6$- to C$_{10}$-aryl, which can optionally carry 1 to 4, substituents selected from C$_1$- to C$_4$-alkyl, C$_6$- to C$_{10}$-aryl, C$_1$- to C$_4$-alkoxy and amino; and R$^{39}$, R$^{40}$, R$^{41}$ in each case independently of one another are hydrogen, C$_1$-C$_4$-alkyl, C$_6$-C$_{10}$-aryl, C$_7$-C$_{12}$-aralkyl or C$_7$-C$_{12}$-alkylaryl, where R$^{40}$, R$^{41}$ together can form an alkylene chain having 2 to 5 carbon atoms, which may be interrupted by N or O.

* * * * *